(12) United States Patent
Bram et al.

(10) Patent No.: US 11,913,068 B2
(45) Date of Patent: Feb. 27, 2024

(54) METHODS FOR NUCLEIC ACID SIZE DETECTION OF REPEAT SEQUENCES

(71) Applicant: Asuragen, Inc., Austin, TX (US)

(72) Inventors: Eran Bram, Cedar Park, TX (US); Raghav Shroff, Austin, TX (US); Andrew Hadd, Austin, TX (US); Blake Printy, Austin, TX (US)

(73) Assignee: Asuragen, Inc., Austin, TX (US)

( * ) Notice: Subject to any disclaimer, the term of this patent is extended or adjusted under 35 U.S.C. 154(b) by 1074 days.

(21) Appl. No.: 16/549,684

(22) Filed: Aug. 23, 2019

(65) Prior Publication Data

US 2020/0048696 A1 Feb. 13, 2020

Related U.S. Application Data

(63) Continuation of application No. 15/343,057, filed on Nov. 3, 2016, now abandoned.

(60) Provisional application No. 62/250,476, filed on Nov. 3, 2015.

(51) Int. Cl.
*G01N 33/48* (2006.01)
*G01N 33/50* (2006.01)
*C12Q 1/6858* (2018.01)

(52) U.S. Cl.
CPC .................. *C12Q 1/6858* (2013.01)

(58) Field of Classification Search
CPC .............. C12Q 1/6858; C12Q 1/6851; C12Q 2525/151
See application file for complete search history.

(56) References Cited

U.S. PATENT DOCUMENTS

| 7,329,487 B2 | 2/2008 | Lee |
| 8,409,805 B2 | 4/2013 | Latham |
| 8,679,757 B2 | 3/2014 | Latham et al. |
| 2012/0107824 A1 | 5/2012 | Latham et al. |

FOREIGN PATENT DOCUMENTS

| WO | WO 03/006692 A1 | 1/2003 |
| WO | WO 2014/015273 A1 | 1/2014 |
| WO | WO 2015/073650 A2 | 5/2015 |

OTHER PUBLICATIONS

Bruland et al., (1999) "Accurate determination of the number of CAG repeats in the Huntington disease gene using a sequence-specific internal DNA standard", Clin Genet. 55(3):198-202.
Chinese Office Action of Application 201680074751.5 dated Sep. 27, 2021.
Baskaran et al., (1996) "Uniform Amplification of a Mixture of Deoxyribonucleic Acids with Varying GC Content", Genome Res. 6(7):633-638.

(Continued)

*Primary Examiner* — Russell S Negin
(74) *Attorney, Agent, or Firm* — Finnegan, Henderson Farabow, Garrett & Dunner, LLP

(57) ABSTRACT

Disclosed herein are data processing and calculating annotation systems and devices, and corresponding methods, for nucleic acid analysis. In particular, disclosed herein are methods for sizing a repeat region of a nucleic acid sample. For example, the methods disclosed herein use a ladder of amplification products to determine nucleic acid size.

10 Claims, 28 Drawing Sheets

Specification includes a Sequence Listing.

(56) References Cited

OTHER PUBLICATIONS

Chen et al., (2010) "An Information-Rich CGG Repeat Primed PCR that Detects the Full Range of Fragile X Expanded Alleles and Minimizes the Need for Southern Blot Analysis", J. Mol. Diagn. 12(5):589-600.
European Application No. EP 16 86 2998, Asuragen, Inc., Supplementary European Search Report, dated Feb. 12, 2019.
European Application No. EP 16 86 2998, Asuragen, Inc., Supplementary European Search Report, dated May 28, 2019.
European Application No. EP 16 86 2998, Asuragen, Inc., Supplementary Partial European Search Report, dated Feb. 20, 2019.
International Patent Application No. PCT/US2016/060389, Asuragen, Inc., International Search Report and Written Opinion, dated Feb. 27, 2017.
Khan et al., (1996) "Construction of an internal standard for semiquantitative polymerase chain reaction analysis of heat shock proteins", Electrophoresis, 17(1):40-43.
Levinson et al., (1994) "Improved Sizing of Fragile X CCG Repeats by Nested Polymerase Chain Reaction", Am. J. Med. Genet. 51(4):527-534.
Moncke-Buchner et al., (2002) "Counting CAG repeats in the Huntington's disease gene by restriction endonuclease EcoP15I cleavage", Nucleic Acids Research, 30(16):1-7.
Musso et al., (2006) "Betaine, Dimethyl Sulfoxide, and 7-Deaza-dGTP, a Powerful Mixture for Amplification of GC-Rich DNA Sequences", J. Mol. Diag. 8(5):544-550.
Nygren et al., (2008) "Methylation-Specific Multiplex Ligation-Dependent Probe Amplification Enables a Rapid and Reliable Distinction Between Male FMR1 Premutation and Full-Mutation Alleles", J. Mol. Diag. 10(6):496-501.
Southern, (1979) "Measurement of DNA Length by Gel Electrophoresis", Analytical Biochemistry 100(2):319-323.
Tassone et al., (2008) "A Rapid Polymerase Chain Reaction-Based Screening Method for Identification of All Expanded Alleles of the Fragile X (FMR1) Gene in Newborn and High Risk Populations," J. Mol. Diagn. 10(1):43-49.
Yrigollen et al., (2011) "The Role of AGG Interruptions in the Transcription of FMR1 Premutation Alleles", PLOS One 6(7):e21728.
Second Office Action in counterpart application for Chinese Patent Application No. 201680074751.5 dated Apr. 28, 2022, (12 Pages).
Williams et al., Comparative Semi-Automated Analysis of (CAG) Repeats in the Huntington Disease Gene: Use of Internal Standards, 13 Molecular and Cellular Probes 283-89 (1999).
Olejniczak et al., Accurate and Sensitive Analysis of Triplet Repeat Expansions by Capillary Electrophoresis, 26 Electrophoresis 2198-207 (2005).

Fig. 4A
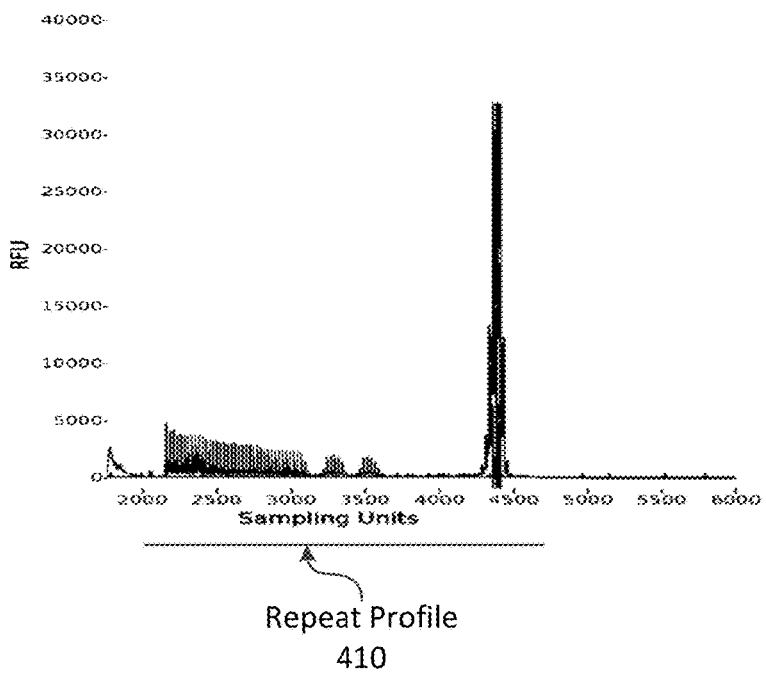
Repeat Profile 410
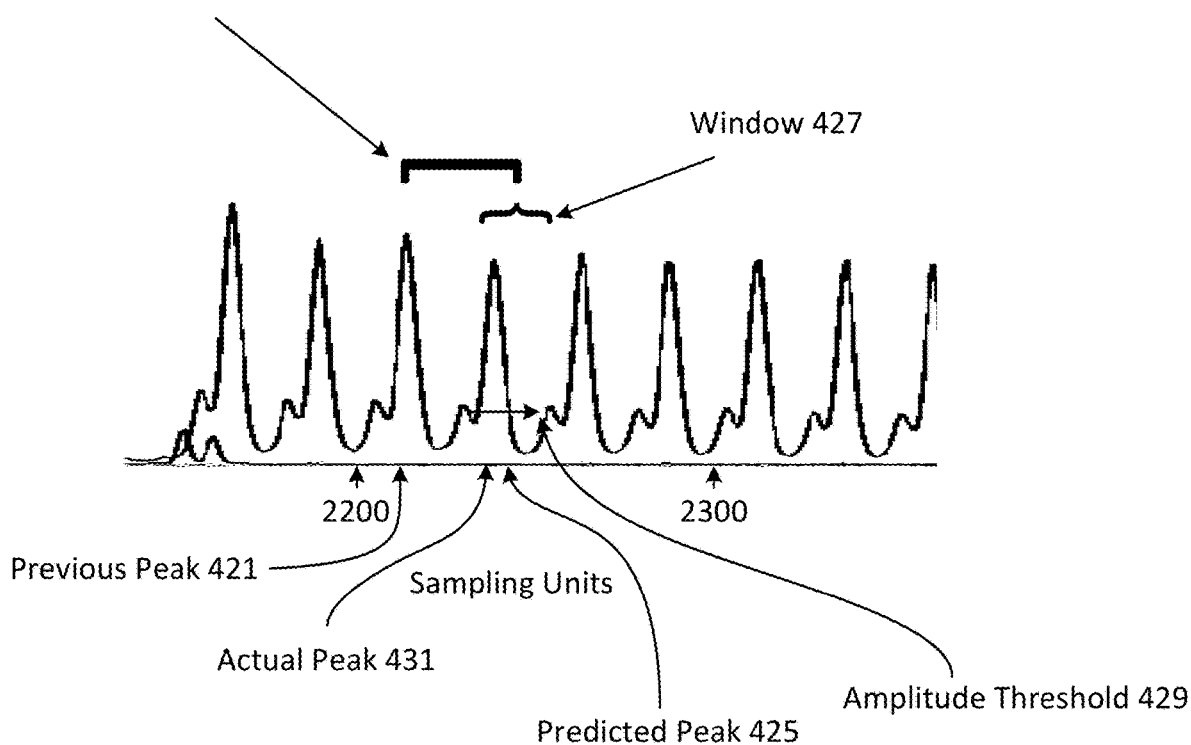
Fig. 4B

METHODS FOR NUCLEIC ACID SIZE DETECTION OF REPEAT SEQUENCES

This application is a continuation of U.S. patent application Ser. No. 15/343,057, filed Nov. 3, 2016, and claims the benefit of priority to Provisional Application No. 62/250,476, filed Nov. 3, 2015, each of which is hereby incorporated by reference in its entirety.

This work was partially supported by the National Institute of Health under Grant R44HD066953 and R44HD069132. Thus, the government has certain rights in the invention.

The instant application contains a Sequence Listing which has been submitted electronically in ASCII format and is hereby incorporated by reference in its entirety. Said ASCII copy, created on Nov. 18, 2016, is named 10256_0052-00000_SL.TXT and is 12,546 bytes in size.

The present disclosure relates to data processing and calculating annotation systems and devices, and corresponding methods, for nucleic acid analysis. In particular, the disclosure relates to methods of sizing a repeat region of a nucleic acid.

Genetic loci that comprise regions of nucleotide repeats (e.g., homopolymer regions, dinucleotide repeats, trinucleotide repeats, hexanucleotide repeats etc.) are common in the human or animal genome. Genetic loci that have enriched GC (guanine-cytosine) content are also common, while loci having AT (adenine-thymine) rich content have been reported and studied. In some circumstances, the expansion of GC or A/T-rich regions, or the expansion of nucleotide repeats, can be associated with various disease states. For example, the expansion of CGG repeats in the 5' untranslated region (UTR) of the Fragile X Mental Retardation-1 gene (FMR1), located on the X chromosome, is associated with Fragile X Syndrome (FXS) and a variety of disorders and phenotypes. In most people, the trinucleotide CGG is repeated approximately 5-44 times in the 5' untranslated region (UTR) of the FMR1 gene ("CGG repeat region"). Expansions in this region to greater than about 45 CGG repeats, and particularly to greater than about 200 CGG repeats, have been associated with FXS. FXS phenotypes may include mental retardation, autism, anxiety, and other cognitive or behavioral conditions. (*J. Mol. Diag.* 10(6): 496-501 (2008)). Likewise, expansion of the CCG trinucleotide repeat region ("CCG repeat region") in the 5' UTR of the FMR2 gene is associated with X-linked intellectual disabilities, and particularly with Fragile X syndrome E (FRAXE). FRAXE is a common form of X-linked mental retardation. In other instances, repeat length polymorphisms have been associated with disease states. For example, intron 6 of the TOMM40 gene contains a poly-T repeat region and has been reported to exhibit a repeat length polymorphism in the population (rs 10524523). The TOMM40 poly-T size has been reported as being associated with late-onset Alzheimer's Disease and with cognitive performance in the elderly (See *The Pharmacogenetics Journal* 10:375-3840 (2010); and *Alzheimer's and Dementia* 9:132-136 (2013)). Furthermore, an intronic $(G_4C_2)_n$ hexanucleotide repeat expansion in the C9ORF72 gene has been observed in the general population with a frequency of approximately 1/600 and is present in approximately 10% of all amyotrophic lateral sclerosis (ALS) and frontotemporal dementia (FTD) cases. Fewer than 30 repeats are considered normal, whereas pathogenic C9ORF72 expansions may include hundreds to thousands of repeats. Methods for accurately measuring, sizing, and reconstructing patient genotypes can therefore be beneficial for the diagnosis and treatment of these and other diseases.

Methods for evaluating sequences comprising nucleotide repeats, such as the CGG and CCG repeats in FMR1 and FMR2, include restriction enzyme digestion and polymerase chain reaction (PCR) strategies. Restriction digest analysis can provide a crude measure of the size of a repeat region. However, restriction digest analysis can be limited in resolution, does not easily detect short interruptions (such as AGG interruptions within a CGG repeat region), and cannot determine methylation status.

PCR strategies may provide greater accuracy in sizing the repeat regions and reconstructing various genotypes. However, limitations exist in the amplification and sequencing of genetic loci that comprise long repeat sequences or those containing GC or A/T-rich sequences that hinder the ability to reconstruct genotypes for these loci. Efforts to optimize PCR procedures for the analysis of the CGG repeats in FMR1, for example, have been attempted, and include modifications to conventional PCR assays. (See *Genome Res.* 6(7): 633-8, (1996); *J. Mol. Diag.* 8: 544-550, (2006); and *Am. J. Med. Genet.* 51(4): 527-34, (1994)). More recently, PCR techniques have been developed that permit more reliable amplification of genomic loci having over 200 CGG or CCG repeats.

Current workflow strategies often employ PCR with size resolution techniques, for example, capillary electrophoresis. Capillary electrophoresis improves the quantitative capabilities of PCR-based assays to allow for accurate resolution of DNA products down to the single base resolution. To facilitate sizing of DNA products, external standard calibrators are typically employed, for example, using pooled dye-labeled DNA fragments of known sizes, which span the size range of interest for a specific capillary electrophoresis application. Nonetheless, despite the enabling capabilities achieved by applying these standards, this approach has several shortcomings which include but are not limited to: i. the high cost of commercially available dye labeled DNA ladders; ii. the reduced capillary electrophoresis multiplexing bandwidth caused by the use of a dedicated dye channel for the standard ladder iii. the sizing inaccuracy resulting from skewed electrophoretic mobility due to base composition or sequence differences between the PCR amplified analyte and the standard DNA, requiring the use of custom DNA ladders, which can be laborious or inefficient to use in sizing, specifically for repeat disorder PCR products. Furthermore, fragment size analysis of FMR1 PCR and CE products is conducted manually by trained operators, which is laborious for large sample sets, and can introduce both ambiguity and subjectivity into an otherwise streamlined workflow.

Accordingly, there is a need in the art for improved methods of sizing repeat regions and reconstructing genotypes associated with those repeat regions, which may also be GC or A/T-rich. The methods disclosed herein relate to the generation and use of an internal standard, alone or in combination with an external standard, in an amplification based method for sizing one or more nucleotide repeat regions and reconstructing a genotype therefrom.

BRIEF DESCRIPTION OF DRAWINGS

The drawings are not necessarily to scale or exhaustive. Instead, emphasis is generally placed upon illustrating the principles of the inventions described herein. The accompanying drawings, which are incorporated in and constitute a part of this specification, illustrate several embodiments consistent with the disclosure and, together with the description, serve to explain the principles of the disclosure. In the drawings:

FIG. 4A depicts an exemplary channel of a ladder of amplification products.

FIG. 4B depicts generation of an internal sizing standard using a repeat profile.

FIG. 7A. depicts a sample with a poor ROX ladder. FIG. 7B. depicts a sample with a poor PCR amplification. FIG. 7C depicts a sample with a contamination peak.

FIG. 14A depicts detection of additional gene-specific products. FIG. 14B depicts detection of a low-abundance expanded allele.

FIG. 15A depicts a normal sample. FIG. 15B depicts a premutation sample with a minor allele.

FIG. 25A depicts the full sample including all called genotypes, while FIG. 25B depicts a zoomed-in version showing the full mutation call.

DETAILED DESCRIPTION

Figure 1:
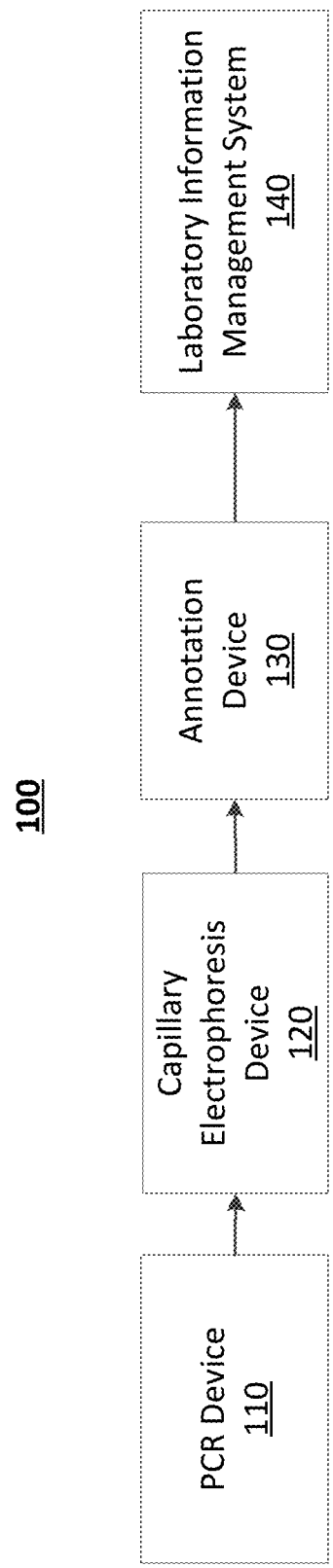
FIG. 1 depicts an exemplary high-level representation of a system for genotype peak sizing.

Reference will now be made in detail to certain exemplary embodiments according to the present disclosure, certain examples of which are illustrated in the accompanying drawings.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose. To the extent publications and patents or patent applications incorporated by reference contradict the invention contained in the specification, the specification will supersede any contradictory material.

To assist in understanding the present invention, certain terms are first defined. Additional definitions are provided throughout the application.

The use of the word "a", "an", or "the" when used in conjunction with the term "comprising" in the claims and/or the specification can mean "one", but it is also consistent with the meaning of "one or more", "at least one", and "one or more than one".

In this application, the use of the singular includes the plural unless specifically stated otherwise. Also in this application, the use of "or" means "and/or" unless stated otherwise. Furthermore, the use of the term "including", as well as other forms, such as "includes" and "included", are not limiting. Any range described herein will be understood to include the endpoints and all values between the endpoints.

The term "A/T-rich", "A/T-richness", and "repeating A/T-rich segment" as used herein refers to a homopolymeric segment, defined below, or a segment comprising $(T_nA)_m$, $(AT_n)_m$, $(TA_n)_m$, or $(A_nT)_m$, wherein n is 2 or greater and m is such that the length of the repeating A/T-rich segment is 10 or more residues. The value of n need not be constant throughout the segment. Thus, examples of repeating A/T-rich segments include AATAATAATAAT (SEQ ID NO: 52), AATAAATAAT (SEQ ID NO: 53), AAATAAAAAT (SEQ ID NO: 54), AATAAAAAAT (SEQ ID NO: 55), etc. With respect to a segment comprising $(T_nA)_m$, $(AT_n)_m$, $(TA_n)_m$, or $(A_nT)_m$, in some embodiments, n is a value ranging from 2 to 10. In some embodiments, n is a value ranging from 3 to 10. In some embodiments, n is a value ranging from 4 to 10. In some embodiments, n is a value ranging from 2 to 8. In some embodiments, n is a value ranging from 3 to 8. In some embodiments, n is a value ranging from 4 to 8. In some embodiments, n is a value ranging from 2 to 6. In some embodiments, n is a value ranging from 3 to 6. In some embodiments, m is a value ranging from 2 to 20. In some embodiments, m is a value ranging from 3 to 20. In some embodiments, m is a value ranging from 4 to 20. In some embodiments, m is a value ranging from 2 to 15. In some embodiments, m is a value ranging from 3 to 15. In some embodiments, m is a value ranging from 4 to 15. In some embodiments, m is a value ranging from 2 to 10. In some embodiments, m is a value ranging from 3 to 10. In some embodiments, m is a value ranging from 4 to 10. In some embodiments, m is a value ranging from 2 to 8. In some embodiments, m is a value ranging from 3 to 8. In some embodiments, m is a value ranging from 4 to 8. In some embodiments, the length of the repeating A/T-rich segment is in the range from about 10 to about 60 residues. In some embodiments, the length of the repeating A/T-rich segment is in the range from about 10 to about 40 consecutive residues. In some embodiments, the length of the repeating A/T-rich segment is in the range from about 15 to about 40 consecutive residues. In some embodiments, the length of the repeating A/T-rich segment is in the range from about 20 to about 40 consecutive residues. In some embodiments, the length of the repeating A/T-rich segment is in the range from about 5 to about 50 consecutive residues. In some embodiments, the length of the repeating A/T-rich segment is in the range from about 10 to about 50 consecutive residues. In some embodiments, the length of the repeating A/T-rich segment is in the range from about 15 to about 50 consecutive residues. In some embodiments, the length of the repeating A/T-rich segment is in the range from about 20 to about 50 consecutive residues. In some embodiments, the length of the repeating A/T-rich segment is in the range from about 5 to about 60 consecutive residues. In some embodiments, the length of the repeating A/T-rich segment is in the range from about 10 to about 60 consecutive residues. In some embodiments, the length of the repeating A/T-rich segment is in the range from about 15 to about 60 consecutive residues. In some embodiments, the length of the repeating A/T-rich segment is in the range from about 20 to about 60 consecutive residues. Unless otherwise indicated, a repeating A/T-rich segment can comprise an interruption as explained in the following paragraph. In some embodiments, a repeating A/T-rich segment does not comprise an interruption.

As used herein, "bleed-over" occurs when fluorescently-labelled PCR products fluoresce with sufficient intensity produce significant signal in an overlapping fluorescent frequency emission band logically assigned to a differently-labelled PCR product. This bleed-over may arise when fluorescence detectors for the different channels have overlapping spectral sensitivities. This bleed-over may convolute the process of detecting products native to a particular channel in a multiplex reaction. For example, PCR products in the HEX channel may fluoresce with sufficient intensity to affect the recorded signal intensities in the ROX channel.

As used herein, "GC-rich", "GC-richness", and "repeating GC-rich segment" refer to a homopolymeric segment, defined below comprising G or C nucleotides, or to a segment comprising repeating patterns of G and C nucleotides. CGG repeats, CCG repeats, GGGGCC repeats, and optional interspersed AGG interruptions are included. The fraction or percentage of total nucleobase residues in a nucleic acid or a fragment of that nucleic acid that are guanine residues, cytosine residues, or analogs thereof defines the richness. For example, a 100 nucleotide sequence that contains exactly 30 cytosines, exactly 30 guanines, exactly one cytosine analog, and exactly one guanine analog has a GC-richness of 62%. In some embodiments, a "GC-rich" nucleic acid or region of a nucleic acid is one that contains more than about 50% guanine residues, cytosine residues, or analogs thereof (e.g., more than about 50, 51, 55, 60, 65, 70, 75, 80, 85, 90, 95, 96, 97, 98, 99, or 99.5% guanine residues, cytosine residues, or analogs thereof, or any percentage in between).

The term "homopolymeric segment" as used herein refers to segments of nucleic acid which comprise a nucleotide such as G, C, A, T, or U repeated in series.

Unless otherwise indicated, a homopolymeric segment, a GC-rich repeat, or A/T-rich repeat can comprise an interruption in an otherwise consecutive or repeating series of nucleotides. The interruption can be any number of nucleotides differing from the other nucleotides making up the series. In some embodiments, the interruption is a single nucleotide. An example of a homopolymeric segment comprising an interruption is a first number of T residues, then one C residue, and then a second number of T residues. An example of a homopolymeric segment comprising an interruption is a first number of U residues, then one C residue, and then a second number of U residues. Another example of a homopolymeric segment comprising an interruption is a first number of A residues, then one G residue, and then a second number of A residues. The first and second numbers of A, T, or U residues in the foregoing examples can be, e.g., in the range of 5 to 10. In some embodiments, the first and second numbers of A, T, or U residues in the foregoing examples are in the range of 6 to 10. In some embodiments, the first and second numbers of A, T, or U residues in the foregoing examples are in the range of 7 to 10. In some embodiments, the first and second numbers of A, T, or U residues in the foregoing examples are in the range of 8 to 10. In some embodiments, the first and second numbers of A, T, or U residues in the foregoing examples are in the range of 9 to 10. Alternatively, a homopolymeric segment can comprise a consecutive series of nucleotides (which is not interrupted).

As used herein, a "nucleic acid" is any contiguous nucleobase residues or analogs that have been isolated from a subject and/or for which sizing of a repeat region is sought. A nucleic acid can comprise a gene, gene fragment, or genomic region isolated from a subject. As used herein, a "genotype" is or comprises the nucleobase sequence of a nucleic acid.

As used herein, a "peak location" may be an index of a signal where the slope changes sign from positive to negative. Other definitions of peak location may be used without departing from the envisioned systems and methods. For example:

$$f(x,c) = \Delta_1 \operatorname{sgn}(\Delta_1 s(x,c))$$

$$P(c) = \{x | x, f(x,c) = -2 \wedge s(x,c) > 50\}$$

Here $s(x, c)$ represents the signal intensity at index x for instrument channel c, $f(x, c)$ is the derivative of the sign of the first-order derivative of the signal intensity, and $P(c)$ represents the set of all indices in channel c for which $f(x, c)$ equals −2.

As used herein a "peak shoulder" may be the point nearest a peak location at which the signal intensity exceeds an amplitude threshold. This amplitude threshold may be two standard deviations above a mean value. In some embodiments, the standard deviations and mean values may be calculated over an interval of the signal including the peak shoulder. The left peak shoulder may be the peak shoulder with a lower index than the peak location, and the right peak shoulder may be the peak shoulder with a higher index than the peak location. In other embodiments, peak shoulders can be identified by fitting a statistical distribution to the peak, where shoulders are assigned to locations at the tail ends (defined by percentile cutoff) of the distribution. In yet other embodiments, peak shoulders can be identified using the first order derivative of the peak region, where shoulders are assigned to locations where the absolute value of the first order derivative is below a threshold.

As used herein, a "repeat region" or "nucleotide repeat region" refers to a nucleic acid or a region of a nucleic acid comprising a repeating sequence of 1-20 nucleobase residues in length (e.g., a homopolymer, a dinucleotide, trinucleotide, tetranucleotide, pentanucleotide, hexanucleotide sequence, etc.) wherein the short sequence is repeated 2 or more times (e.g., 2, 3, 4, 5, 10, 15, 20, 50, 100, 200, 500, or more repeats). For example, a nucleotide repeat would encompass a region of a nucleic acid in which a short sequence such as CGG, CCG, GGGGCC is repeated two or more times. A repeat region may be a homopolymer, e.g. a run of A or T nucleotides, and a repeat region may include interruptions or repeat variants. A nucleic acid or a region of a nucleic acid can (but does not need to be) be both a repeat and a GC rich region, or a repeat and AT rich region. For example, the nucleic acid or region of a nucleic acid can comprise di-, tri-, tetra-, penta-, or hexa-nucleotide repeats of guanine residues, cytosine residues, or analogs thereof.

A nucleic acid can comprise one or more nucleotide repeat regions, A/T-rich regions, or GC-rich regions that contain one or more interruptions. As used herein, an "interruption" in a nucleic acid refers to the presence of one or more nucleobase residues or analogs in the nucleic acid that are inconsistent with the repeat pattern or, in a GC-rich region, comprises a nucleobase other than G or C (or analogs thereof). For example, a GC-rich, nucleotide repeat region could encompass a sequence comprising 40 CGG trinucleotide repeats with two AGG sequences interspersed within the 40 CGG repeats.

As used herein "signal intensities" are expressed herein in terms of "relative fluorescence units" or RFUs, but other measures of fluorescence may be used without departing from the envisioned systems and methods.

As used herein, the term "template" refers to a nucleic acid that interacts with a primer for extension in a nucleic acid synthesis reaction.

I. Sizing a Repeat Region and Reconstructing a Genotype

FIG. 1 depicts an exemplary high-level representation of a system 100 for genotype peak sizing. System 100 may comprise PCR device 110, capillary electrophoresis (CE) device 120, annotation device 130, and laboratory information management system 140. PCR device 110 may comprise a PCR instrument familiar to those skilled in the art. For instance, the PCR device may comprise a thermal cycle. As a non-limiting example, an ABI model 9700 thermal cycler may be used. PCR device 110 may be configured to amplify a repeat region of a nucleic acid sample.

CE device 120 may comprise a CE instrument familiar to those skilled in the art. For instance, ABI model 3100, 3130, 3730, or 3500 CE devices may be used. CE device 120 may be configured to perform high resolution fragment analysis. In some embodiments, the CE device may be used to separate amplification fragments by size. In some embodiments, the CE device may be used to generate a ladder of amplification products. In other embodiments, the CE device may be used to generate a ladder of amplification products by separating amplification fragments by size. In certain embodiments, the CE device is used to obtain repeat region sizing information. CE device 120 may be configured to provide an output indicative of this ladder of amplification products. In some embodiments, this output may comprise one or more channels in a file. The file may be an .FSA file, or a similar file known to one of skill in the art.

Annotation device 130 may comprise a purpose-built computing device, a desktop, workstation, all-in-one system, computer cluster, terminal, mainframe, mobile computing device, or other computing device. Annotation device 130 may be standalone; or may be part of a subsystem, which may be part of a larger system. For example, Annotation device 130 may comprise distributed servers that are remotely located and communicate over a public network or a dedicated private network. In some embodiments, annotation device 130 may be implemented at least in part as a virtual system on a cloud-computing infrastructure. Consistent with disclosed embodiments, annotation device 130 may include or communicate with one or more storage devices configured to store data and/or software instructions. The stored data and/or software instructions may include one or more software programs. For example, the stored data and/or software instructions may include analysis software. Annotation device 130 may execute this analysis software to perform one or more methods consistent with the disclosed embodiments. In certain aspects, annotation device 130 may execute this analysis software remotely from annotation device 130. For example, annotation device 130 may access one or more remote devices to execute the stored analysis software. In certain embodiments, annotation device 130 may be configured as a particular apparatus or system based on the storage, execution, and/or implementation of the analysis software. Annotation device 130 may be configured to communicate with other components of system 100, such as CE device 120 and Laboratory Information Management System 140. Annotation device 130 may communicate with these components of system 100 using Ethernet, FireWire, USB, RS-232, SCSI, WLAN, Bluetooth, or a similar interface.

Annotation device 130 may be configured to size repeating genomic regions. This sizing may be performed automatically. For example, annotation device 130 may be configured to generate FMR1 sizing results. Annotation device 130 may employ a combination of signal-processing, statistical, and machine learning techniques to size repeating genomic regions, and/or identify gene product locations. Annotation device 130 may be configured to output results of this analysis, and/or intermediate step of this analysis. Annotation device 130 may be configured to output these indications to laboratory information management system 140, or to a display, printer, storage device, or another system.

Laboratory information management system 140 may comprise purpose-built computing device, a desktop, workstation, all-in-one system, computer cluster, terminal, mainframe, mobile computing device, or other computing device. Laboratory information management system 140 may be stand alone; or may be part of a subsystem, which may be part of a larger system. For example, laboratory information management system 140 may comprise distributed servers that are remotely located and communicate over a public network or a dedicated private network. In some embodiments, laboratory information management system 140 may be implemented at least in part as a virtual system on a cloud-computing infrastructure. Consistent with disclosed embodiments, laboratory information management system 140 may include or communicate with one or more storage devices configured to store data and/or software instructions. The stored data and/or software instructions may include one or more software programs. Laboratory information management system 140 may execute the stored one or more software programs to perform one or more methods consistent with the disclosed embodiments. In certain aspects, laboratory information management system 140 may execute the stored one or more software programs remotely from laboratory information management system 140. For example, laboratory information management system 140 may access one or more remote devices to execute the stored one or more software programs. In certain embodiments, laboratory information management system 140 may be configured as a particular apparatus or system based on the storage, execution, and/or implementation of the software instructions. Laboratory information management system 140 may be configured to communicate with other components of system 100, such as CE device 120 and Annotation device 130. Laboratory information management system 140 may communicate with these components of system 100 using Ethernet, FireWire, USB, RS-232, SCSI, WLAN, Bluetooth, or a similar interface.

Laboratory information management system 140 may be configured to manage samples and corresponding data. In other aspects, laboratory information management system 140 may be used to automate workflows. In some embodiments, laboratory information management system 140 may be configured to execute Sample Manager Laboratory Information Management System, Watson Laboratory Information Management System, Nautilus Laboratory Information Management System or Clinical Laboratory Information Management System. One of skill in the art would readily know of appropriate Laboratory Information Management Systems. Laboratory Information Management System 140 may be configured to receive information concerning the genomic sample. Laboratory Information Management System 140 may receive this information from Annotation Device 130, a storage device, or another system. Laboratory Information Management System 140 may be configured to arrange this information for storage and display to relevant clinical practitioners.

As would be appreciated by one of skill in the art, the particular arrangement of devices depicted in FIG. 1 is not intended to be limiting. For example, system 100 may include additional devices or fewer devices. Likewise, functions of individual devices of system 100 may be distributed across multiple devices, and multiple functions performed by different devices of system 100 may be performed by a single device.

System 100 may be configured to perform the following methods of sizing a repeat region and optionally reconstructing a genotype. In some embodiments, size analysis of a repeat region can comprise amplifying the repeat region and using the amplified products to determine the repeat region size. In certain embodiments, the repeat region of a nucleic acid is amplified, obtaining a ladder of amplification products. The ladder of amplification products may be used as an internal standard in sizing a repeat region. In some embodiments, the internal standard is used without any external standards. In other embodiments, the internal standard is used in combination with an external standard. In some embodiments, the external standard may be a fluorescent-labeled DNA ladder, for example a ROX size standard. In more specific embodiments, the ROX size standard may be the ROX 1000 Size Ladder (Asuragen P/N: 145194). The amplification pattern of the repeat region may be used to size the repeat region. The skilled artisan will understand that the ladder of amplification products will have certain features useful in sizing the repeat region, such as a repeat profile, a repeat element periodicity, a first amplification product, an amplification product count, and/or a constant element length. In certain embodiments, the sizing information may be used to generate a reconstructed genotype, to diagnose a disorder in a patient, or to diagnose a risk of a disorder of the offspring of the patient, or in treating a patient with a disorder associated with an expanded repeat region.

In various embodiments, a method of sizing a repeat region comprises amplifying a nucleic acid or a portion comprising the repeat region to generate a series of amplification fragments. The amplification fragments may be of different lengths corresponding to the number of repeating units amplified in a particular fragment. In other embodiments, the nucleic acid or portion comprising the repeat region is not amplified, but directly isolated and fragmented for further analysis. In some embodiments, the amplification fragments (or unamplified fragments) are separated by size, e.g., using a size resolution technique such as high resolution fragment analysis, for example, analysis using a genetic analyzer, microchip analyzer (such as Bioanalyzer), capillary electrophoresis, or another high resolution method for analyzing the amplification fragments of the ladder. For instance, capillary electrophoresis may be used. In certain embodiments, microchip electrophoresis may be used, such as a Bioanalyzer. In various embodiments, the high resolution fragment analysis is used to generate a ladder of amplification products, e.g., by evaluating peaks corresponding to amplification products of differing repeat number in a capillary electrophoresis electropherogram. In some embodiments, the known length of the individual repeating unit can be used to convert the ladder of repeat units to a ladder indicating nucleotide base pair (bp) length. For example, amplification and capillary electrophoresis of a nucleic acid region comprising repeating units will result in a ladder of amplification fragments differing in length by units of three nucleotides, allowing for conversion of the ladder to a measure of nucleotide length using parameter information for the ladder of amplification products. In some embodiments, the ladder is used to determine the size of the repeat region in a nucleic acid of interest. In some embodiments, the ladder is used to determine the size of other portions of the nucleic acid comprising the repeat region or the size of other nucleic acids of interest amplified in the same reaction that generates the ladder. In some embodiments, the repeat region size is used to reconstruct a genotype. In certain embodiments, additional parameters such as the distance in the forward and reverse directions to any interruptions in the repeat region are also identified (e.g., from the capillary electrophoresis electropherogram) and used with the repeat region size to reconstruct a genotype. In certain embodiments, an interruption in the repeat sequence is detected in the ladder of amplification products.

In various embodiments, disclosed herein are methods for sizing and/or characterizing a repeat region, for example, a GC-rich or A/T-rich region and/or methods to reconstruct a genotype comprising the repeat region. For example, the methods disclosed herein can be used to size a repeat region from a nucleic acid or fragment thereof comprising CGG repeats or CCG repeats. The methods disclosed herein can be used to size a repeat region from a nucleic acid or a fragment thereof comprising an A/T-rich segment, such as a homopolymeric segment. The methods of sizing can be used in conjunction with methods to determine interruptions in the repeat region, as well as methods of reconstructing a genotype based on the sizing (alone or in combination with additional parameters such as the distance in the forward and reverse directions to any interruptions in the repeat region).

In some embodiments, the methods can be used to size the repeat region of the FMR1 or FMR2 gene, or fragments thereof, or the 5' UTR of FMR1 or FMR2, or fragments thereof, isolated from a subject. In certain embodiments, the methods disclosed herein are used to assist in reconstructing a genotype for an FMR1 gene in a sample from a subject, including the CGG repeat pattern and the location and organization of AGG interruptions and/or methylation within the 5' UTR of FMR1. In other embodiments, the methods disclosed herein are used to assist in reconstructing a genotype for FMR2, including the CCG repeat pattern, as for FMR1. In yet other embodiments, the methods disclosed herein are used to assist in sizing the repeat region of TOMM40. In other embodiments, the methods are used to assist in sizing the repeat region of C9ORF72.

In some embodiments, the methods disclosed herein are used to determine the size of a repeat region of a nucleic acid or fragment thereof from a patient sample, wherein the nucleic acid has at least one repeat or GC or A/T-rich region, and wherein the related genotype from at least one of the parents of the patient is not known. In some embodiments, the nucleic acid of interest or a portion comprising the repeat region is isolated from a patient sample. Various isolation and purification methods are known and can be used. In certain embodiments, the methods disclosed herein are used to determine the size of a CGG or CCG repeat region, for example of FMR1 or FMR2 from a patient sample. In certain embodiments, the methods disclosed herein are used to determine the size of a hexameric repeat, for example the GGGGCC repeat of C9ORF72 from a patient sample. In certain embodiments, the methods disclosed herein are used to determine the size of a homopolymeric repeat, for example the poly-T repeat region of TOMM40 from a patient sample. In some embodiments, the related genotype, such as the FMR1, FMR2, C9ORF72, or TOMM40 genotype, from at least one of the parents of the patient is not known.

In certain embodiments, a method for the sizing of a repeat region of a nucleic acid sample comprises providing a sample from a patient, wherein the sample contains a nucleic acid or fragment thereof having one or more repeat regions or GC-rich or AT-rich regions. In some embodiments, information characterizing the nucleic acid (i.e., "parameter information") is collected. In some embodiments, the parameter information includes features obtained from the ladder of amplification products, including a repeat profile, a repeat element periodicity, a first amplification product, an amplification product count, and/or a constant element length. In some embodiments, a repeat profile is the pattern of peaks observed in the electropherogram. In some embodiments, the amplification products are the spread of fragments produced by amplifying the repeat region using the selected primers. In some embodiments, the total length of the repeat region is calculated from the parameter information. In some embodiments, additional parameter information is generated, for example, information on the percent of GC-richness or A/T-richness of a region of interest, and/or the distance in the forward and reverse directions to any interruptions in the repeat or GC-rich or A/T-rich region. In some embodiments, the collected information is automatically analyzed using an apparatus comprising a processor programmed to conduct an automated analysis. In certain embodiments, the accuracy of the sizing solution or solution genotype can be evaluated by manually analyzing the genotype to confirm that it comports with the parameter information, or by conducting any other confirmatory assay (e.g., restriction enzyme digest, Sanger sequencing, or other forms of high throughput sequencing). In some embodiments, the sizing solution or solution genotype can be displayed or stored electronically on a computer or can be printed for subsequent diagnostic and therapeutic purposes.

In certain embodiments, the sizing of the repeat region can be used to detect a mutation or genotype, or to diagnose, or assist in diagnosing a disorder, or risk of a disorder associated with a mutation in a repeat region, for example, an FMR1, FMR2, C9ORF72, or TOMM40 related mutation, genotype, or disorder.

In various embodiments, sizing information characterizing a repeat region of a nucleic acid can be obtained using any suitable method, such as amplification and high resolution fragment analyses. In certain embodiments, the sizing information (e.g., a subset of parameter information, information characterizing the nucleic acid, includes a repeat profile, a repeat element periodicity, a first amplification product, an amplification product count, and/or a constant element length relating to the ladder of amplification products. In some embodiments, overall length of the repeat region, as well as the distance from the start of the repeat region to a first or subsequent interruption in the forward direction and in the reverse direction are included in the parameter information. In some embodiments, an apparatus is provided, comprising a processor programmed to analyze parameter information and to size a repeat region, and optionally to reconstruct a genotype from the information. In certain embodiments, the apparatus is used to reconstruct the genotype of the nucleic acid from the information characterizing the nucleic acid. In some embodiments, the apparatus evaluates sizes of each product in the ladder of amplification products. In some, all possible genotype reconstructions based on the length of the repeat region and the interruptions in the forward or reverse direction to select the reconstruction that satisfies all the parameter information (e.g., the genotype that places the interruptions in the correct positions in both the forward and reverse directions). In certain embodiments, the apparatus provides a report of the reconstructed genotype that can be displayed on a screen, saved digitally for future use, or printed as a paper record.

In various embodiments, parameter information regarding a nucleic acid can be obtained using any method known in the art, so long as it includes information regarding the ladder of amplification products suitable for sizing a nucleic acid. In some embodiments, the parameter information includes a repeat profile, a repeat element periodicity, a first amplification product, an amplification product count, and/or a constant element length relating to the ladder of amplification products. Restriction enzymes that cleave a nucleic acid site-specifically can be used to analyze a repeat region and thereby generate parameter information. For example, the presence of AGG interruptions within a CGG repeat tract of FMR1 can be detected by digesting a nucleic acid with the restriction enzyme EciI (New England Biolabs Inc., Ipswich, MA, USA). Restriction enzymes may be used to generate a ladder of digested products, which can be used for sizing. In other embodiments, amplification methods can be used to generate the necessary information. For example, restriction digest and/or PCR methods can be used with an FMR1 or FMR2 gene or fragments thereof isolated from a patient in determining one or more CGG or CCG repeat regions.

The methods disclosed in International Publication No.: WO/2014/015273 are hereby incorporated by reference in their entirety, including the PCR and capillary electrophoresis methods disclosed in the publication for analyzing repeat regions, obtaining parameter information including repeat size, and the distance in the forward and reverse direction to any interruptions in the repeat region.

In some embodiments, suitable methods for amplifying the repeat region to generate amplification products include polymerase chain reaction (PCR), real-time PCR (RT-PCR), nucleic acid sequence-base amplification (NASBA), ligase chain reaction, multiplex ligatable probe amplification, invader technology (Third Wave), rolling circle amplification, in vitro transcription, strand displacement amplification, transcription-mediated amplification (TMA), RNA (e.g., Eberwine) amplification, loop-mediated isothermal amplification, or any other methods that are known to one of skill in the art. For example, FMR1 repeat region amplification can be generated using a two-tier PCR approach with a CGG linker primer and the Human FMR1 PCR kit (Asuragen Inc., Austin, TX, USA). See Tassone et al., *J Mol Diagn.* 10(1):43-49 (2008); Chen et al., *J Mol Diagn.* 12(5): 589-600 (2010); Yrigollen et al., *PLoS One* 6(7): e21728 (2011). For example, a nucleic acid comprising at least one GC-rich region can be analyzed by (a) providing at least two PCR primers, including a first primer comprising CGG, CCG, GCG, CGC, GCC, or GGC repeats, and a second primer that anneals to a position outside of the GC-rich region; (b) performing PCR on the nucleic acid with the at least two different primers, wherein the PCR produces a set of PCR products; (c) resolving the set of PCR products with a high resolution technique (such as capillary electrophoresis) to generate a representation of PCR product size and abundance; and (d) deriving from the PCR product size and abundance information the length of the GC-rich region and whether or where within the GC-rich region an interruption is located.

In various embodiments, PCR-amplified nucleic acids are analyzed to obtain repeat region sizing information, for example using a high resolution fragment analyzer such as a capillary electrophoresis (CE) instrument familiar to those skilled in the art, such as ABI model 3100, 3130, 3730, or 3500 CE instruments (Applied Biosystems, Carlsbad, CA). Other implementations, include any instrument capable of electrophoretically or otherwise sizing and/or sequencing an amplified nucleic acid, can also be used. Any other method of collecting sizing and other parameter information can also be used (e.g., Sanger sequencing or other forms of high throughput sequencing). Various techniques for analyzing the FMR1 gene or fragments thereof, such as the PCR methods described in US Publication Nos. 2010/0209970, 2010/0243451, and 2012/0107824, often yield a ladder of amplification products separated in length by the repeat spacing. For example, repeat region sizing and genotype reconstruction to characterize the CGG and CCG repeat loci in the 5' UTRs of FMR1 and FMR2 or fragments thereof can be generated using the methods described in U.S. Patent Publication No. 2010/0243451, including the primers, polymerase, reagents, and reaction conditions disclosed at paragraphs [0040]-[0051], [0056]-[0060], [0065]-[0067], [0089], [0094], and [0104], which are hereby incorporated by reference. Additionally, US Publication Nos. 2010/0209970, 2010/0243451, and 2012/0107824 describe PCR methods and reagents for analyzing GC-rich regions that are hereby incorporated by reference in their entirety.

For example, in some embodiments FMR1 and FMR2 parameter information can be generated using a primer that anneals outside of a repeat region and a primer that anneals to repeat sequences, sequence permutations, or reverse complements of the sequences (GCG, CCG, CGC, GCC, or GGC). The primers that can anneal outside (upstream or downstream) of the repeat region may be forward or reverse primers. The primers may anneal to sequences flanking the repeat region. Examples of forward primers include CGG TGG AGG GCC GCC TCT GAG C (SEQ ID NO: 1), CAG GCG CTC AGC TCC GTT TCG GTT T (SEQ ID NO: 2), CAG TCA GGC GCT CAG CTC CGT TTC G (SEQ ID NO: 3), TCC GGT GGA GGG CCG CCT CTG AGC (SEQ ID NO: 4), GGT TCG GCC TCA GTC AGG CGC TCA GCT CCG TTT CG (SEQ ID NO: 5), GGG TTC GGC CTC AGT CAG GCG CTC AGC TCC GTT TCG (SEQ ID NO: 6), GCG GGC CGG GGG TTC GGC CTC AGT CA (SEQ ID NO: 7), CAG CGG GCC GGG GGT TCG GCC TCA G (SEQ ID NO: 8), GCA GCG GGC CGG GGG TTC GGC CTC A (SEQ ID NO: 9), GGG CCG GGG GTT CGG CCT CAG TCA G (SEQ ID NO: 10), GGG GTT CGG CCT CAG TCA GGC GCT CA (SEQ ID NO: 11), GGG GTT CGG CCT CAG TCA GGC GCT CAG (SEQ ID NO: 12), GGC GCT CAG CTC CGT TTC GGT TTC ACT TCC (SEQ ID NO: 13), TCA GGC GCT CAG CTC CGT TTC GGT TTC A (SEQ ID NO: 14), CAC TTC CGG TGG AGG GCC GCC TCT GA (SEQ ID NO: 15), TTC CGG TGG AGG GCC GCC TCT GAG C (SEQ ID NO: 16), and TCA GGC GCT CAG CTC CGT TTC GGT TTC ACG GCG GCG GCG GCG GA (SEQ ID NO: 44). Examples of reverse primers include CGC ACT TCC ACC ACC AGC TCC TCC A (SEQ ID NO: 17), GGA GCC CGC CCC CGA GAG GTG (SEQ ID NO: 18), GGG AGC CCG CCC CCG AGA GGT (SEQ ID NO: 19), CGC ACT TCC ACC ACC AGC TCC TCC AT (SEQ ID NO: 20), CGG GAG CCC GCC CCC GAG AGG TG (SEQ ID NO: 21), CCG GGA GCC CGC CCC CGA GAG GT (SEQ ID NO: 22), CCG GGA GCC CGC CCC CGA GAG GTG (SEQ ID NO: 23), CGC CGG GAG CCC GCC CCC GAG AGG TG (SEQ ID NO: 24), GCG CCG GGA GCC CGC CCC CGA GAG GT (SEQ ID NO: 25), CGC CGG GAG CCC GCC CCC GAG AGG T (SEQ ID NO: 26), GCG CCA TTG GAG CCC CGC ACT TCC ACC A (SEQ ID NO: 27), GCG CCA TTG GAG CCC CGC ACT TCC A (SEQ ID NO: 28), AGC GCC ATT GGA GCC CCG CAC TTC C (SEQ ID NO: 29), CGC CAT TGG AGC CCC GCA CTT CCA C (SEQ ID NO: 30), TTG GAG CCC CGC ACT TCC ACC ACC A (SEQ ID NO: 31), AGC CCC GCA CTT CCA CCA CCA GCT CCT C (SEQ ID NO: 32), GAG CCC CGC ACT TCC ACC ACC AGC TCC T (SEQ ID NO: 33), CAT TGG AGC CCC GCA CTT CCA CCA CCA G (SEQ ID NO: 34), CCC GCA CTT CCA CCA CCA GCT CCT CCA TCT (SEQ ID NO: 35), TAG AAA GCG CCA TTG GAG CCC CGC ACT TCC (SEQ ID NO: 36), AAG CGC CAT TGG AGC CCC GCA CTT CC (SEQ ID NO: 37), AAG CGC CAT TGG AGC CCC GCA CTT CCC CGC CGC CGC CG (SEQ ID NO: 43), and AAG CGC CAT TGG AGC CCC GCA CTT CCC CGC CGC CGC CGC CT (SEQ ID NO: 45).

In some embodiments, FMR1 and FMR2 assays can use the primers (SEQ ID NO: 38)
TCAGGCGCTCAGCTCCGTTTCGGTTTCACTTCCGGT, (SEQ ID NO: 39)
AGCGTCTACTGTCTCGGCACTTGCCCGCCGCCGCCG, (SEQ ID NO: 40)
TCA GGC GCT CAG CTC CGT TTC GGT TTC A,
and (SEQ ID NO: 41)
TCAGGCGCTCAGCTCCGTTTCGGTTTCA CGGCGGCGGCGGCGG.

The methods can additionally involve using primers comprising the sequence of any of SEQ ID NOs 1-38 or 40 and comprising additional repeats of CGG or the permutations and reverse complements thereof (e.g., GCG, CCG, CGC, GCC, or GGC) appended to the 3' end. In some embodiments, the number of CGG repeats or permutations in the primer is four or five. In some embodiments, the primer contains a sequence of CGG repeats (or permutations thereof) stretching for 12-15 nucleotides or more. In some embodiments, the primer contains sequence of CGG repeats (or permutations thereof) ranging from 3 to 10 repeats. The primer may contain 3, 4, 5, 6, 7, 8, 9, or 10 repeats, and optionally an additional partial repeat of 1 or 2 C and/or G residues.

In some embodiments, the primer that anneals to the repeat region or GC rich region has a preferential binding activity for sites in the region comprising an interrupter element. Preferential binding to site of an interrupter element can result in selective amplification of at least one product comprising the interrupter element, e.g., by using the primer in a PCR reaction with an oppositely oriented second primer that binds outside of the repeat or GC rich region. Preferential binding activity can be specific, for example, for sites comprising CGG and AGG elements, or the permutations and/or reverse complements thereof, such as a site comprising (1) one AGG element or a part of an AGG element comprising an A, and (2) three, four, five, or six CGG elements and optionally an additional partial CGG element.

In some embodiments, the primer that anneals to a repeat region or a GC rich region and binds preferentially to a site or sites comprising an interrupter element may comprise an A, T, or U residue within or at the end of the part of the primer that anneals to repeat or GC rich sequences. For example, the primer can have an A, T, or U among or at the end of a stretch of CGG, CCG, GCG, CGC, GCC, or GGC repeats; see, for example, SEQ ID NOs 44 and 45 above. The A, T, or U residue can occur at the 3' end of the primer. When the A, T, or U residue occurs at the end of the CGG, CCG, GCG, CGC, or GCC, GGC repeats, there may or may not be a partial CGG, CCG, GCG, CGC, GCC, or GGC repeat between the A, T, or U residue and the last complete CGG, CCG, GCG, CGC, GGC, or GGC repeat. It is possible to substitute unnatural nucleotide residues that preferentially base pair with T/U or A residues relative to other natural nucleotide residues for the A, T, or U residue. Likewise, it is also possible to substitute one or more unnatural nucleotide residues that preferentially base pair with C or G residues relative to other natural nucleotide residues for one or more G and/or C residues that make up the CGG, CCG, GCG, CGC, GCC, or GGC repeats. The presence of one or more such unnatural residues within a sequence otherwise made up of CGG, CCG, GCG, CGC, GCC, or GGC repeats (optionally with an A, T, U, or corresponding unnatural residue as discussed above) does not negate the identity of said sequence within the context of the present disclosure as a sequence of CGG, CCG, GCG, CGC, GCC, or GGC repeats. Unnatural nucleotide residues are nucleotide residues comprising a nucleobase other than adenine, thymine, guanine, cytosine, and uracil (A, T, G, C, and U, respectively). Examples of unnatural nucleotide residues that preferentially base pair with A or T/U residues include, without limitation, adducts of T, U, or A residues that preferentially base pair with A or T/U residues relative to other natural residues (e.g., 5-substituted uracil analogs); and residues comprising nucleobases such as, for example, pseudouracil and diaminopurine.

In some embodiments, C9ORF72 parameter information can be generated using a primer that anneals outside of a repeat region and a primer that anneals to repeat sequences, sequence permutations, or reverse complements of the sequences. The primers that can anneal outside of (upstream or downstream) the repeat region may be forward or reverse primers, as appropriate. These sequences may anneal to sequences flanking the repeat region. Examples of a forward primer include TGC GCC TCC GCC GCC GCG GGC GCA GGC ACC GCA ACC GCA (SEQ ID NO: 46). Examples of reverse primers include CGC AGC CTG TAG CAA GCT CTG GAA CTC AGG AGT CG (SEQ ID NO: 47), TGC GCC TCC GCC GCC GCG GGC GCA GGC ACC GCA ACC GCA CCC GGG CCC GGG CCC GG (SEQ ID NO: 48), CGC AGC CTG TAG CAA GCT CTG GAA CTC AGG AGT CGC CGG GGC CGG GGC CGG GG (SEQ ID NO: 49).

In some embodiments, TOMM40 parameter information can be generated using a primer that anneals outside of a repeat region and a primer that anneals to repeat sequences, sequence permutations, or reverse complements of the sequences. The primers that can anneal outsider of (upstream or downstream) of the repeat region may be forward or reverse primers. These sequences may anneal to sequences flanking the repeat region. An example of a forward primer includes CCA AAG CAT TGG GAT TAC TGG C (SEQ ID NO: 50). An example of a reverse primer includes GAT TGC TTG AGC CTA GGC ATT C (SEQ ID NO: 51).

In some embodiments, a first primer is used when generating the ladder of amplification products and has a preferential binding activity for sites in the repeat or GC rich region that do not comprise interrupter elements. The presence of an interrupter element can be signaled in the results of this method by a relatively low level of products whose synthesis would have involved extension of the first primer bound to sites comprising the interrupter element. These low levels can appear as a gap or set of low peaks surrounded by higher peaks in an electropherogram. In some embodiments, a first primer is provided that has a preferential binding activity for sites in the repeat or GC rich region that comprise interrupter elements. The presence of an interrupter element is signaled in an anchored assay by a relatively high level of products whose synthesis involved extension of the first primer bound to sites comprising the interrupter element. The high level can appear as a spike surrounded by lower peaks and/or baseline signal in an electropherogram.

The methods of generating parameter information may relate to amplification reactions comprising providing at least two or at least three different primers. In some embodiments, at least three different primers are provided and one of the primers is a primer that preferentially binds outside the repeat or GC rich region, a second primer preferentially binds within the repeat or GC rich region, and the third primer is a subsequence of either the first or second primer. In some embodiments, one primer is a chimeric primer comprising CGG repeats and a 5' flap sequence, and another primer has the sequence of the 5' flap sequence of the chimeric primer. It should be noted that the primer having the sequence of the 5' flap sequence of the chimeric primer can, but does not necessarily, have the entire non-repeat sequence of the chimeric primer. In other words, the sequence of part or all of one primer can be comprised by the sequence of another primer; for example, the chimeric primer comprises a 5' flap sequence, and another primer can comprise the sequence of part or all of the 5' flap. In some embodiments, the primer contains 12-15 nucleotides of a CGG repeat sequence. The 5' flap sequence may correspond to a sequence adjacent to or near to the CGG repeat region or it may be unrelated to sequences in and around the CGG repeat region. In some embodiments, the length of the chimeric primer may be approximately 35, 40, 45, 50, or 55 nucleotides. In some embodiments, one or more of the primers has a melting temperature ranging from 60° C. to 75° C., for example, approximately 60° C., 65° C., 70° C., or 75° C.

In some embodiments, at least three different primers are provided and one primer is provided at a concentration lower than the concentration of another primer. For example, the chimeric primer is optionally provided at a lower concentration than the primer with the sequence of the 5' flap sequence of the chimeric primer. The ratio of concentrations, expressed as a fold difference, may range from 2 to 10,000 or more, for example, 10, 20, 50, 100, 200, 500, 1,000, 2,000, 5,000, or 10,000 (or any value in between). In such embodiments, the primer present at a lower concentration can be depleted in early rounds of the amplification reaction, such that extension is generally all, or nearly all, from the primers still present (which were initially present at relatively higher concentrations).

In some embodiments, the methods of generating parameter information comprise providing dNTPs in a GC/AT ratio greater than one, and at a total dNTP concentration conducive to synthesis of DNA comprising repeat or GC-rich templates. See U.S. Publication No. 2010-0209970. The GC/AT ratio may be about 1.1, 1.2, 1.4, 1.6, 2, 2.5, 3, 4, 5, 6, 7, 8, 9, 10, 11, 12, 13, 14, 15, 16, 17, 18, 19, 20, 25, or higher. The GC/AT ratio may be between 1.1 and 20, 1.1 and 15, 1.1 and 10, 1.1 and 8, 1 and 15, 1.1 and 7, 1.1 and 6, 1.1 and 5, 1.2 and 25, 1.4 and 25, 1.6 and 25, 2 and 25, 3 and 25, 4 and 25, 5 and 25, 2 and 15, 2.5 and 10, or 4 and 10. The total dNTP concentration may be about 0.4, 0.5, 0.6, 0.7, 0.8, 0.9, 1, 1.2, 1.5, 2, or 3 mM. The dNTP concentration may be between 0.4 and 3 mM, 0.5 and 3 mM, 0.6 and 3 mM, 0.7 and 3 mM, 0.8 and 3 mM, 0.9 and 3 mM, 1 and 3 mM, 0.4 and 2 mM, 0.4 and 1.5 mM, 0.4 and 1.2 mM, 0.4 and 1 mM, 0.4 and 0.9 mM, 0.4 and 0.8 mM, 0.4 and 0.7 mM, 0.5 and 2 mM, 0.5 and 1 mM, or 0.6 and 0.9 mM. "GC/AT Ratio" means the ratio of the concentration of the sum of dCTP, dGTP, and all nucleotide analogs thereof, to the concentration of the sum of dATP, dTTP, dUTP, and all nucleotide analogs thereof, in a given solution or mixture. "dNTP" stands for deoxynucleotide triphosphate and refers to dATP, dCTP, dGTP, dTTP, dUTP, and analogs thereof. "Nucleotide analogs" are molecules or ions comprising a base moiety other than the natural bases adenine (A), cytosine (C), guanine (G), thymine (T), or uracil (U), a sugar moiety identical or similar to deoxyribose, and at least one phosphate or multiple phosphate (e.g., diphosphate or triphosphate) moiety. The nucleotide analog is an analog of a specific nucleotide, in particular dATP, dCTP, dGTP, dTTP, or dUTP, when it comprises a triphosphate and a sugar moiety, the structure and configuration of both of which are suitable for incorporation into a nucleic acid double helix by a polymerase, and a base whose base pairing properties in a nucleic acid double helix and loci of incorporation by DNA polymerases in a nucleic acid double helix are most similar to one of the five previously listed nucleotides, with the exception that analogs of dTTP will generally also be analogs of dUTP and vice versa. The term "analog" used in conjunction with terms including but not limited to "nucleoside", "base", "nucleobase", or "residue" is to be interpreted in the same manner as if it were used in conjunction with "nucleotide."

In some embodiments, the methods of generating parameter information can further comprise providing buffers for the PCR amplification reactions. The buffers may comprise, for example and without limitation, tris(hydroxymethyl) aminomethane (Tris), bis-tris propane, bicarbonate, phosphate, glycine, histidine, 4-(2-hydroxyethyl)-1-piperazineethanesulfonic acid (HEPES), 3-(N-morpholino) propanesulfonic acid (MOPS), and various conjugate bases/acids and salts thereof.

In some embodiments, the methods of generating parameter information can comprise providing at least one DNA polymerase to synthesize DNA from dNTPs in a template dependent manner. The DNA polymerase may comprise a wild-type, modified, thermophilic, chimeric, engineered, and/or a mixture of more than one polymerase. The DNA polymerase may comprise Exact Polymerase (5 PRIME GmbH), AccuSure™ DNA Polymerase (Bioline), Phusion™ AccuPrime™ Pfx (Invitrogen), Platinum Taq DNA Polymerase High Fidelity (Invitrogen), Phire™ Hot Start DNA Polymerase (New England Biolabs), Phusion® Hot Start High-Fidelity DNA Polymerase (New England Biolabs), JumpStart™ REDTaq™ DNA Polymerase (Sigma-Aldrich), PfuUltra™ Hotstart DNA Polymerase (Stratagene), PfuTurbo® Cx Hotstart DNA Polymerase (Stratagene), PrimeSTAR™ HS DNA Polymerase (Takara), Extensor Hi-Fidelity PCR Enzyme (ABgene), ACCUZYME™ DNA Polymerase (Bioline), SAHARA™ DNA Polymerase (Bioline), VELOCITY DNA Polymerase (Bioline), GeneChoice® AccuPOL™ DNA Polymerase (GeneChoice, Inc.), GeneChoice® UniPOL™ DNA Polymerase (GeneChoice, Inc.), Elongase Enzyme Mix (Invitrogen), Pfx50™ DNA Polymerase (Invitrogen), Phusion DNA Polymerase (New England Biolabs), KOD HiFi DNA Polymerase (Novagen), KOD XL DNA Polymerase (Novagen), Expand 20 kb PLUS Thermostable DNA polymerase mixture (Roche Applied Science), Expand High Fidelity PLUS Thermostable DNA polymerase mixture (Roche Applied Science), Expand High Fidelity Thermostable DNA polymerase mixture (Roche Applied Science), Expand Long Template Thermostable DNA polymerase mixture (Roche Applied Science), Easy-ATM High-Fidelity PCR Cloning Enzyme (Stratagene), EXL™ DNA Polymerase (Stratagene), Herculase® Enhanced DNA Polymerase (Stratagene), Herculase® II Fusion DNA Polymerase (Stratagene), Kapa LongRange™ DNA Polymerase (Kapa Biosystems), Kapa HiFi™ DNA Polymerase (Kapa Biosystems), Kapa2G™ Robust DNA Polymerase (Kapa Biosystems), Kapa2G™ Robust HotStart DNA Polymerase (Kapa Biosystems), Kapa2G™ Fast DNA Polymerase (Kapa Biosystems), Kapa2G™ Fast HotStart DNA Polymerase (Kapa Biosystems), LA TAQ DNA Polymerase (Takara), Optimase DNA Polymerase (Transgenomic, Inc.), Exo-Pfu DNA Polymerase (Stratagene), HotMaster Taq DNA Polymerase (5 PRIME GmbH), HotTaq DNA Polymerase (Abnova Corporation), AmpliTaq Gold® DNA Polymerase (Applied Biosystems), Bst DNA Polymerase Lg Frag (New England Biolabs), MasterAmp™ Tfl DNA Polymerase (EPICENTRE Biotechnologies), Red Hot DNA Polymerase (ABgene), Thermoprime Plus DNA Polymerase (ABgene), Taqred DNA Polymerase (AppliChem GmbH), BIO-X-ACT™ Long DNA Polymerase (Bioline), BIO-X-ACT™ Short DNA Polymerase (Bioline), Bioline HybriPol™ DNA Polymerase (Bioline), BioTherm Taq DNA Polymerase (eEnzyme LLC), EU-Taq DNA Polymerase (eEnzyme LLC), Synergy Taq DNA Polymerase (eEnzyme LLC), GeneChoice® RedPOL™ DNA Polymerase (GeneChoice, Inc.), AccuPrime™ GC-Rich DNA Polymerase (Invitrogen), PyroPhage® 3173 DNA Polymerase, Exo Minus (Lucigen), 9 Degrees North (Modified) DNA Polymerase (New England Biolabs), Therminator DNA Polymerase (New England Biolabs), Pwo DNA Polymerase (Roche Applied Science), Pag5000™ DNA Polymerase (Stratagene), YieldAce™ DNA Polymerase (Stratagene), e2TAK™ DNA Polymerase (Takara), or naturally occurring DNA polymerases from *P. kodakaraensis, P. furiosus, T. gorgonarius, T. zilligii, T. litoralis* "Vent™", P. GB-D "Deep Vent", T. 9N-7, *T. aggregans, T. barossii, T. fumicolans, T. celer, Pyrococcus* sp. strain ST700, *T. pacificus, P. abysii, T. profundus, T. siculi, T. hydrothermalis, Thermococcus* sp. strain GE8, *T. thioreducens, P. horikoshii* or *T. onnurineus* NA1, *Thermococcus* sp. 9° N-7, *Thermococcus* sp. GI-J, *Thermococcus* sp. MAR-13, *Thermococcus* sp. GB-C, *Thermococcus* sp. GI-H, *Thermus aquaticus, Thermus thermophilus, Thermus caldophilus, Thermus filiformis, Thermus flavus, Thermotoga maritima, Bacillus stearothermophilus,* or *Bacillus caldotenax.*

In some embodiments, at least one of the primers comprises a radiologically or electromagnetically detectable moiety. Radiologically detectable moieties include radioactive isotopes that emit detectable particles, such as beta or gamma particles, for example, $^{14}C$, $^{3}H$, $^{32}P$, $^{33}P$, $^{35}S$, and $^{125}I$. Electromagnetically detectable moieties include chemical entities that interact with electromagnetic radiation (including absorbance, emission, or both) in a detectable way, such as chromophores and fluorophores, for example, fluorescein, FAM, cyanine dyes, rhodamine dyes, etc. Exemplary fluorophores include FAM™ (fluorescein), HEX™, TET™, JOE™, VIC®, NED™, PET®, ROX™, TAMRA™, and Texas Red®.

In another example, repeat region sizing and genotype reconstruction to characterize the A/T-rich segment loci of TOMM40 or fragments thereof can be generated using methods described in U.S. Provisional Application No. 62/196,239, including the primers, polymerase, reagents, and reaction conditions are incorporated by reference.

II. Ladder of Amplification Products

In various embodiments, the amplification products (also referred to herein as amplification fragments) generated from an amplification of a nucleic acid of interest (or a portion of that nucleic acid comprising a repeat region) is subjected to electrophoresis, preferably capillary electrophoresis, and the size of the repeat region is determined using a ladder of amplified products generated by the electrophoresis. In some embodiments, the ladder of amplified products is used as an internal standard on its own to determine the repeat region length. The internal standard may be calculated from the ladder of amplification products, for example using internal sizing ladder calibration. In other embodiments, a ladder of amplified products is used as an internal standard to determine the size of a nucleic acid and in combination with an external standard. In certain embodiments, the external standard may be calculated using external sizing ladder calibration. In additional embodiments, the internal sizing ladder calibration (ladder of amplified products) may be used in combination with external sizing ladder calibration (external standard). As described in detail below, the goodness-of-fit of the internal standard, the goodness-of-fit of the external standard, and the consistency between the internal standard and the external standard may also be used for sample quality control.

In methods provided herein, a ladder of amplification products can be obtained by amplifying a region of a nucleic acid comprising a repeat region and performing a high resolution fragment analysis method, such as capillary electrophoresis. In some embodiments, electrophoresis (e.g., capillary electrophoresis) can distinguish amplification products differing by only one repeat unit (e.g., in a CGG repeat region, amplification products differing by only 3 nucleotides can be distinguished). In some embodiments, the repeat unit is 1, 2, 3, 4, 5, 6, 7, 8, 9, 10, 11, 12, 13, 14, 15, 16, 17, 18, 19, 20 or more nucleotides in length. In some embodiments, the repeat unit is 2 nucleotides in length. In some embodiments, the repeat unit is 3 nucleotides in length. In some embodiments, the repeat unit is 6 nucleotides in length. In some embodiments, electrophoresis can distinguish amplification products of three nucleotides or fewer. In some embodiments, electrophoresis can distinguish amplification products of one bp. In some embodiments, the repeat region is a homopolymeric segment and electrophoresis distinguishes amplification products differing by one nucleotide in length.

In various embodiments, a repeat profile is generated from the ladder of amplification products produced by the electrophoresis. In some embodiments, the repeat profile is used in sizing, e.g., sizing the repeat region or any other region of interest in the nucleic acid being evaluated in a patient sample. In some cases the repeat profile includes detecting the beginning of the repeat signal. In yet other embodiments, the repeat profile includes a start length in the electropherogram. In additional embodiments, the repeat profile includes a repeat number.

In various embodiments, the algorithm for repeat peak identification works in several stages. In certain embodiments, the beginning of the repeat signal is first detected using information about the window in which the repeat signal starts based on the sampling frequency of the instrument. In other embodiments, quantile-based analysis is then used to determine the range in which the repeat signal starts and ends. In some embodiments, a frequency-based analysis is used to determine repeat periodicity in sampling units. In certain embodiments, the repeat periodicity is used to inform the window size for which repeat peaks will be called. In other embodiments, a quantile-based approach is used to derive a threshold at which repeat peaks should be called. In some embodiments, a sliding window is used to call single repeat peaks, where the called peaks for each window are defined as having a negative second-order derivative with the largest magnitude in the range. In certain embodiments, if no peaks are found or the signal falls below the threshold where the repeat periodicity is used to inform the window size for which repeat peaks will be called, the location of the repeat peak at the center of the window may be extrapolated. In certain embodiments, as peaks are called, the size of the window based on the difference between repeat peaks in sampling units may be adjusted.

In various embodiments, the algorithm for repeat peak identification works by first detecting the beginning of the repeat signal using information about the window in which the repeat signal starts based on the sampling frequency of the instrument. In certain embodiments, the algorithm for peak identification first works by detecting the beginning of the repeat signal using information about the window in which the repeat signal starts based on the sampling frequency of the instrument and secondly using quantile-based analysis to determine the range in which the repeat signal starts and stops. In other embodiments, the algorithm for peak identification first works by detecting the beginning of the repeat signal using information about the window in which the repeat signal starts based on the sampling frequency of the instrument; second, using quantile-based analysis to determine the range in which the repeat signal starts and stops; and third, using frequency-based analysis to determine repeat periodicity in sampling units. In some embodiments, the algorithm for peak identification first works by detecting the beginning of the repeat signal using information about the window in which the repeat signal starts based on the sampling frequency of the instrument; second, using quantile-based analysis to determine the range in which the repeat signal starts and stops; third, using frequency-based analysis to determine repeat periodicity in sampling units; and fourth, using the repeat periodicity to inform the window size for which repeat peaks will be called. In certain embodiments, the algorithm for peak identification first works by detecting the beginning of the repeat signal using information about the window in which the repeat signal starts based on the sampling frequency of the instrument; second, using quantile-based analysis to determine the range in which the repeat signal starts and stops; third, using frequency-based analysis to determine repeat periodicity in sampling units; fourth, using the repeat periodicity to inform the window size for which repeat peaks will be called; and fifth, using a quantile based approach to derive a threshold at which repeat peaks will be called. In some embodiments, the algorithm for peak identification first works by detecting the beginning of the repeat signal using information about the window in which the repeat signal starts based on the sampling frequency of the instrument; second, using quantile-based analysis to determine the range in which the repeat signal starts and stops; third, using frequency-based analysis to determine repeat periodicity in sampling units; fourth, using the repeat periodicity to inform the window size for which repeat peaks will be called; fifth, using a quantile based approach to derive a threshold at which repeat peaks will be called; and sixth, using a sliding window to call single repeat peaks, where the called peaks for each window are defined as having a negative second-order derivative with the largest magnitude in the range. In some embodiments, if no peaks are found or the signal falls below the threshold determined in the fourth stage, the location of the repeat peak as the center of the window may be extrapolated. In other embodiments, as peaks are called, the size of the window based on the difference between repeat peaks in sampling units may be adjusted.

In certain embodiments, a repeat element periodicity is determined. In other embodiments, the repeat element size is determined using a frequency-based analysis, such as Fourier Transform analysis. In some embodiments, the methods include converting from the instrument sampling domain, to the base-pair repeat domain. In other embodiments, the information is used to determine the size of each amplification product in the ladder of amplification products. In some embodiments, the information derived from determining the length in nucleotides of the repeat elements in the ladder is used to generate a calibration curve to determine the size of the repeat region. In more specific embodiments, the repeat region capillary electrophoresis is normalized against a ladder of amplification products to size the repeat region. In certain embodiments, the entire repeat profile is used for generating a calibration curve. In other embodiments, peaks are selected for use in a calibration curve, for example based on peak height and/or peak shape. In yet other embodiments, peaks are selected based on qualities of the consistency of repeat profile periodicity. In additional embodiments, consistency of repeat profile periodicity is determined by applying a threshold to a transformed version of the repeat peak location signal, for example as an entropy filter or a frequency filter.

In certain embodiments, annotating device 130 may be configured to use the entire repeat profile to generating a sizing standard. In various embodiments, annotating device 130 may select peaks for generating a sizing standard based on peak characteristics. The peak characteristics may be peak height and/or peak shape. In various embodiments, annotating device 130 may select peaks for generating a sizing standard based on repeat profile periodicity characteristics, such as the consistency of the repeat profile periodicity. For example, consistency of repeat profile periodicity may be determined by annotating device 130 by applying a threshold to a transformed version of the repeat peak location signal, either as an entropy filter on differences between peaks, or as a frequency filter.

In certain embodiments, a repeat element periodicity reflects the frequency of the repeating motif or repeating sequence, for example, a repeat element periodicity is three base pairs for the FMR1 genetic loci. A repeat element periodicity may be one, two, three, four, five, or six or more depending on the repeat length in the genetic locus. In certain embodiments, a first amplification product is the length of the shortest amplified product in the set of amplification products within a ladder. In certain embodiments, the amplification product count is the number of different length products. In certain embodiments, the amplification number count can be corrected in accordance with the expected periodicity. In certain embodiments, the constant element length for each template is a fixed fragment determined by the primer and the template.

In further embodiments, the methods involve correcting for a signal artifact. Such signal artifacts can include contaminating peaks, missing peaks, air bubbles, flare up signals, or bleed-through of signal from other fluorescent channels.

One of skill in the art would readily recognize that sizing of the repeat region involves use of the ladder of amplification products for sizing instead of an external standard in various embodiments.

In various embodiments, additional parameter information is obtained from the electrophoresis electropherogram, such as the distance in the forward and reverse directions to any interruptions in the repeat region. In some embodiments, the repeat region size, combined with the additional parameter information, is used to reconstruct a genotype. In some embodiments, the reconstruction is done on an apparatus running a machine readable medium that evaluates all potential genotypes satisfying some of the parameter information and identifies a solution genotype satisfying all the parameter information. In some embodiments, the apparatus, method, and machine readable medium for this automated reconstruction of a genotype are those described in International Publication No. WO/2014/015273, which is incorporated by reference in its entirety.

III. Automated Sizing Analysis

In various embodiments, a method for automated sizing of the repeat region is provided. In some embodiments, the automated sizing of the repeat region first identifies and defines repeat primer peaks and gene-specific primer peaks in the sample. In certain embodiments, peak shape, peak magnitude, or distance between peaks in a local window are considered. In other embodiments, a standard curve may be generated using at least 3 of the repeat primer peaks. In more specific embodiments, a standard curve may be generated with all of the repeat primer peaks. In certain embodiments, a standard curve is generated using all the repeat primer peaks by determining the value for a set of variables. In some embodiments, the variables may include, but are not limited to, for example, repeat element size, base pairs preceding the first peak, the number of repeat elements in a repeat primer minus one multiplied by repeat element size, peak count, and the constant element length used for complimentary priming. In certain embodiments, a standard curve is generated by determining the value for the following variables: —Z=repeat element size (in bp), —X=base pairs preceding the first peak (X=[number of repeat elements in RP primer−1]*Z), —N=peak count (sum peaks from 1-to-N) and Anc=the constant element length used for complimentary priming (in bp). In more specific embodiments, a standard curve is generated using a 30CGG repeat normal male. In some embodiments, using a 30CGG repeat male, the following variables are calculated: —Z=repeat element size (in bp) (For AmplideX FMR1: 3 bp repeat), —X=base pairs preceding first peak, X=[number of repeat elements in RP primer−1] (for AmplideX FMR1: X=[5XCGGs−1]*3=12 bp), —N=peak count (sum peaks from 1-to-N) (for the last peak in a 30CGG normal FXS male sample N=26 (26 stutter peaks present)), —Anc=the constant element length used for complimentary priming (in bp) (for AmplideX FMR1 example. Constant element length is 127 bp). In some embodiments, once the standard curve has been generated, the automated process calculates the exact size of each n peak in the stutter pattern: e.g., size (bp) for the N peak=[X+ZN+Anc]. In certain embodiments, the automated process accounts for sequence interruptions to the repeat profile by extrapolating the gap (in bp)+X to the overall size. For example, for FMR1 and AGG interruption: =3 bp+12 bp=15 bp. In certain embodiments, the automated process creates a calibration curve from the repeat primer peaks by plotting the observed CE sizes for peaks (or their timestamp) vs. calculated size (as described above) and used the derived linear regression function for gene-specific size calculations.

In certain embodiments, the sizing standard may be used to generate sizes for fragments within the repeat profile. In other embodiments, the sizing curve may be used to generate sizes of fragments outside of the repeat region by extrapolation.

In certain embodiments, Repeat Primed-PCR (RP-PCR) may be used for repeat region assessment. RP-PCR may use a degenerate primer to generate a multitude of repeat fragments, consistent with a genotype. Some embodiments using RP-PCR may circumvent sizing and use direct counting of stutter peaks as a method for repeat assessment. This direct counting may use the formula: r (repeat region count) a=N+X/Z. For example, for FMR1, 26+12/3=30CGGs.

In various embodiments, the method can be conducted using an apparatus comprising a processor (e.g., a computer) programmed to conduct sizing analysis. In some embodiments, the processor is programmed to receive information (parameter information) regarding a nucleic acid and then reconstruct a solution genotype for the nucleic acid. In some embodiments, the parameter information is repeat region size information. In some embodiments, the parameter information can further comprise the distance in the forward and reverse directions to any interruptions in the repeat region. In some embodiments, the repeat region size and optionally the distance in the forward and reverse directions to any interruptions are used by the apparatus for automated reconstruction of a genotype. In some embodiments, the apparatus also comprises a monitor to display input information and/or the solution genotype. In some embodiments, the solution genotype is stored electronically on the apparatus, and/or is capable of being printed for further diagnostic or therapeutic uses.

As described in more detail in the examples below, the method can be used, in some embodiments, to size a genotype of the CGG repeat region in the FMR1 gene. The 5' UTR of FMR1 can comprise one or more CGG repeat regions, each of which may contain one or more AGG interruptions within the region. Where more than one AGG interruption is present, these generally do not occur contiguously (i.e., it is rare to find a CGG repeat region comprising $(AGG)_n$, where n is greater than or equal to 2).

IV. Samples

Various samples containing a nucleic acid of interest can be used in the disclosed methods of sizing a repeat region or a nucleic acid. In various embodiments, a sample is obtained from a human or non-human animal. For example, the sample may be a patient sample. A "patient sample" is any biological specimen from a patient. The term sample includes, but is not limited to, biological fluids such as blood, serum, plasma, urine, cerebrospinal fluid, tears, saliva, lymph, dialysis fluid, lavage fluid, semen, and/or other liquid samples, as well as cells and tissues of biological origin. Cells and tissues may include buccal cells, mouthwash collections, or skin cells, including hair follicles. The term also includes cells isolated from a human or cells derived therefrom, including cells in culture, cell supernatants, and cell lysates. It further includes organ or tissue culture-derived fluids, tissue biopsy samples, tumor biopsy samples, stool samples, and fluids extracted from physiological tissues, as well as cells dissociated from solid tissues, tissue sections, and cell lysates. It may also include post-mortem solid tissue samples, such as those from the brain. The term sample also includes any other cellular or non-cellular specimen obtained from a human or non-human animal that comprises a nucleic acid of interest. In some embodiments, the sample contains less than about 80, 100, 150, 200, 500, 1,000, 1,500, 2,000, 2,500, 3,000, 4,000, or 5,000 ng of the nucleic acid of interest.

In some instances, the sample includes one or more nucleic acids of interest. The nucleic acid of interest can be genomic DNA. The genomic DNA or other nucleic acid of interest may be separated from other DNA and non-DNA components of the sample before being subjected to the methods of the invention. Many methods of DNA purification and separation are known in the art and may be used with the disclosed methods. In some embodiments, the nucleic acid of interest can comprise nucleic acid synthesized in vitro. Examples of in vitro nucleic acid synthesis include an amplification reaction such as PCR, in vitro transcription, in vitro reverse transcription, in vitro primer extension, a sequencing reaction, phosphoramidite-based nucleic acid synthesis, and combinations thereof.

In some embodiments, the nucleic acid of interest in the sample may comprise a repeat region, for example one or more repeating GC-rich segments. In certain embodiments, the nucleic acid of interest in the sample may comprise the FMR1 and/or FMR2 genes or fragments thereof, or at least part of the 5' UTR of FMR1 and/or FMR2 (e.g., a portion that comprises the CGG repeats of the 5' UTR of FMR1 or the CCG repeats in the 5' UTR of FMR2). In certain embodiments, the size of the nucleic acid may be about 50, 100, 200, 300, 500, or 700 bp, or 1, 1.5, 2, 2.5, 3, 4, 5, 7, or 10 kb, or any value in between. In some embodiments, the size of the nucleic acid may be between 50 bp and 10 kb, 100 bp and 10 kb, 200 bp and 10 kb, 300 bp and 10 kb, 500 bp and 10 kb, 700 bp and 10 kb, 1 kb and 10 kb, 1.5 bp and 10 kb, 2 bp and 10 kb, 3 by and 10 kb, 50 by and 7 kb, 50 by and 5 kb, 50 by and 4 kb, 50 by and 3 kb, 50 by and 2 kb, 50 bp and 1.5 kb, 100 bp and 7 kb, 200 bp and 5 kb, or 300 bp and 4 kb.

In various embodiments, the nucleic acid of interest in the sample may comprise one or more repeating A/T-rich segments, such as a homopolymeric segment. In certain embodiments, the A/T-rich segment is: (i) a homopolymeric segment comprising at least 10 A residues, at least 10 T residues, or at least 10 U residues, wherein the at least 10 A, T, or U residues are consecutive or interrupted once by one to three other nucleotides; or (ii) a segment comprising $(T_nA)_m$, $(AT_n)_m$, $(TA_n)_m$, or $(A_nT)_m$, wherein n is 2 or greater and m is such that the length of the repeating A/T-rich segment is 10 or more residues. In some embodiments, the nucleic acid template can be known to comprise one or more repeating A/T-rich segments, such as homopolymeric segments. The nucleic acid template can be suspected of comprising one or more repeating A/T-rich segments such as homopolymeric segments. In certain embodiments, the size of the nucleic acid may be about 50, 100, 200, 300, 500, or 700 bp, or 1, 1.5, 2, 2.5, 3, 4, 5, 7, or 10 kb, or any value in between. In some embodiments, the size of the nucleic acid may be between 50 bp and 10 kb, 100 bp and 10 kb, 200 bp and 10 kb, 300 bp and 10 kb, 500 bp and 10 kb, 700 bp and 10 kb, 1 kb and 10 kb, 1.5 bp and 10 kb, 2 bp and 10 kb, 3 bp and 10 kb, 50 bp and 7 kb, 50 bp and 5 kb, 50 bp and 4 kb, 50 bp and 3 kb, 50 bp and 2 kb, 50 bp and 1.5 kb, 100 bp and 7 kb, 200 bp and 5 kb, or 300 bp and 4 kb.

In various embodiments, a multiplex assay can be used for parallel analysis of more than one nucleic acid region. In some embodiments, a multiplex PCR-reaction can be used to size at least one repeat region of a nucleic acid. In certain embodiments, a first and second nucleic acid region are amplified. In specific embodiments, a second nucleic acid region is amplified. In other embodiments, a first, a second and a third nucleic acid region are amplified. In other embodiments, a second, and a third nucleic acid region are amplified. In yet other embodiments, a second nucleic acid and optionally a third nucleic acid region are amplified. In certain embodiments, the nucleic acid region is distinct from the template for the ladder amplification products. In some embodiments, at least one nucleic acid region, at least two nucleic acid regions, at least three nucleic acid regions, at least four nucleic acid regions or at least five nucleic acid regions are amplified. In some embodiments, the multiplex assay can be used to size two or more genetic loci. In some embodiments, the multiplex assay can be used to size three or more genetic loci. In some embodiments, the multiplex assay can be used to size at least one repeat region of FMR1 and FMR2. In other embodiments, the multiplex assay can be used to size at least one repeat region of FMR1 and C9ORF72. In some embodiments, the multiplex assay can be used to size at least one repeat region of FMR2 and C9ORF72. In certain embodiments, the multiplex assay can be used to size at least one repeat region of FMR2 and C9ORF72. In other embodiments, the multiplex assay can be used for disorders associated with an expanded repeat region, for example spinocerebellar ataxia, myotonic dystrophy or Huntington's disease. In certain embodiments, the multiplex assay can be used with two or more fluorescent labels.

V. Repeat Region Sizing Apparatus and Machine-Readable Medium

In various embodiments, an apparatus is disclosed for the use in sizing one or more repeat regions and optionally in the reconstruction of a genotype for a nucleic acid containing the repeat region. In some embodiments, information regarding the size or characteristics of a nucleic acid repeat region is provided to the apparatus for use in reconstructing a genotype. In some embodiments, the repeat region also comprises interruptions, e.g., AGG interruptions in a CGG repeat region. In some embodiments, parameter information including repeat region size and distance in the forward and reverse directions to any interruptions is provided to the apparatus for use in reconstructing a genotype.

In various embodiments, an apparatus is disclosed to size a repeat region of a nucleic acid sample and optionally to generate a reconstructed genotype, for example. In some embodiments, the apparatus comprises a processor communicatively coupled to a memory device. In some embodiments, machine-executable instructions are stored on the memory device that, when executed by the processor, cause the processor to conduct repeat region sizing and genotype reconstruction analysis. In certain embodiments, the machine-executable instructions cause the processor to (a) amplifying the repeat region; (b) performing high resolution fragment analysis (c) obtaining a ladder of amplification products; and (d) using the ladder of amplification products as an internal standard to determine repeat region length. In certain embodiments, the apparatus further comprises a monitor communicatively coupled to the processor and memory device, wherein the machine-executable instructions stored on the memory device instruct the processor to display the solution genotype on the monitor. In some embodiments, the apparatus further comprises a printer communicatively coupled to the processor and memory device, wherein the machine-executable instructions stored on the memory device instruct the processor to print the solution genotype on the printer.

In various embodiments, the apparatus used to size a repeat region is capable of accepting the input of parameter information regarding a nucleic acid (e.g., a repeat profile, a repeat element periodicity, a first amplification product, an amplification product count, and/or a constant element length relating to the ladder of amplification products). In some embodiments, the apparatus is programmed to use the parameter information to determine the size of each amplification product in the ladder of amplification products and/or the total size of the nucleic acid. The apparatus can be programmed to display and/or archive the result. In some embodiments, the apparatus comprises a means for displaying and/or archiving the result.

In various embodiments, an apparatus disclosed herein comprises a processor and memory device, wherein the memory device contains machine-readable instructions that instruct the processor to accept the input of parameter information regarding a nucleic acid and conduct sizing analysis, which can be represented by the formula to generate a standard curve: —Z=repeat element size (in bp), —X=base pairs preceding first peak, X=[number of repeat elements in repeat primer−1]*Z, —N=peak count (sum peaks from 1-to-N) —Anc=the constant element length used for complimentary priming (in bp). In some embodiments, to determine the exact size of each n peak in the shutter pattern the following formula may be used: size (base pairs) for the N peak=[X+ZN+Anc]. As a result, this formula provides the size of the repeat region.

In some embodiments, the apparatus further comprises a means to display the solution genotype (e.g., a monitor to display the genotype visually, a data storage medium to save the genotype in a digital format, and/or a connection for transmitting the solution genotype to a printer or other electronic storage or display device).

In some embodiments, the apparatus is a computer, wherein the computer comprises a processor and a memory device having computer code stored on it, wherein the computer code instructs the processor to accept the input of parameter information regarding a nucleic acid and then determine a repeat profile of the ladder of amplification products, and thereby size the repeat region. In some embodiments, the computer also comprises a monitor to display input information and/or the reconstructed genotype. In some embodiments, the reconstructed genotype is stored electronically on the computer and/or is capable of being printed for further diagnostic or therapeutic uses. In various embodiments, the computer comprises a device to allow for user interaction. For example, the computer may comprise a keyboard and/or pointing device (e.g., a mouse or a trackball) that allows a user (such as a patient, doctor, or other healthcare worker) to enter parameter information and/or to access and manipulate the reconstructed genotype.

In various embodiments, the instructions to conduct sizing of a repeat region and optional reconstruction of a genotype may be stored on an apparatus in a machine-readable medium (e.g., machine-executable instructions, software, computer code, computer programs, etc.). For example, the machine-readable medium can comprise computer code stored in C++, C#, Java, Perl, Python, Julia, R, Go, Ruby, Scala, Javascript or any other suitable format for computer code. The machine-readable medium can provide instructions to the apparatus for conducting sizing of a repeat region using parameter information regarding a nucleic acid. In various embodiments, the instructions on the machine-readable medium can instruct an apparatus to (a) amplifying the repeat region; (b) performing high resolution fragment analysis; (c) obtaining a ladder of amplification products; and (d) using the ladder of amplification products as an internal standard to determine repeat region length.

In some embodiments, the instructions on the machine-readable medium instruct the apparatus to display the size result on a monitor. In some embodiments, the instructions on the machine-readable medium instruct the apparatus to print the size result on a printer.

The instructions stored on a machine-readable medium can be any codes, symbols, or other signals that provide instructions, information, and/or data that can be used by an apparatus (e.g., by a processor in a computer). In some embodiments, the instructions stored on the machine-readable medium encode a program that instructs the apparatus to receive parameter information regarding a nucleic acid, conduct analysis to size the repeat region, and store or transmit the size of the nucleic acid.

In some embodiments, the instructions stored on the machine-readable medium instruct the apparatus to execute a repeat region sizing analysis program. In some embodiments, the program includes instructions to display and/or archive the size of the nucleic acid (e.g., to display the size on a monitor, to save the size to a data storage medium, and/or to transmit the size to a printer or other electronic storage or display device).

In some embodiments, the instructions stored on the machine-readable medium further encode a user interface that provides a graphical display on a monitor. In some embodiments, the interface allows a user to enter parameter information regarding a nucleic acid (e.g., by allowing the user to upload a data file or by allowing the user to enter information into display fields shown on the user interface). In some embodiments, the user interface provides the user with options for analyzing the parameter information, such as various methods for displaying and/or saving the input data and/or size result (e.g., by displaying the data on the user's monitor, sending the data to a specified electronic device or electronic address, printing, and/or saving the data to a particular location).

In various embodiments, a nucleic acid size can be stored as data in a storage medium physically connected to the apparatus (e.g., on an internal memory device such as a hard drive on a computer) and/or stored on a remote storage device that is communicatively connected to the apparatus (e.g., by a wired or wireless intranet or internet connection and the like). In some embodiments, the user interface provides the user with options for automatically storing the size in a particular location, printing the size, and/or sending the size to a specified electronic device or electronic address (e.g., to the email address of the medical professional that requested the nucleic acid size).

VI. Methods of Use

In various embodiments, methods disclosed above can be used to detect an expanded repeat region, for example, a GC-rich region or A/T-rich repeat region, and/or to diagnose a disorder in a patient, or to diagnose a risk of a disorder in offspring of the patient. In some embodiments, the methods can be used to diagnose, diagnose a risk, or treat a genetic disorder associated with a repeat region, comprising, for example, (1) obtaining a sample from a patient; (2) isolating a nucleic acid from the sample that has one or more repeat regions, such as a region comprising CGG or CCG repeats or a repeating A/T-rich segment; (3) amplifying a region of the nucleic acid that has one or more repeat regions; (4) performing capillary electrophoresis; (5) obtaining a ladder of amplification products; (6) using the ladder of amplification products as an internal standard to determine repeat region length. In some embodiments, the method can further comprise detecting any interruptions in the repeat region, and determining the distance in the forward and reverse directions to the interruption. In some embodiments, the repeat region size and optionally the distance in the forward and reverse directions to any interruptions are used to reconstruct a genotype. In some embodiments, the repeat region size and optionally the reconstructed genotype are used to detect an expanded repeat region or to diagnose a genetic disorder associated with an expanded repeat region, for example, a GC-rich or A/T-rich region, such as homopolymeric segments. In some embodiments, the repeat region length and/or reconstructed genotype is used to predict the risk of a genetic disorder in a patient or an offspring of the patient. In some embodiments, the repeat region length and/or reconstructed genotype are used to detect a genetic disorder in a patient. In some embodiments, the repeat region length and/or reconstructed genotype are used to detect a risk of a genetic disorder in offspring of the patient. In certain embodiments, the methods include making a suitable treatment decision based on the repeat region length and/or reconstructed genotype (e.g., providing pregnancy counseling and/or fertility treatment). In some embodiments, the methods include administering a suitable treatment to a patient identified as having a genetic disorder based on the repeat region length and/or reconstructed genotype.

For example, the method can comprise isolating an FMR1 or FMR2 nucleic acid or fragments thereof from a patient sample, amplifying the CGG or CCG-rich repeat region, performing capillary electrophoresis to obtain a ladder of amplification products, and using the ladder of amplification products to determine the CGG or CCG-rich repeat region size in order to diagnose and/or predict the risk of and/or make treatment decisions regarding disorders associated with an expanded FMR1 or FMR2 allele. For instance, a size of greater than 200 CGG or CCG repeats can be used to detect Fragile X syndrome or Fragile X (FRAXE) mental retardation in a patient, or a range of a size of greater than 35-45 CGG or CCG repeats can be used to detect the risk of Fragile X syndrome or Fragile X (FRAXE) mental retardation in offspring of the patient. In some embodiments, the method also comprises detecting the distance in the forward and reverse directions to any interruptions in the CGG or CCG-rich repeat region, reconstructing a genotype for the FMR1 or FMR2 allele using the repeat size and interruption information, and using the reconstructed genotype to detect disorders associated with an expanded FMR1 or FMR2 allele.

Numerous genes and genomic regions comprise repeat regions, including those comprising GC-rich or A/T-rich regions, which are associated with genetic disorders, making them potential diagnostic and therapeutic targets. Accordingly, in various embodiments the methods of sizing a repeat region disclosed herein can be used for these genetic loci and can be used to diagnose, prognose, treat, and/or guide treatment decisions for the associated genetic disorders. In some embodiments, the methods of sizing a repeat region disclosed herein can be used to analyze the FMR1 or FMR2 genes. In some embodiments, these methods can assist in the diagnosis of FXS, FRAXE, FXTAS, FXPOI, and dopamine-responsive Parkinsonism, which are associated with the length of CGG repeat regions in the 5' UTR of FMR1 and CCG repeat regions in the 5' UTR of FMR2. For example, a reconstructed FMR1 genotype having greater than about 45 CGG repeats, and particularly a genotype having greater than about 200 CGG repeats, in the 5' UTR can be used to diagnose FXS and associated disorders, as well as to diagnose the risk of the disorders in offspring of the patient.

In further embodiments, the methods of sizing a repeat region may be used to detect genotypes associated with other disorders of expanded repeat regions, such as spinocerebellar ataxia type 1, spinocerebellar ataxia type 2, spinocerebellar ataxia type 3, spinocerebellar ataxia type 6, spinocerebellar ataxia type 7, spinocerebellar ataxia type 8, Friedrich's ataxia, progressive myoclomus epilepsy, myotonic dystrophy I, myotonic dystrophy II, Huntington's disease, spinobulbar muscular atrophy, Dentatorubropallidoluysian atrophy, spinocerebellar ataxia, amyotrophic lateral sclerosis (ALS), frontotemporal dementia (FTD), and Alzheimer's disease. Genetic loci associated with these conditions are known in the art and include, without limitation, SCA1, SCA2, SCA3, CACNA1A, SCA7, SCA8, X25, CSTB, C9ORF72, DMPK, ZNF9, HTT, AR, ATN1, ATXN1-3, ATXN7, ATXN10, CACNA1A, SCA8, PPP2R2B, CNBP, TBP and TOMM40. See, e.g., *Nat Genet.* 1996 May; 13(1):105-8; *Nat Genet.* 1996 May; 13(1):109-13. Hyperexpansion and/or hypermethylation of the GC-rich and/or repeat regions at these loci are associated with the diseases, and detection of these mutations and expansions using the methods disclosed herein can be used as part of treatments or to guide treatments for the detected conditions. Table 1 shows examples of genetic loci that can be used with the methods disclosed herein, and the relationship between repeat regions in those loci and disease genotypes or phenotypes. In certain embodiments, the methods detect repeat lengths of greater than 20, 30, 35, 40, 50, 100, 110, or 200 repeats within a repeat region allele.

TABLE 1

Genetic loci that may be used with the methods disclosed herein, and the relationship between repeat regions in those loci and disease genotypes or phenotypes.

| Disease | Gene | Repeat number Normal | Repeat number Mutant | Repeat position | Repeat variant |
|---|---|---|---|---|---|
| Fragile X syndrome | FMR1 | (CGG) < 45 | (CGG) > 200 | 5'-UTR | AGG |
| Fragile X (FRAXE) mental retardation | FMR2 | (CCG) < 35 | (CCG) > 200 | 5'-UTR | CTG |
| Myotonic dystrophy | DMPK | (CTG) < 35 | (CTG) > 50 | 3'-UTR | CCG, CTC |
| Spinocerebelllar ataxia type 8 | SCA8 | (CTG) < 40 | (CTG) > 110 | Antisense RNA | CCG, CTA, CTC, CCA or CTT |
| Friedrich's ataxia | X25 | (GAA) < 35 | (GAA) > 100 | Intron 1 | GGA, GAG |
| Spinobulbar muscular atrophy | AR | (CAG) < 30 | (CAG) > 40 | Coding | |
| Huntingdon disease | IT15 | (CAG) < 40 | (CAG) > 40 | Coding | |
| Dentatorubral pallidoluysian atrophy | DRPLA | (CAG) < 35 | (CAG) > 50 | Coding | |
| Spinocerebelllar ataxia type 1 | SCA1 | (CAG) < 40 | (CAG) > 40 | Coding | CAT |
| Spinocerebelllar ataxia type 2 | SCA2 | (CAG) < 30 | (CAG) > 35 | Coding | CAA |

TABLE 1-continued

Genetic loci that may be used with the methods disclosed herein, and the relationship between repeat regions in those loci and disease genotypes or phenotypes.

| Disease | Gene | Repeat number Normal | Mutant | Repeat position | Repeat variant |
|---|---|---|---|---|---|
| Spinocerebelllar ataxia type 3 | SCA3 | (CAG) < 40 | (CAG) > 40 | Coding | |
| Spinocerebelllar ataxia type 6 | CACNA1A | (CAG) < 20 | (CAG) > 20 | Coding | |
| Spinocerebelllar ataxia type 7 | SCA7 | (CAG) < 40 | (CAG) > 40 | Coding | normal allele has no interruption |
| Progressive myoclomus epilepsy type | CSTB | ($C_4GC_4GCG$ (SEQ ID NO: 10)) < 3 | ($C_4GC_4GCG$ (SEQ ID NO: 10)) > 50 | Promoter | |
| Alzheimer's Disease | TOMM40 | | | | |
| Amyotrophic lateral sclerosis and Frontotemporal Dementia | C9ORF72 | (GGGGCC) < 30 | (GGGGCC) > 30 | | |
| Myotopic dystorphy type II | CNBP (ZNF9) | (CCTG) < 26 | (CCTG) > 75 | Intron 1 | |

For example, sizing a repeat region and/or reconstructing a genotype can be used to detect genotypes associated with disorders of SCA1 or SCA2, such as Spinocerebelllar ataxia types 1 and 2, which are associated with expansion of their CAG repeat regions. For example, sizing the repeat region can provide information regarding the total length of one or more CAG repeats in the SCA1 or SCA2 genes, as well as the distance in the forward and reverse directions to the CAT or CAA interruptions in the CAG repeats. Sizing the repeat regions, using the total length of the one or more CAG repeats and either the distance in the forward or reverse direction to any interruptions, can be applied to generate a set of potential genotypes for the SCA1 or SCA2 gene. Sizing the repeat region can be used to detect a mutation or a genotype, or to diagnose or assist in diagnosing, an SCA1 or SCA2 related mutation, genotype, or disorder, as well as to treat and guide treatment decisions for the disorder.

In other embodiments, the methods of sizing a repeat region and/or reconstructing a genotype may be used to detect other disorders associated with expanded repeat regions, such as disorders associated with a repeating A/T-rich segment. In some embodiments, the disorder is a neurodegenerative disease. In some embodiments, the neurodegenerative disease is Alzheimer's disease. The Alzheimer's disease can be late-onset Alzheimer's disease. Other genetic loci associated with a repeating A/T-rich segment are known in the art, for instance the gene TOMM40. In some embodiments, the repeat locus being assessed is all or a portion of intron 6 of TOMM40. In some embodiments, the portion of intron 6 of the TOMM40 gene being assessed contains a poly-T repeat polymorphism (re 10524523).

Automatic Sizing Analysis

Figure 2:
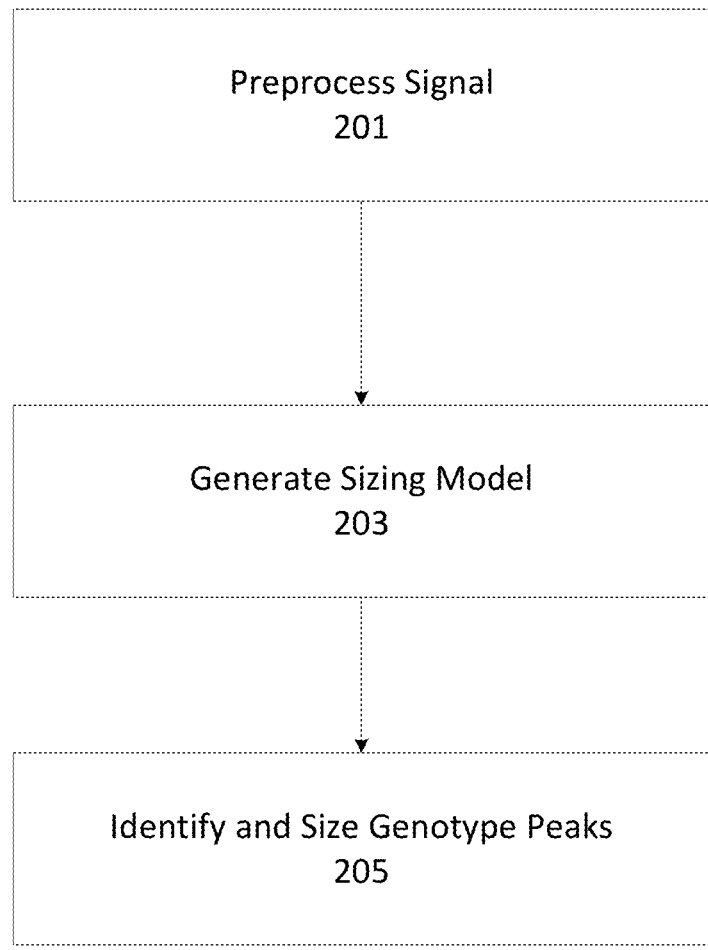
FIG. 2 illustrates an exemplary process for automatically analyzing genomic repeat regions.

FIG. 2 illustrates an exemplary process for automatically analyzing genomic repeat regions. This process may comprise the steps of signal preprocessing 201, generating a sizing standard 203, and gene product sizing 205. As would be appreciated by one of skill in the art, additional steps may be performed, steps may be removed, and the order of the steps may vary without departing from the envisioned embodiments. Annotation device 130 may be configured to perform these steps, consistent with disclosed embodiments.

In step 201, annotation device 130 may be configured to receive and pre-processes raw data. The raw data may be received from CE device 120, or from another device. For example, annotation device 130 may be configured to retrieve the raw data from a storage device. The raw data may be received in data files that store signal intensities for each channel of the CE experiment. These data files may store the signal intensities in a JSON-based format.

In some embodiments, the PCR assay may be run in conjunction with the Applied Biosystems family of Genetic Analyzer instruments (3130/3500/3700), all of which export data in a proprietary format maintained by Applied Biosystems. This format is referred to as the Fragment Sequence Analysis (FSA) format and contains fluorescence data from capillary electrophoresis (CE) experiments, encoded according to a proprietary set of specifications. Annotation device 130 may be configured to directly access this file format. For example, Annotation device 130 may use a parser designed to decode and organize the information in the files into a json-based format for programmatic access and manipulation. This parser may use an open-source module for the perl programming language called Bio::Trace::ABIF (licensed as free software). This parser has been validated on >1000 samples run across different Genetic Analyzer Instruments (3130/3500/3700), and has been shown to be exactly concordant with unprocessed fluorescence data viewed through GeneMapper, the current standard for accessing the FSA format. The output of the parser may comprise data files which may store signal intensities for multiple channels of the CE experiment. These data files may store the signal intensities in a JSON-based format.

At least one channel of the data file may correspond to the ladder of amplification products. This channel may include a repeat profile. In some embodiments, another channel of the data file may correspond to a ladder of products having known sizes. For example, this other channel of the data file may correspond to an external ladder, such as a ROX ladder.

In some embodiments, annotation device 130 may be configured to detect the region of interest in the data file in which the repeat profile exists. Annotation device 130 may dynamically determine the periodicity of the repeat profile using a frequency based analysis. Annotation device 130 may dynamically determine a threshold for calling repeat peaks in the repeat profile. The threshold may be an amplitude threshold. Annotation device 130 may call the repeat peaks in the repeat profile using a sliding window. Annotation device 130 may interpolate repeat peaks in the repeat profile below the threshold. This interpolation may improve the accuracy of the sizing standard generated by annotation device 130. Annotation device 130 may use the estimated starting peak location in the repeat profile and subsequent peak location to generate a sizing standard that maps from sampling units to base pair units.

Preprocessing may normalize the parsed data, adjusting for differences across samples run with different configurations. For example, the PCR assay uses a CE-based readout for data interpretation, and may be subject to convolution by signal artifacts that are systematically present on CE instruments. Each channel of the parsed data may be filtered by annotation device 130 to simplify and increase the robustness of the downstream data processing. In some aspects, a low-pass filter or band-pass filter may be applied to one or more of the channels in order to smooth the data. The low-pass filter may be a Butterworth, Savitzky-Golay, a moving average, or other similar filter. Each channel may be normalized by annotation device 130 to account for improper instrument calibration and/or variability in instrument configuration across labs, as baseline fluorescence values for each channel in an CE device must be continuously calibrated throughout the lifetime of the device. Annotation device 130 may be configured to re-calibrate a channel by subtracting a value from the channel. This value may be a statistic of the signal intensities of the channel. For example, the value may be the $10^{th}$ percentile of signal intensities of the channel. The $10^{th}$ percentile may robustly represents the lower values in the signal, without being affected by commonly encountered sharp negative fluctuations in signal intensity. In the equations below, let $s(x, c)$ represent the signal intensity at location x for the instrument channel c:

$$b(c)=Q_{10}(s(x,c))$$

$$s_{norm}(x,c)=s(x,c)-b(c)$$

Annotation device 130 may be configured to remove artifacts arising from artifacts such as air bubbles or contaminants during signal pre-processing. Air-bubbles present in capillary tubes during a CE experiment may produce large spikes in signal intensity. These spikes may be erroneously interpreted as gene-specific products or ROX channel sizing peaks, producing incorrect results. However, fluorescence from air-bubbles affects all of the channels to a similar degree of magnitude, enabling annotation device 130 to identify and remove air-bubble artifacts.

In a first step, annotation device 130 may be configured to find the locations of all peaks exceeding 50 RFU across all channels in the parsed data. Annotation device 130 may be configured to determine candidate air-bubble artifact locations as the intersection of peak indices occurring across multiple channels. For example, the intersection of peak indices in channels ({FAM, HEX, NED, ROX}) may be represented as follows:

$$C=P(FAM)\cap P(HEX)\cap P(NED)\cap P(ROX)$$

Annotation device 130 may be configured to determine whether an air-bubble artifacts exists at each candidate location. As a first step, annotation device 130 may be configured to identify a window in the channel including a potential air bubble location. In some embodiments, annotation device 130 may be configured to determine left and right shoulders $[h_{il}, h_{ir}]$ of the signal intensity peak at the candidate location. In the equation below, S(i, c) may be a function of the signal intensity between the left and right shoulders for channel c, and i may represent the candidate peak locations.

$$S(i,c)=s([h_{il},h_{ir}],$$

As a second step, annotation device 130 may be configured to determine a correlation between signal intensities across the multiple channels within the window. This correlation may be a pairwise rank correlation significance test or any other measure of similarity comparing signal intensities across channels:

$$PC(i)=\{p_{rank}(S(i,Y))|X,Y\in CH\circ CH\}$$

Here the set of instrument channels tested is CH, and PC(i) is the set of pairwise rank correlation values for candidate peak location i.

Annotation device 130 may be configured to determine an air bubble artifact exists at a candidate location when the rank correlation significance test generates a significance value less than a significance threshold across all pairwise comparisons:

$$B=\{i|i,\max PC(i)<T\}$$

Here, B indicates the candidate locations with an air bubble artifact, and T is the significance threshold. T may be between 0.0001 and 0.01, for example a significance threshold of 0.005 has been empirically verified using an independent training dataset.

Annotation device 130 may be configured to replace the air bubble artifact. In some aspects, the signal intensities for the channels within the window may be replaced by annotation device 130 with simulated noise. The simulated noise may be Gaussian noise, with mean and standard deviation determined by annotation device 130 using signal intensities for the region surrounding the air bubble:

$$bkg(i,c)=s([h_{il}-d,h_{il}],\cup s([h_{ir},h_{ir}+d],c)$$

$$\mu(i,c)=\text{mean } bkg(i,c)$$

$$\sigma(i,c)=\text{std } bkg(i,c)$$

$$s([h_{il},h_{ir}],c)\sim \mathcal{N}(\mu(i,c),\sigma(i,c))$$

Here bkg(i, c) is the set of values for the regions surrounding the air bubble. In this example, the regions extend d location units from the left and right peak shoulders. As a non-limiting example, d may be between 5 and 50.

Annotation device 130 may be configured to extend the dynamic range of a channel in the data file. In some embodiments, the channel may be configured to detect a first electromagnetically detectable moiety. For example the channel may be the FAM channel. Annotation device 130 may extend the dynamic range of the channel by extrapolating peak shape over regions of signal saturation. Saturation occurs may occur an electromagnetically detectable moiety fluoresces with a luminescence greater than the collection limit of the instrument RFU sensors, resulting in a loss of information on peak shape. However, since the wavelength spectra for collection allows for bleed-over across channels, peak shape for saturated regions can be extrapolated from channels capturing fluorescence at a similar wavelength.

In a first step, annotation device 130 may be configured to identify a window in the channel. The window may include a saturated region of the channel. For example, annotation device 130 may determine regions of the channel in which signal intensities exceed an amplitude threshold. This amplitude threshold may be empirically-derived, and may be instrument-specific. In the equations below, let s(x, c) represent the signal intensity at index x for instrument channel c, let L represent the set of all location indices meeting saturation criteria, and let T be some instrument-specific threshold:

$$L = \{x | x, s(x, c) > T\}$$

In some aspects, c may comprise the FAM channel. In various aspects, T may be between 1000 and 40000 RFUs, with T describing the RFU levels at which saturation occurs. Annotation device 130 may be configured to modify the signal intensities at indices in L. For example, annotation device 130 may determine combined signal intensities using the signal intensities within the window for the channel and signal intensities within the window for one or more other channels in the data file. These other channels may be configured to detect other electromagnetically detectable moieties. For example, these other channels may be the NED channel or the HEX channel. The signal intensities may be combined linearly or non-linearly. In some embodiments, determining the combined signal intensities comprises extrapolating the shape of a calculated peak in the first channel. For example, the combined signal intensities may comprise a linear combination of the signal intensities within the window for the channels. The combined signal intensities may further include an offset. As a non-limiting example, annotation device 130 may be configured to combine the RFU values from the NED channel into the FAM channel:

$$s_{ext}(x, c) = \begin{cases} s(x, FAM) + s(x, NED), & x \in L \\ s(x, FAM), & \text{otherwise} \end{cases}$$

As shown in the preceding example, annotation device 130 may be configured to replace the signal intensities for the channel within the window with the combined signal intensities.

Annotation device 130 may be configured to generate a sizing standard in step 203, consistent with disclosed embodiments. Annotation device 130 may be configured to use this sizing standard to converting from location units in the signal (analogous to distance traveled in POP7 gel) into base-pair sizes. The sizing standard may comprise data or instructions stored in a non-transitory memory. As described below, annotation device 130 may be configured to use at least one of an internal sizing standard and an external sizing standard to generate this overall sizing standard. In some embodiments, annotation device 130 may be configured to output the sizing standard to a display, printer, another component of system 100 (e.g., Laboratory Information Management System 140), or another system.

Annotation device 130 may be configured to identify and size genotype peaks in step 205, consistent with disclosed embodiments. In this step, annotation device 130 may generate a background model that compensates for the differing effects of the various primer sets in the assay on the measured signals. This background model may be used by annotation device 130 to identify at least one gene-specific product peak in a measured signal.

Annotation device 130 may also be configured to size at least one of the repeat region and the at least one gene-specific product peak using a sizing standard. Annotation device 130 may use the sizing standard generated in step 203. This sizing standard may be an internal sizing standard, an external sizing, or, a combined sizing standard generated from both the internal sizing standard and the internal sizing standard or another sizing standard. For example, annotation device 130 may also be configured to use a sizing standard retrieved from a storage device, received from another component of system 100, or received from another system. In some embodiments, annotation device 130 may be configured to output an indication of the at least one gene-specific product peak, and/or the size of the repeat region to a display, printer, another component of system 100 (e.g., Laboratory Information Management System 140), or another system. This output may include an indication of a genotype of the patient providing the original genomic sample.

Figure 3A:
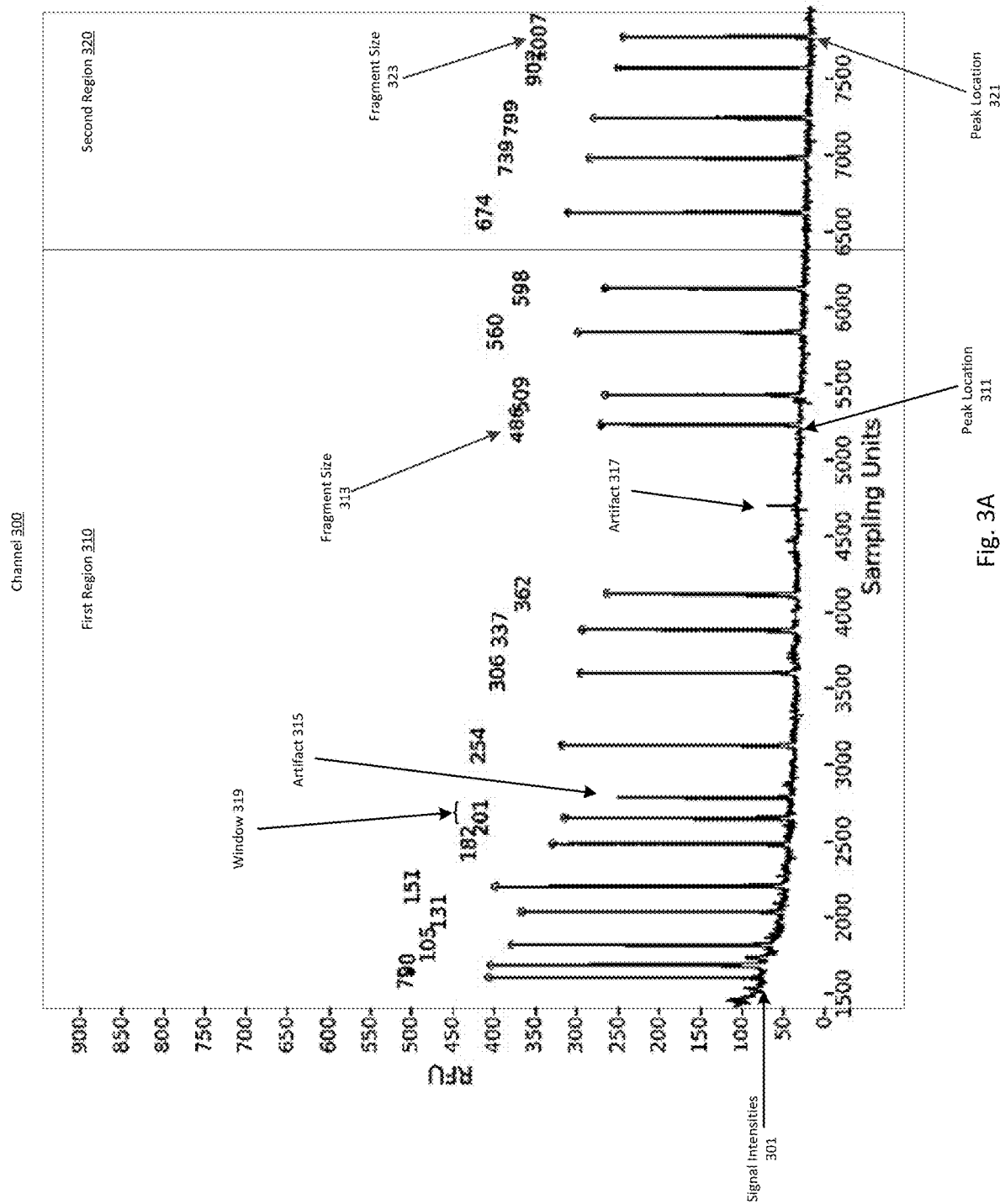
FIG. 3A depicts an exemplary external sizing ladder for use in generating an external sizing standard.

FIG. 3A depicts an exemplary external sizing ladder for use in generating an external sizing standard. As described above, annotation device 130 may be configured to generate a sizing standard in step 203. The current gold-standard for fragment sizing in CE experiments requires the use of externally added dye-labelled molecules of known sizes, which produce fluorescence peaks in a band outside of the frequency spectrum produced by the other electromagnetically detectable moieties used in the PCR assay (e.g., AmplideX® FMR1 PCR products). These fluorescence peaks may be identified independently of target products generated by the assay. In some aspects, these peaks may be used by annotation device 130 to generate an external sizing standard that relates location in the FSA signal (in sampling units) to fragment size (in base pairs). Annotation device 130 may be configured to automatically identify and label ROX fluorescence peaks, while detecting artifacts that might otherwise result in mislabeled peaks (e.g., when using GeneMapper-based workflows, or similar software). The labeling systems and methods used by annotation device 130 may to extend arbitrary sizing ladders (e.g., ROX 1000 or ROX 200) envisioned for used in future assays.

In a first step, annotation device 130 may be configured to identify artifacts arising in a channel in the data file. This channel may be associated with the externally added dye-labelled sizing ladder molecules of known sizes. The artifacts may be "bleed-over" artifacts.

When signal intensities in a channel corresponding to a PCR product exceed an amplitude threshold, the PCR product may be fluorescing with sufficient intensity to affect other channels. Thus annotation device 130 may be configured to first identify a potential bleed-over locations based on signal intensities in the channel corresponding to the PCR product. These locations may have signal intensities exceeding an instrument-specific threshold. This instrument-specific threshold may be empirically determined. It may be otherwise estimated. In the equations below, let s(x, c) represent the signal at the index x for the instrument channel c, let T(instrument) be an instrument-specific threshold, and let B represents the set bleed-over location indices in c.

$$f(x, c) = \Delta_1 \text{sgn}(\Delta_1 s(x, c))$$

$$B = \{x \mid f(x, c) = -2 \wedge s(x, c) > T(\text{instrument})\}$$

$$T(\text{instrument}) = \begin{cases} 20000, & \text{instrument} = 35XX, 37XX \\ 8000, & \text{instrument} = 31XX \end{cases}$$

In some aspects, c may be the FAM channel. The RFU values and instruments listed above are exemplary, and not intended to be limiting. Similar values may be used for the same instructions, and additional values may be determined for similar instruments.

In a second step, annotation device 130 may be configured to determine the extent of the bleed-over from a first channel into a second channel. In some embodiments, annotation device 130 may determine windows including the bleed-over locations. These windows may be determined by annotation device 130 based on signal intensities in the first channel. For example, annotation device 130 may define a window as the region between left and right peak shoulder locations surrounding a bleed-over locations. The left and right peak shoulder locations may be determined by annotation device 130 by assessing the noise profile in regions to the left and right of the peak, and then use parameters from the noise profile to determine a threshold for which the peak signal deviates significantly from the noise. In some embodiments, the noise profile is assumed to follow a Gaussian distribution, and peak shoulders are labelled as the point at which the signal deviates 2 standard deviations above the mean value. As would be appreciated by one of skill in the art, other amplitude threshold values or noise distribution models may be used. In some aspects, the left and right noise profiles may be parameterized independently. The equations below describe a non-limiting example of this process for bleed-over location i:

$$bkg_l(i) = s([i-60, i-30], c)$$

$$bkg_r(i) = s([i+30, i+60], c)$$

$$\mu_l(i) = \text{mean } bkg_l(i), \mu_r(i) = \text{mean } bkg_r(i)$$

$$\sigma_l(i) = \text{std } bkg_l(i), \sigma_r(i) = \text{std } bkg_r(i),$$

$$h_{il} = \min(\{x, x \in [i-d, i] \wedge s(x, c) > \mu_l(i) + 2\sigma_l(i)\})$$

$$h_{ir} = \max(\{x, x \in [i, i+d] \wedge s(x, c) > (i) + \mu_r(i) + 2\sigma_r(i)\})$$

Here c is the first channel, and may be the FAM channel or another channel, and d may be between 30 and 100 sampling units.

In a third step, annotation device 130 may be configured to simulate noise over the region between the left and right peak shoulders. This simulated noise may be Gaussian with parameters chose by annotation device 130 to mimic the signal background in the second channel. The equations below describe a non-limiting example of this process for bleed-over location i:

$$bkg(i) = s([h_{il}-d_2, h_{il}], \text{ROX}) \cup s([h_{ir}, h_{ir}+d_2], c_2)$$

$$\mu(i) = \text{mean } bkg(i)$$

$$\sigma(i) = \text{std } bkg(i)$$

$$s([h_{il}, h_{ir}], c_2) \sim \mathcal{N}(\mu(i), \sigma(i))$$

Here $c_2$ is the second channel, and may be the ROX channel or another channel, and $d_2$ may be between 5 and 50 sampling units. In a fourth step, annotation device 130 may be configured to replace the signal intensities within the window for the other channel with the simulated noise.

FIG. 3A depicts channel 300, the output of the bleed-in location removal, which may comprise signal intensities 301 (in RFUs) over a range of sampling units. Channel 300 may correspond to the ROX PCR products. As shown, signal intensities 301 may include actual peaks and artifacts (e.g., artifacts 315 and 317). Annotation device 130 may be configured to identify peaks in channel 300 when the peaks exceeding a local noise threshold. This identification may include removing peak artifacts that are likely false-positive peak calls.

In a first step, annotation device 130 may be configured to determine potential peaks in the channel that exceed an amplitude threshold calculated using a sliding window. This sliding window may be run across signal intensities 301 by annotation device 130, and may be between 250 and 750, sampling units wide. For example, the sliding window may be 500 sampling units wide. Annotation device 130 may determine statistics, such as mean and standard deviation, of signal intensities 301 within the window. Annotation device 130 may determine the potential peaks as those exceeding an amplitude threshold based on the determined statistics. For example, annotation device 130 may identify peaks over 3 standard deviations above the mean noise level.

In a second step, annotation device 130 may be configured to identify false positive peaks caused by "shoulder" artifacts. To identify false positive peaks annotation device 130 may select only the largest of nearby peaks. For example, annotation device 130 may compare peak height within an interval including a potential peak. Annotation device 130 may determine the potential peak is smaller than another potential peak in the interval. Thus annotation device 130 may therefore determine the potential peak is a false positive peak, and may exclude this potential peak from the peaks in the channel for subsequent analysis. The interval may be between 25 and 75 sampling units wide.

Annotation device 130 may be configured to associate the peaks in the channel with fragment sizes to generate an external sizing standard, consistent with disclosed embodiments. In some embodiments, annotation device 130 may use an iterative approach to choose the most likely peaks in the channel for association with fragment sizes. For example, annotation device 130 may iteratively re-estimate, using identified peaks in a first region of the channel, a linear relationship between peak location and fragment size using a first set of fragment sizes and a first set of corresponding peak locations. This approach takes advantage of the low-noise profile associated with larger fragment sizes for selecting initial conditions. As would be recognized by those with skill in the art, annotation device 130 may be alternatively configured to associate peaks with fragment sizes using an optimization routine that minimizes residuals in accordance with a model applied to the data. This optimization routine can iteratively include and remove peaks for consideration in the model based on criteria that quantify goodness-of-fit for the model.

In a first step, annotation device 130 may be configured to automatically associate expected fragments sizes greater than a predetermined base-pair length with the furthest (by distance in the capillary) peaks in the channel. For example, the last peak location (e.g., peak location 321) may be automatically associated with the largest expected fragment size (e.g., fragment size 323). The next largest peak may be associated with the next largest expected fragment size. The predetermined base-pair length may be approximately 500 base pairs.

In a second step, annotation device 130 may be configured to fit a model to labeled peaks within a predetermined range of base pairs. As would be appreciated by one of skill in the art, values expressed in terms of base pairs may also be expressed in terms of repeat numbers, and the expression of values in terms of base pairs is not intended to be limiting. For example, the linear sizing ladder may be generated by annotation device 130 by fitting a $1^{st}$ order least-squares regression to the labeled peaks within the predetermined range. The predetermined range may begin between 350 and 550 base pairs, and may end between 650 and 750 base pairs. The model may enable annotation device 130 to convert sampling units into base pair lengths and/or repeat numbers.

In a third step, annotation device 130 may be configured to iteratively re-estimate this model using identified peaks in first region 310 of channel 300. In some embodiments, the relationship between sampling unit and base pair may be linear over first region 310. This region of the channel may include peaks corresponding to fewer than a predetermined number of base pairs. Annotation device 130 may be configured to iteratively re-estimate the linear relationship between peak location and fragment size using a first set of fragment sizes and a first set of corresponding peak locations. Annotation device 130 may progress from larger fragment sizes to smaller fragment sizes, including progressively smaller fragment sizes into the set of fragment sizes and set of corresponding peak locations used to re-estimate the linear relationship. For example, when fragment size 313 is the next largest fragment size, annotation device 130 may be configured to add fragment size 313 and corresponding peak location 311 to the first set of fragment sizes and first set of corresponding peak locations. Annotation device 130 may then re-estimate the linear relationship between peak location and fragment size using fragment size 313 and the larger fragment sizes in first region 310, and peak location 311 and the larger peak locations in first region 310.

In each iteration, in some embodiments, annotation device 130 may be configured to determining the peak location corresponding to the next fragment size using the current linear relationship. In some embodiments, annotation device 130 may determine a predicted peak location using the next fragment size and current linear relationship. This next fragment size may be one of the progressively smaller fragment sizes and the current linear relationship may be one of the re-estimated linear relationships discussed above. Annotation device 130 may then determine a window including the predicted peak location. This window may include between 5 and 50 sampling units on either side of the predicted peak location. Annotation device 130 may determining an actual peak location in the channel within a window including the predicted peak location. This actual peak location may be determined as described above, using the derivative of the sign of the derivative of signal intensities 301. Annotation device 130 may be configured to include the actual peak location into the first set of corresponding peak locations. In this manner, as the actual peak locations vary, the current linear relationship may be appropriately updated. Furthermore, this method may provide an additional way to identify artifacts in the data. For example, artifact 317 does not fall within a window (e.g., window 319), and so annotation device 130 may skip this artifact 317 when re-estimating the linear relationship. Thus estimation of the linear relationship may be improved.

In this manner annotation device 130 may continuously update the linear relationship with new data points in a way that increases the accuracy of peak association in the noisier region of the gel. This iterative approach has been shown to be more specific than current methods (GeneMapper, GeneMarker) in ignoring signal artifacts in a ROX channel that can contribute to improper sizing ladder parameterization, and is also robust to mistaking primer-dimer peaks as ROX fragment peaks.

Annotation device 130 may be configured to determine a non-linear relationship between peak location and fragment size for second region 320. In some embodiments, this non-linear relationship may comprise a spline model, such as a 1st-, 2nd- or 3rd-order spline model, or a 2nd- or 3rd-order polynomial model. Annotation device 130 may determine the non-linear relationship using a set of fragment sizes and a set of corresponding identified peak locations in second region 320, such as fragment size 323 and peak location 321. In some aspects, as shown in FIG. 3A, first region 310 and second region 320 may not overlap. For example, the lower bound of second region 320 may equal the upper bound of first region 310. The second region 320 may include fragments greater than 650 to 750 base pairs.

Figure 3B:
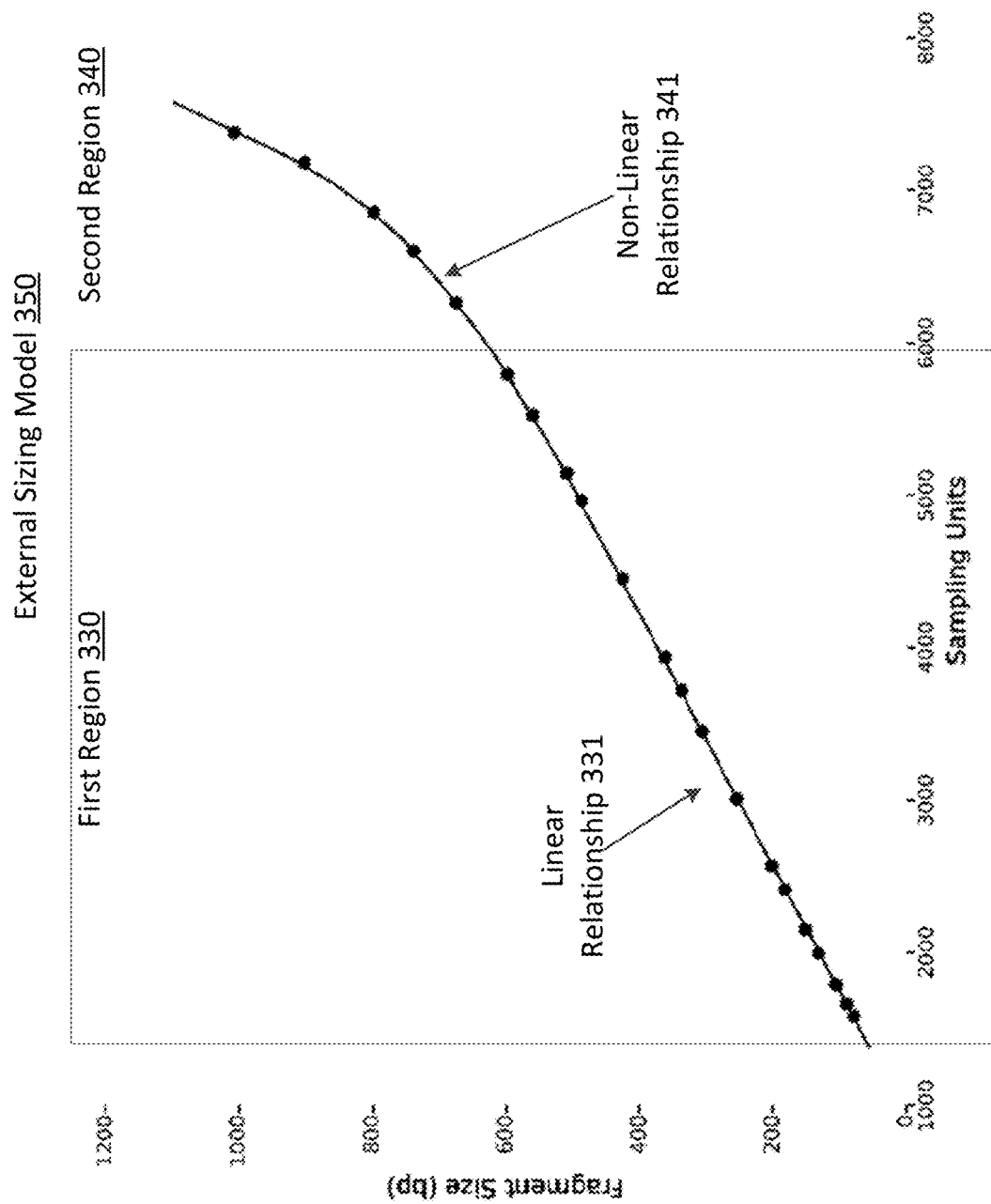
FIG. 3B depicts an exemplary external sizing standard.

As shown in FIG. 3B, annotation device 130 may be configured to generate external sizing standard 350 by combining a linear relationship 331 for first region 330 and a nonlinear relationship 341 for second region 340. To generate external sizing standard 350, annotation device 130 may generate additional points by resampling linear relationship 331 and the nonlinear relationship 341. A univariate spline model is fit to these additional points to generate external sizing standard 350. In some embodiments the additional points may be evenly-spaced along the external sizing standard, for example differing by a constant number of base pairs. The number of additional points may be substantially larger than the original number of fragment sizes. For example, 2 to 10 times as many additional points may generated than the original number of fragment sizes. For example, between 40 and 200 additional points may be used.

In some alternative embodiments, annotation device 130 may be configured to estimate a sizing standard satisfying an optimality criteria. In some aspects, annotation device 130 may associate peaks with fragment sizes using an optimization routine that minimizes residuals in accordance with a model applied to the data. This optimization routine can iteratively include and remove peaks for consideration in the model based on criteria that quantify goodness-of-fit for the model.

For example, annotation device 130 may be configured to generate two or more subsets of the potential peaks in the channel. This generation may be deterministic, or may be at least partially random. As a non-limiting example, each subset may include the first peak. Annotation device 130 may be configured to determine a sizing standard for each subset. These sizing standards may comprise linear relationships, or non-linear relationships, such as spline models or $2^{nd}$ or $3^{rd}$ order polynomial models. In some aspects, annotation device 130 may be configured to resample the sizing standards to generate comparison points. Annotation device 130 may be configured to calculate a cost function for at least some of the resampled sizing standards, based on a comparison between the resampled sizing standards and a reference model. The reference model may comprise an expected sizing standard. As would be appreciated by one of skill in the art, sizing standards generated using subsets including artifacts may differ greatly from the reference model. The value of the cost function for these models will likely be larger than the value of the cost function for subjects including few, or no, artifacts. The cost function may include the L1 norm, the L2 norm, or other cost functions known to one of skill in the art. Thus annotation device 130 may be configured to use the sizing standard minimizing the cost function when sizing at least one of the repeat region and the at least one gene-specific peak. This method may advantageously not require identification of artifacts in the potential peaks, as such artifacts might result in higher costs. As would be appreciated by one of skill in the art, this method may be used to estimate an internal sizing standard or an external sizing standard.

FIG. 4A depicts an exemplary channel of a data file, consistent with disclosed embodiments. In some instances, the external sizing standard described above may be inaccurate because of differences in composition between the externally added dye-labelled PCR products of known sizes and the PCR fragments of the genomic region. For example, ROX fragment mobility in capillary electrophoresis differs from FMR1 fragment mobility, because of the GC-rich nature of FMR1 fragments relative to the nucleotide-balanced nature of ROX fragments. Because of these inaccuracies, annotation device 130 may be configured to generate an internal sizing standard. In some embodiments, annotation device 130 may be configured to generate a mobility corrected sizing standard using the internal sizing standard and an external sizing standard. The external sizing standards may be derived from the ROX channel as described above with regard to FIGS. 3A and 3B. Generation of the internal sizing standard by annotation device 130 may include identifying a repeat profile in a channel of a data file and estimating a linear relationship between repeat peak location and repeat fragment size.

As shown in FIG. 4A, the channel of the data file may include a repeat profile 410. The repeat profile may comprise the portion of the channel beginning with the smallest detected PCR fragment peak and ending with the largest detected PCR fragment peak or gene product peak. For example, repeat profile 410 may begin after 2000 sampling units and may end between 4500 and 5000 sampling units. As depicted in FIG. 4A, repeat profile 410 may display a repetitive sequence of peaks corresponding to incrementally larger fragments. Depending on the genomic sample, repeat profile 410 may also display one or more gene product peaks, such as the peaks around 4500 sampling units.

Annotation device 130 may be configured to identify repeat profile 410 in a channel of a data file. In some embodiments, annotation device 130 may use an external sizing standard, such as a ROX ladder, to predict and approximate location for the beginning of repeat profile 410. When annotation device 130 cannot generate an external sizing standard satisfying quality control criteria (described below), or when only using an internal model, annotation device 130 may use the following process to determine the beginning of repeat profile 410.

In a first step, annotation device 130 may be configured to determine an approximate starting location of the repeat profile. Annotation device 130 may perform a summation transformation of the channel using a first window size W:

$$t(i) = \sum_{i_x}^{i_x+W} s(i_x, c), i_x = (Wx | x = 1, 2, 3 \dots)$$

Thus t(i), the transformed data, may comprise the sum of the signal intensities within the first window for the channel, for non-overlapping first windows. As would be recognized by one of skill in the art, annotation device 130 may additionally or alternatively low-pass filter the channel. The channel c may be the FAM channel, and the first window size W may be between 50 and 1000 sampling units. For the largest peak in that transformed signal (which may be caused by primer-dimer amplification events), annotation device 130 may find at least the right-most peak shoulder, according to the discussion of peak shoulder provided above.

After using t(i) to determining the location of the right-most peak shoulder, annotation device 130 may be configured to transform the signal intensities within second windows of the channel into the frequency domain and determine when a dominant frequency of the signal intensities within the second window satisfies a frequency criterion. For example, annotation device 130 may calculate the dominant frequency of the channel within a second window, beginning at this location. The second window may be between 100 and 200 sampling units wide. Annotation device 130 may determine the approximate beginning of the repeat profile as the initial second window in which the difference between the dominant frequency of the signal and a predetermined frequency satisfies an empirically-derived difference criterion.

In a second step, annotation device 130 may be configured to determine a precise starting location of the repeat profile. Annotation device 130 may determine this precise starting location using statistical measures of signal intensities within a third window. For example, the exact repeat start site may be determined by annotation device 130 as the first location greater than a predetermined percentile of the signal intensities within the third window. In some embodiments, the third window may begin at the approximate starting location. In the equation below, let a represent the approximate location of the signal start site and let c be the channel:

$$w = [a, a+1000]$$

$$\text{start} = \min(\{x, x \in w \wedge s(x,c) > Q_{85}(s(w,c))\})$$

In this example, the statistical measure is the $85^{th}$ percentile, but the percentile may be between the $70^{th}$ and $99^{th}$ percentile, for example. Likewise, the width of the third window is 1000 sampling units, but the third window may be between 50 and 5000 sampling units wide. Amplitude thresholds derived from other statistical measures such as means and standard deviations may also be used. The channel c may be the FAM channel.

In a second step, annotation device 130 may be configured to determine an ending location of the repeat profile. In some embodiments, annotation device 130 may filter the channel to determine the end of the ending location of the repeat profile. For example, Annotation device 130 may apply a percentile filter across the channel using a fourth window. After the transformation is applied, the signal end location may be selected by annotation device 130 as the last transformed region that exceeds an amplitude threshold:

$$t(i) = Q_{90}(s([i_x, i_x+100], c)), i_x = (100x | x = 1, 2, 3 \dots)$$

$$\text{end} = 100 * \max(\{i, t(i) > 100\})$$

Thus t(i), the transformed data, may comprise the percentile-filtered value of channel c over the fourth window. In this example, the percentile is the $90^{th}$ percentile, but the percentile value may range from the $70^{th}$ to the $99^{th}$ percentile. Likewise, the width of the fourth window is 100 sampling units, but the third window may be between 50 and 5000 sampling units wide. Amplitude thresholds derived from other statistical measures such as means and standard deviations may also be used. The channel c may be the FAM channel. Here end may be the index of the final value in repeat profile 410. The amplitude threshold may be instrument-specific and may be empirically derived. Here the value is 100 RFUs, but this value is not intended to be limiting.

FIG. 4B depicts generation of an internal sizing standards using a repeat profile, consistent with disclosed embodiments. Annotation device 130 may be configured to identify amplification peaks in the channel arising from the repeat primers. Annotation device 130 may associate these peaks with expected fragment sizes to generate the internal sizing standard. In some aspects, as discussed in greater detail below, annotation device 130 may iteratively call repeat peaks using a window derived from the periodicity of the repeat profile. Annotation device 130 may adjust this window as periodicity shifts in the repeat profile, and may interpolate peak locations where repeat peaks are suppressed (e.g. at AGG interruption sites).

In a first step, after the start and end locations of the signal are identified, annotation device 130 may be configured to determine an initial interval value and an initial amplitude threshold. As described above, annotation device 130 may dynamically determine the periodicity of the repeat profile using a frequency based analysis. For example, annotation device 130 may perform a Fourier transform on an initial portion of the repeat profile to identify a dominant frequency of the repeat profile. The initial portion may begin at the start location. Annotation device 130 may calculate the initial interval value for determining predicted peak locations using the inverse of the dominant frequency:

$$f_{rp} = \mathcal{F}\{s([\text{start}, \text{start} + 1000], c)\}$$

$$d_{rp} = \frac{1}{f_{rp}}$$

Here $f_{rp}$ is the dominant frequency of channel c over the initial portion. In this example, the initial portion is 1000 sampling units wide, but the initial portion may be between 500 and 5000 sampling units wide. The channel c may be the FAM channel.

Annotation device 130 may dynamically determine a threshold for calling repeat peaks in the repeat profile. The threshold may be an amplitude threshold. For example, annotation device 130 may be configured to determine the initial amplitude threshold for identifying repeat locations using a statistical measure calculated over an initial portion of the repeat profile. The initial portion may begin at the start location, and the statistical measure may be a percentile:

$$t_{rp} = Q_{25}(s([\text{start}, \text{start} + 2000]), c)$$

Here $t_{rp}$ is the initial amplitude threshold. In this example, the 25$^{th}$ percentile is the statistical measure, but the percentile may range between the 5$^{th}$ and 50$^{th}$ percentiles. Likewise, the initial portion is 2000 sampling units wide, but may be 100 to 5000 units wide. The channel c may be the FAM channel. Annotation device 130 may determine the initial amplitude threshold using other statistical measures such as means and standard deviations.

In a third step, annotation device 130 may be configured to iteratively generate a set of repeat peak locations. In various aspects, annotation device 130 may determine predicted peak location 425 location in repeat profile 410 for each iteration. Predicted peak location 425 may depend on previous peak location 421 and interval value 423. In some aspects, annotation device 130 may call the repeat peaks in the repeat profile using a sliding window. In some embodiments, interval value 423 may be derived from the initial interval value. Annotation device 130 may identify a repeat peak location within window 427 including predicted peak location 425. In some embodiments, the window for selecting peaks may be between 25 to 100% of interval value 423. In certain embodiments, the window is between 50 to 100% or 80 to 100% of interval value 423. Annotation device 130 may be configured to determine the location of the largest peak within window 427. When a signal intensity at this identified peak location exceeds amplitude threshold 429, this actual peak 431 may be added to the set of repeat peak locations. In some embodiments, amplitude threshold 429 may be derived from the initial amplitude threshold. In the next iteration, the previous peak location may be the actual peak 431 identified during this iteration.

In some embodiments, annotation device 130 may be configured to update one or more of amplitude threshold 429 and interval value 423. For example, amplitude threshold 429 may be the average of the signal intensity at the actual peak for two or more previous iterations. Likewise interval value 423 may be the average of the differences in location between the actual peak and the previous peak for two or more previous iterations. In some embodiments, these averages may be over the 3 to 50 previous iterations. In this manner, annotating device 130 may accommodate shifts in the periodicity and amplitude of the repeat peaks over the course of the repeat profile:

$$x_{next} = \text{argmax}_i \left( s\left( \left[ i + \frac{d_{rp}}{2}, i + \frac{3}{2}d_{rp} \right] \right) \right)$$

$$p_{next} = \begin{cases} x_{next}, & s(x_{next}, c) > t_{rp} \\ i + d_{rp}, & \text{otherwise} \end{cases}$$

Here the $x_{next}$ is the location of the largest peak within the window, and this peak is added to the set of repeat peak locations when the signal intensity for channel c, which may be the FAM channel, exceeds the amplitude threshold. In some embodiments, annotation device 130 may interpolate repeat peaks in the repeat profile below the threshold. For example, when the signal intensity does not exceed the amplitude threshold, the predicted peak location is added to the set of repeat peak locations. In this manner annotating device 130 may interpolate peaks in regions where the repeat peak amplitudes are diminished. This interpolation may improve the accuracy of the sizing standard generated by annotation device 130.

In a fourth step, annotation device 130 may be configured to generate an internal sizing standard describing the relationship between repeat peak location and repeat fragment size. In some embodiments, annotation device 130 may use the estimated starting peak location in the repeat profile and subsequent peak location to generate a calibration curve (i.e. sizing standard) that maps from sampling units to base pair units. For example, annotation device 130 may generate the internal sizing standard using the set of repeat peak locations and a set of corresponding fragment sizes. Annotation device 130 may establish the correspondence between the repeat peak locations and the fragment sizes by associating the first repeat peak location with the smallest fragment size, the second repeat peak location with the next smallest fragment size, etc. In some embodiments, each additional repeat peak location may be associated with a fragment size that is one additional repeat larger than the previous fragment size. Annotation device 130 may generate the relationship by regressing the set of corresponding fragment sizes against the set of repeat peak locations.

As described above, with regard to FIG. 2, annotation device may be configured to use an internal sizing standard, an external sizing mode, or a combined sizing standard. For example, annotation device 130 may be configured to use the internal sizing standard and an external sizing standard to generate a mobility corrected sizing standard. Annotation device 130 may generate the mobility corrected sizing standard by generating an affine transformation using the internal sizing standard and the external sizing standard. This affine transformation may ensure that both the linear and nonlinear components of the external sizing ladder contribute to the mobility corrected sizing standard. The affine transformation may be described by the following equations: let $L_{rp}(x)$ represent the internal sizing standard, $L_{ROX}(x)$ represent the external model, and $L_{NL}(x)$ represent the univariate spline model for the non-linear region of the external model:

$$L_{rp}(x) = m_{rp}x + b_{rp}$$

$$L_{ROX}(x) = \begin{cases} m_{ROX}x + b_{ROX}, & x \in \text{linear range} \\ L_{NL}(x), & \text{otherwise} \end{cases}$$

$$L_{final}(x) = L_{ROX}(x)\left(\frac{m_{rp}}{m_{ROX}}\right) + b_{rp} - b_{rox}\left(\frac{m_{rp}}{m_{ROX}}\right)$$

In this example, the sensitivity of the mobility corrected sizing standard depends on the ratio of the sensitivities of the external sizing standard $L_{ROX}(x)$ and the internal sizing standard $L_{rp}(x)$, while the offset of the mobility corrected sizing standard depends on the offsets of the internal sizing standard and external sizing standard, and the ratio of the sensitivities of the external sizing standard and the internal sizing standard. Annotation device 130 may be configured to apply the affine transformation to the external sizing standard to obtain the mobility corrected sizing standard. For example, annotation device 130 may calculate the mobility corrected sizing standard using the above equations.

As described above with regard to FIG. 11, annotation device 130 may be configured to identify and size genotype peaks. Channels may exhibit both repeat-segment and gene-specific amplification, so annotation device 130 may separate these two components of signal intensity prior to identifying the genotype peaks. Additionally, annotation device 130 may also be configured to identify abnormal genotype peaks, as described in greater detail below.

In a first step, annotation device 130 may be configured to generate a background model for separating the signal contribution of repeat amplification events from the signal contribution of gene-specific amplification events. Creation of the background model may address gaps in the repeat profile created by interruptions in the repeat region, such as those arising from AGG interruptions in a FMR1 repeat region. Creation of the background model may also address gene-specific product peaks that deviate from the repeat peak component of the repeat profile, but without characteristics that would allow a frequency-based filtering approach to deconvolve.

Figure 5:
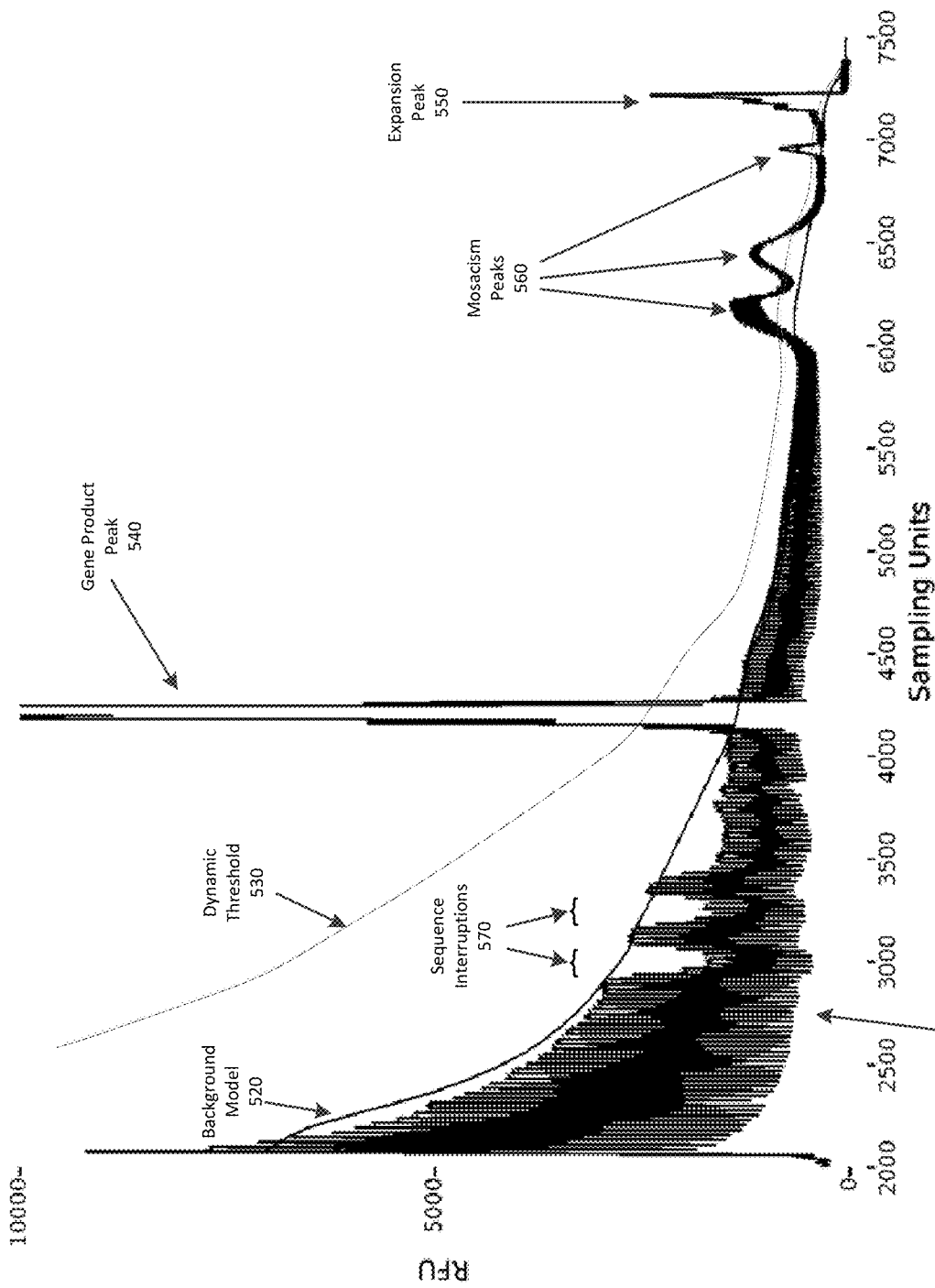
FIG. 5 depicts an exemplary repeat profile annotated with a background model and dynamic threshold.

FIG. 5 depicts an exemplary repeat profile 510 annotated with background model 520 and dynamic threshold 530. In some embodiments, the background model may depend on the magnitude of the repeat profile within a given window. Where gaps in the repeat profile arise from sequence interruptions 570 in the repeat region, the background model may depend on the magnitude of local repeat peaks proximal to the interruption. The background model during gene-specific product peak 540, expansion peak 550, and mosiacism peaks 560 may also depend on the magnitude of local repeat peaks proximal to the interruption.

In a first step, annotation device 130 may be configured to generate background model 520 by filtering repeat profile 510. In some embodiments, annotation device 130 may filter repeat profile 510 using a filter configured to output values based on at least one statistical measure of a sliding window of input data. For example, the filter may output the sum of the median and the interquartile range of the repeat profile 510 within the window. The window may be between 3 and 30 repeats wide, for example 11 repeats wide. This design may enable annotation device 130 to capture the height of repeat peaks in the window, while rejecting large fluctuations in the repeat signal caused by AGG interruptions and gene-specific products. As would be recognized by one of skill in the art, other filter types, such as median smoothing filters and linear filters (e.g., Butterworth filters) may alternatively be used.

In a second step, annotation device 130 may be configured to further filter background model 520 using a filter configured to attenuate high-frequency components of the background model. In some embodiments, annotation device 130 may use a Savitzky-Golay filter to attenuate the high-frequency components of background model 520. The Savitzky-Golay filter may be between 3 and 30 wide, for example 7 repeats wide. The Savitzky-Golay filter may be tuned to match the repeat profile dynamics, preventing the peaks and troughs visible in the output of other filter designs.

In a third step, annotation device 130 may be configured to determine peak shoulder in the resulting background model 520 according to the methods described above. In some embodiments, annotation device 130 may replace the signal intensities within the peak shoulders with values linearly interpolated between the peak shoulder values.

Annotation device 130 may be configured to generate a dynamic threshold from the background model. The dynamic threshold may be used by annotation device 130 to identify gene-specific product peaks. By dynamically scaling the background model to generate the dynamic threshold, annotation device 130 may increase specificity in the lower fragment size ranges, while increasing sensitivity in the higher fragment size ranges. In some embodiments, annotation device 130 may be configured to determine a first region of the background model corresponding to amplification products with sizes above a first fragment size and below a second fragment size. Annotation device 130 may also determine a second region of the background model corresponding to amplification products with sizes above the second fragment size. Annotation device 130 may multiply the first region of the background model by a first scaling factor that varies from an initial scaling factor to a second scaling factor less than the initial scaling factor. For example, the first scaling factor may vary linearly from the initial scaling factor to the second scaling factor. Annotation device 130 may also multiply the second region of the background model by the second scaling factor.

In the equations below, let $M_{BG}$ represent background model 520, let $M_G$ represent the dynamic threshold 530, let $r_1$ represent the index corresponding to the first fragment size, and let $r_2$ represent the index corresponding to the second fragment size:

$$M_G(x) = \begin{cases} 3 M_{BG}, & x < r_0 \\ M_{BG}\left(\dfrac{3(x - r_1) + 1.5(r_2 - x)}{r_2 - r_1}\right), & r_1 < x < r_2 \\ 1.5 M_{BG}, & x > r_2 \end{cases}$$

In this example, the first scaling factor is 3 and the second scaling factor is 1.5, but these values are not intended to be limiting. The first scaling factor may vary between 1.25 and 10, and the second scaling factor may vary between 1.25 and 10. In some aspects, the first fragment size may correspond to 0 repeats, or to as many as 20 repeats. In various aspects, the first fragment size may correspond to between 70 and 190 repeats, for example 120 repeats. In this example, annotation device 130 may apply a piecewise scale factor to background model 520 that decreases from 3 to 1.5 in the region between 0 and 120 repeats, and then remains constant at 1.5 after 120 repeats, to obtain dynamic threshold 530.

Annotation device 130 may be configured to determine the genotype peak set using dynamic threshold 530. Annotation device 130 may identify potential locations in the repeat profile based on the derivative of the sign of the derivative of the signal intensity, as described above. When the value of the repeat profile at a potential peak location exceeds the value of the dynamic threshold at that potential peak location, annotation device 130 may include the potential peak location in the genotype peak set.

Annotation device 130 may be configured to associate repeat sizes with the gene-specific product peaks using a sizing ladder and the gene-specific product peak locations. The sizing standard used by annotation device 130 may comprise one of the internal sizing standard, the external sizing standard, and the mobility corrected sizing standard. In some aspects, annotation device 130 may use the following equation to associate to repeat sizes with product peak locations:

$$S_G = \left\{ \dfrac{L_{sizing}(i) - s_p}{s_r}, \forall i \in G \right\}$$

In this example, let $L_{sizing}(x)$ be the sizing standard, let $S_p$ be the size of the gene-specific product primer in base pairs, let $S_r$ be the size of the repeat in base pairs, and let G be the genotype peak set identified using the dynamic threshold. As a non-limiting example, $S_p$ may range between 20 and 1000 base pairs, for example 240 base pairs, though other values are possible. Likewise, $S_r$ may be 3 base pairs, though other values are possible. Gene-specific or repeat-specific variation in these and other parameters is within the scope of the described configurations.

Annotation device 130 may be configured to resolve gene-specific product peaks that do not present as normal gene-specific product peaks (i.e. homozygous female samples, n/n+1 genotypes, expanded samples) after determining the genotype peak set. Homozygous female peaks may be resolved using supplied sex information. For example, singly-called gene-specific product peaks may be resolved into a homozygous genotype for female samples.

Figure 6A:
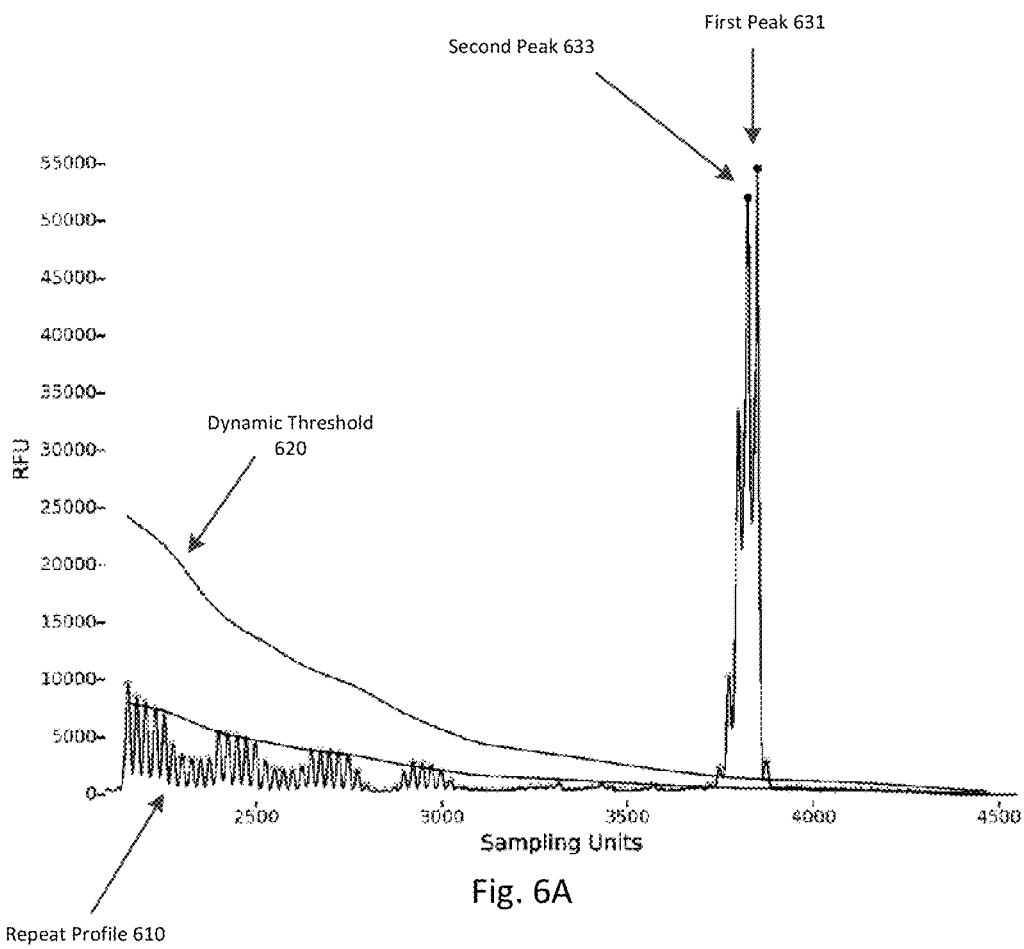
FIG. 6A depicts an exemplary repeat region for a heterozygous female showing an (n, n+1) genotype.

As shown in FIG. 6A, annotation device 130 may be configured to determine gene-specific product peak locations for genomic samples with proximal genotypes (n/n+1). Identifying such samples may be a challenging problem, and such samples may comprise 10% of female samples. Annotation device 130 may identify such samples by identifying second peak 633 beside first peak 631. For example, annotation device 130 may identify second peak 633 in repeat profile 610a at a second location adjacent to first peak 631. Second peak 633 may be similar in magnitude to the first peak 631. For example, annotation device 130 may determine that a second value of the repeat profile at the second location satisfies an amplitude criterion based on the first value. For example, the second value of the repeat profile at the second location may exceed an amplitude threshold that is between 70% and 90% of the first value. In some embodiments, both first peak 631 and second peak 633 may exceed dynamic threshold 620.

Figure 6B:
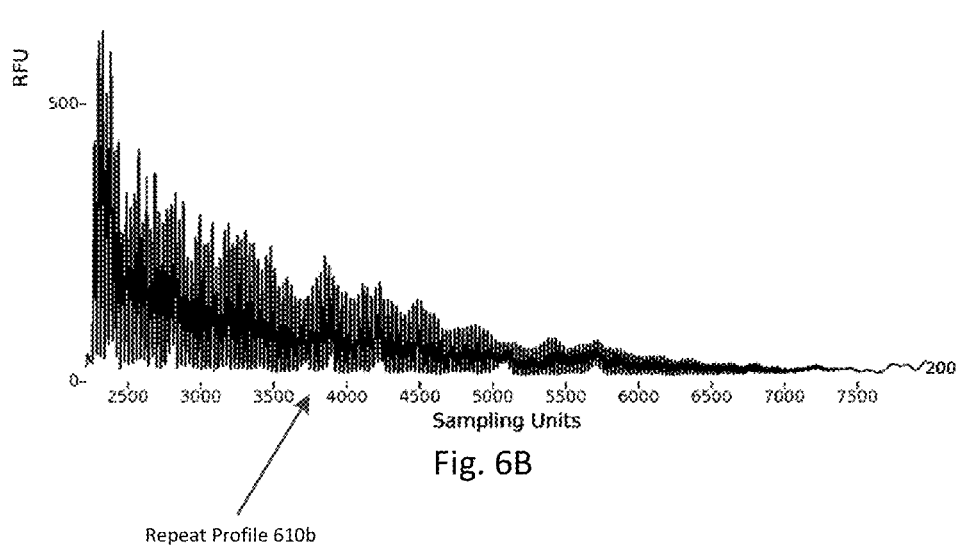
FIG. 6B depicts an exemplary expanded repeat region.

As shown in FIG. 6B, annotation device 130 may be configured to label a sample as an extended sample when no genotype peaks are identified, but repeat profile 610b shows expansion. As would be appreciated by one of skill in the art, when the repeat region is FMR1 such samples may occur for samples with repeat profiles expanding far past 200 repeats.

As with any complex PCR-based workflow, products can sometimes fail to amplify as a result of either operator or instrument error. Because this can render samples uninterpretable, annotation device 130 may be configured to flag samples for re-analysis. Annotation device 130 may perform multiple quality-control measures to safeguard users against misinterpreting results. In some embodiments, annotation device 130 may include two categories of these quality-control criterions: three criteria (sizing standard criteria, repeat profile signal-to-noise criterion, and repeat profile contamination criterion) explicitly fail the sample and don't produce genotype calls, and one criterion (minor allele sensitivity criterion) produces genotype calls that should be interpreted by users with greater skepticism. This "at risk" QC category is designed to protect users from setting thresholds for genotype calls below the level which their data can reliably produce.

Figure 7A:
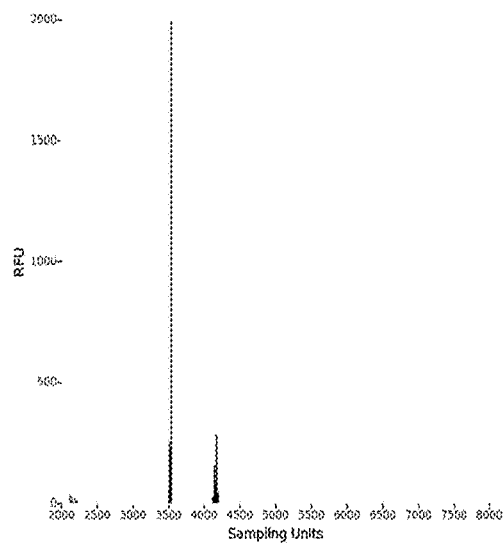
FIGS. 7A-7C depict samples with different quality control issues.
Figure 7B:
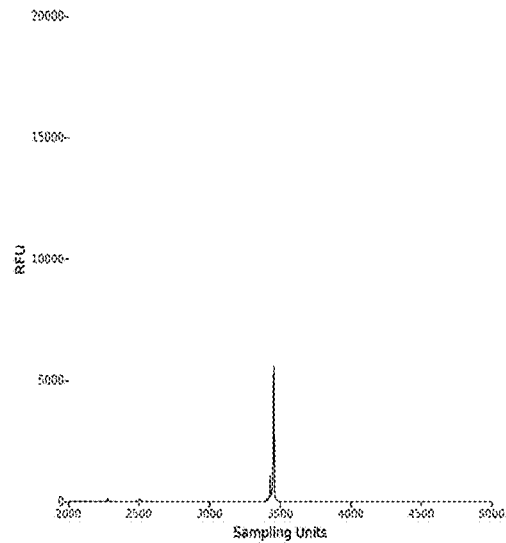
Figure 7C:
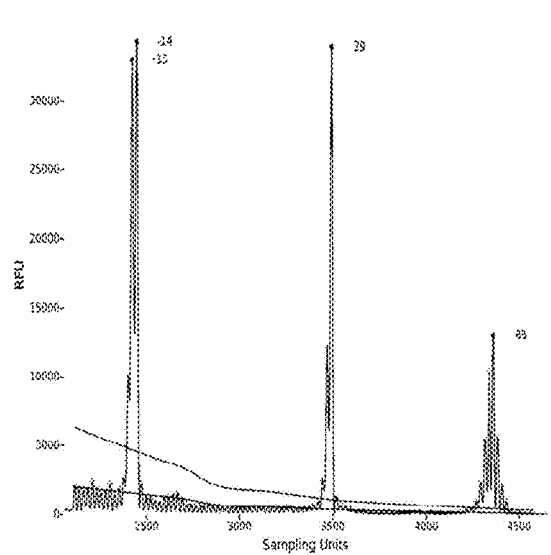

FIGS. 7A-7C depict samples with different quality control criteria. FIG. 7A depicts a sample with a poor ROX ladder. This sample may fail the sizing standard criteria. The sizing standard criteria ensures that the sizing standard is derived correctly and that it matches expectations with respect to internal calibrators. Annotation device 130 may use three different criteria for ensuring this, and may require satisfaction of at least one criteria for the sample to pass. For example, satisfaction of all three criteria may be required. The first of the criteria may be that the coefficient of determination ($R^2$) for the external model fit against external ladder peaks is greater than 0.98. The second criteria may be that the coefficient of determination for the internal model fit against internal ladder peaks is greater than 0.98. The final criteria may be that a consistency criterion that compares the internal sizing standard to the external sizing standard. This consistency criterion may be satisfied when the external model fit against the internal model fit for evenly spaced points throughout the fit is greater than 0.98. The coefficient of determination thresholds above were determined empirically from the independent training set, by selecting a level that accurately discriminated between samples that produced incorrect sizing and samples that produced correct sizing. In other embodiments, a frequency-based analysis may be determine whether the repeat profile is of sufficient periodicity to use in sizing.

FIG. 7B depicts a sample with poor PCR amplification. This sample may fail the repeat profile signal-to-noise criterion. This criterion safeguards users against interpreting results for samples with poor amplification. Samples with poor amplification may violate assumptions of the algorithm during processing and could potentially result in incorrect or false-negative genotypes being reported/missed. At a high-level, the algorithm may verifies there exists a sufficient signal-to-noise ratio for the start of the repeat profile against the noise-level of the instrument proximal to the start of the repeat profile. The SNR threshold for this QC may be determined empirically from an independent training set, by selecting a level that accurately discriminated between samples that produced incorrect sizing and samples that produced correct sizing.

$$L_n = Q_{75}(s([I_{rp}(1) - 200, I_{rp}(1) - 50], c))$$

$$L_{rp} = \text{median}(\{s(I_{rp}(i), c), i = (1, 2, 3, 4, 5)\})$$

$$QC_{SM}\begin{cases} \text{PASS,} & L_{rp} - T_{ma} > 150 \\ \text{FAIL,} & \text{otherwise} \end{cases}$$

In these exemplary equations, channel c may be the FAM channel. In this example, a 75$^{th}$ percentile may be calculated by annotation device 130 over a windowed portion of the repeat profile. One of skill in the art would recognize that other percentiles may be used, for example the 60$^{th}$ to 95$^{th}$ percentiles, or other statistical measures, such as mean and standard deviations. Similarly, in this limiting example the windowed portion of the repeat profile extends from 200 sampling units before the start location to fifty units before the start location. But other windows of the channel may also be used.

FIG. 7C depicts a sample with a contamination peak. This sample may fail the repeat profile contamination criterion. The repeat profile contamination criterion may be used to identify instances of off-target amplification or amplification artifacts related to improper sample preparation, which have the potential to contribute to incorrect genotypes being reported. The failure criteria for this QC may be defined as a gene-specific product peak being identified in a range that cannot possibly be produced by the gene-specific primers. For instance, if the repeat number derived for a gene-specific product peaks is less than 0 repeats (i.e. in some cases less than 240 bp), then the sample may be flagged as having contamination.

$$QC_{CT} = \begin{cases} \text{PASS,} & \min(S_G) > 0 \\ \text{FAIL,} & \text{otherwise} \end{cases}$$

The minor allele sensitivity criterion may caution users against setting minor allele calling thresholds below levels that are possible for the assay, with respect to the ratio between the background noise of the instrument and the largest genotype peak in the sample. If the ratio between the noise level (as explained above) and the largest genotype peak exceeds the minor allele frequency, then minor alleles at that level cannot be accurately identified, and the sample is flagged with an "at risk" QC that users should interpret with more rigor. In the equation below, let G represent the set of genotype peak locations, c represent the channel, $T_{ma}$ represent the minor allele threshold specified by the user, and $L_n$ represent the background noise level of the signal calculated for the minor allele sensitivity criterion:

$$P_{max} = \max\{s(i, c), \forall i \in G\}$$

$$QC_{MA}\begin{cases} \text{PASS,} & \frac{L_n}{P_{max}} > T_{ma} \\ \text{FAIL,} & \text{otherwise} \end{cases}$$

Figure 8:
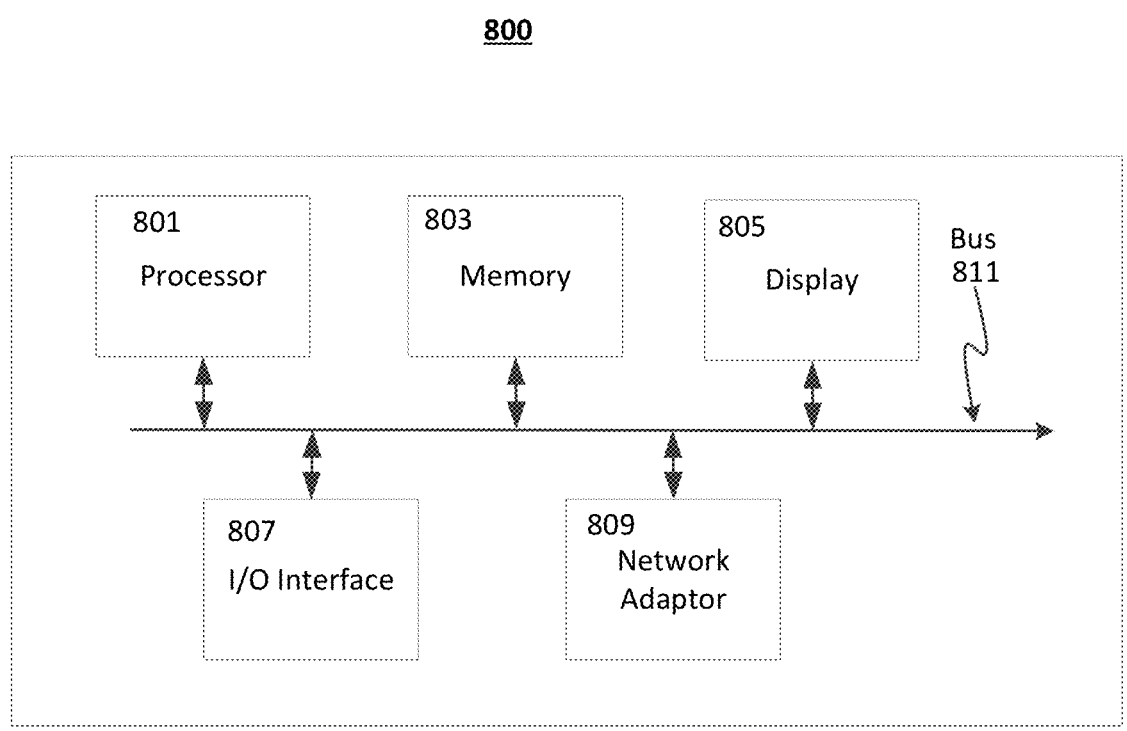
FIG. 8 depicts an exemplary computing system for genotype peak sizing.

FIG. 8 depicts an exemplary computing system for genotype peak sizing. In some embodiments, computing system 800 includes a processor 801, memory 803, display 805, I/O interface(s) 807, and network adapter 809. These units may communicate with each other via bus 811, or wirelessly. The components shown in FIG. 8 may reside in a single device or multiple devices.

Consistent with disclosed embodiments, processor 801 may be a microprocessor, central processing unit (CPU), graphical processing unit (GPU), or similar device. Memory 803 may include non-transitory memory containing non-transitory instructions, such as a computer hard disk, random access memory (RAM), removable storage, or remote computer storage. In some aspects, memory 803 may be configured to store software programs. In some aspects, processor 801 may be configured to execute non-transitory instructions and/or programs stored on memory 803 to configure computing system 800 to perform operations of the disclosed systems and methods. In various aspects, as would be recognized by one of skill in the art, processor 801 may be configured to execute non-transitory instructions and/or programs stored on a remote memory to perform operations of the disclosed systems and methods. Display 805 may be any device which provides a visual output, for example, a computer monitor, an LCD screen, etc. I/O interfaces 807 may include means for communicating information to computing system 800 from a user of computing system 800, such as a keyboard, mouse, trackball, audio input device, touch screen, infrared input interface, or similar device. Network adapter 809 may include means for enabling computing system 800 to exchange information with external networks. For example, network adapter 809 may include a wireless wide area network (WWAN) adapter, a Bluetooth module, a near field communication module, or a local area network (LAN) adapter.

Kits of reagents, analysis software, and macromolecules for carrying out the assays disclosed herein are also provided herein. In certain embodiments, kits for genotyping a repeat region in a sample comprise one or more primers for amplification of a repeat region, a buffer, and analysis software or software key as described herein. In other embodiments, kits for genotype-peak sizing comprise one or more primers for amplification of a repeat region, a buffer, and a non-transitory media sorting analysis software and/or a software key. In certain aspects, the kits comprise a primer that is identical or complementary to a portion of a repeat region of a genetic locus as described herein. In other aspects, the kits further comprise an amplification primer set or multiple amplification primer sets, wherein at least one of the primers comprises a sequence that is identical to or complementary to a portion of a repeat region of a genetic locus as described above. The analysis software as described herein may comprise data and/or instructions stored on a non-transitory computer-readable medium such as a CD-ROM or other data storage device. The term "software key" refers to a software license key, cryptographic key, URL, and/or password configured to enable downloading of or access to the analysis software described herein. This "software key" may be displayed on a non-transitory medium such as paper, cardstock, a sticker, or a similar medium; or may be stored on a non-transitory computer-readable medium such as a CD-ROM, or other data storage device (e.g., located in a "readme" file). The kits specifically contemplate including, for example, the analysis software that performs the data processing and calculating methods of any of claims 1-83 of this specification.

The kits further optionally comprise an enzyme for carrying out the assays described herein, including but not limited to a polymerase such as a DNA polymerase or reverse transcriptase. In certain aspects, the kits include an external sizing ladder. The sizing ladder may be a ROX ladder or a sizing ladder as described herein. In certain aspects, the kits include a positive control sample, for example a template control sample or a pooled cell line control sample.

The kit may also comprise reagents for amplifying a repeat region, including primers, dNTPs, polymerase, and/or buffers. Such a kit may include one or more buffers, such as a reaction, amplification, and/or a polymerase buffer, compounds for preparing a DNA sample, and components for isolating and/or detecting an amplification product, such as a probe or label, for example.

In some embodiments, kits of the invention include one or more of the following (consistent with methods, reagents, and compositions discussed above): components for sample purification, including a lysis buffer with a chaotropic agent; a glass-fiber filter or column; an elution buffer; a wash buffer; an alcohol solution; and a nuclease inhibitor. The components of the kits may be packaged either in aqueous media or in lyophilized form, for example, and will be provided in a suitable container. The components of the kit may be provided as dried powder(s). When reagents and/or components are provided as a dry powder, the powder can be reconstituted by the addition of a suitable solvent. It is envisioned that the solvent may also be provided in another container. The container will generally include at least one vial, test tube, flask, bottle, syringe, and/or other container or equivalent, into which the solvent is placed, optionally aliquoted. When the components of the kit are provided in one and/or more liquid solutions, the liquid solution is an aqueous solution, with a sterile aqueous solution being particularly preferred. The kits may also comprise a second container or equivalent for containing a sterile, pharmaceutically acceptable buffer and/or other solvent.

Such kits may also include components that preserve or maintain DNA or RNA, such as reagents that protect against nucleic acid degradation. Such components may be nuclease or RNase-free or protect against RNases, for example. Any of the compositions or reagents described herein may be components in a kit. Additional materials may include a suitable reaction container, a barrier composition, reaction mixtures for amplification and/or PCR (including buffers and reagents such as dNTPs), nuclease- or RNAse-free water, RNase inhibitor, and/or any additional buffers, compounds, co-factors, ionic constituents, proteins, enzymes, polymers, and the like that may be used in the reactions.

EXAMPLES

The following examples serve to illustrate, and in no way limit, the present disclosure.

Example 1: Amplification of the Repeat Region

Figure 9:
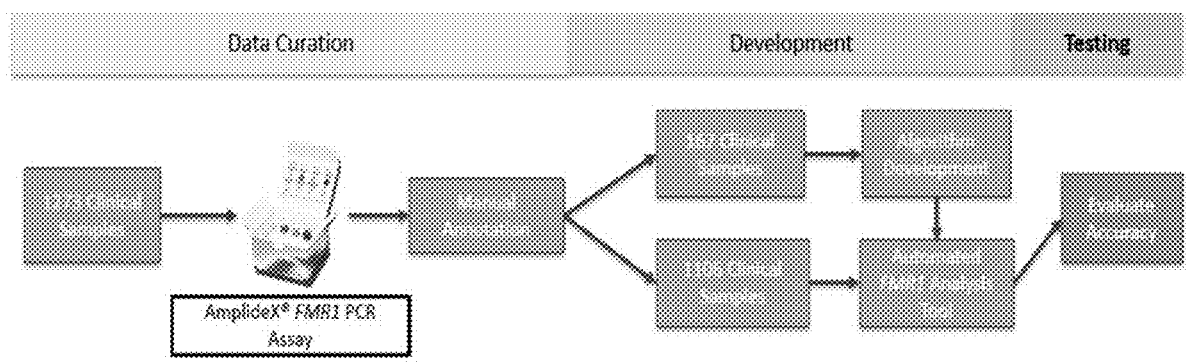
FIG. 9 depicts a schematic representation of the experimental design according to certain embodiments described in Example 1.
Figure 16:
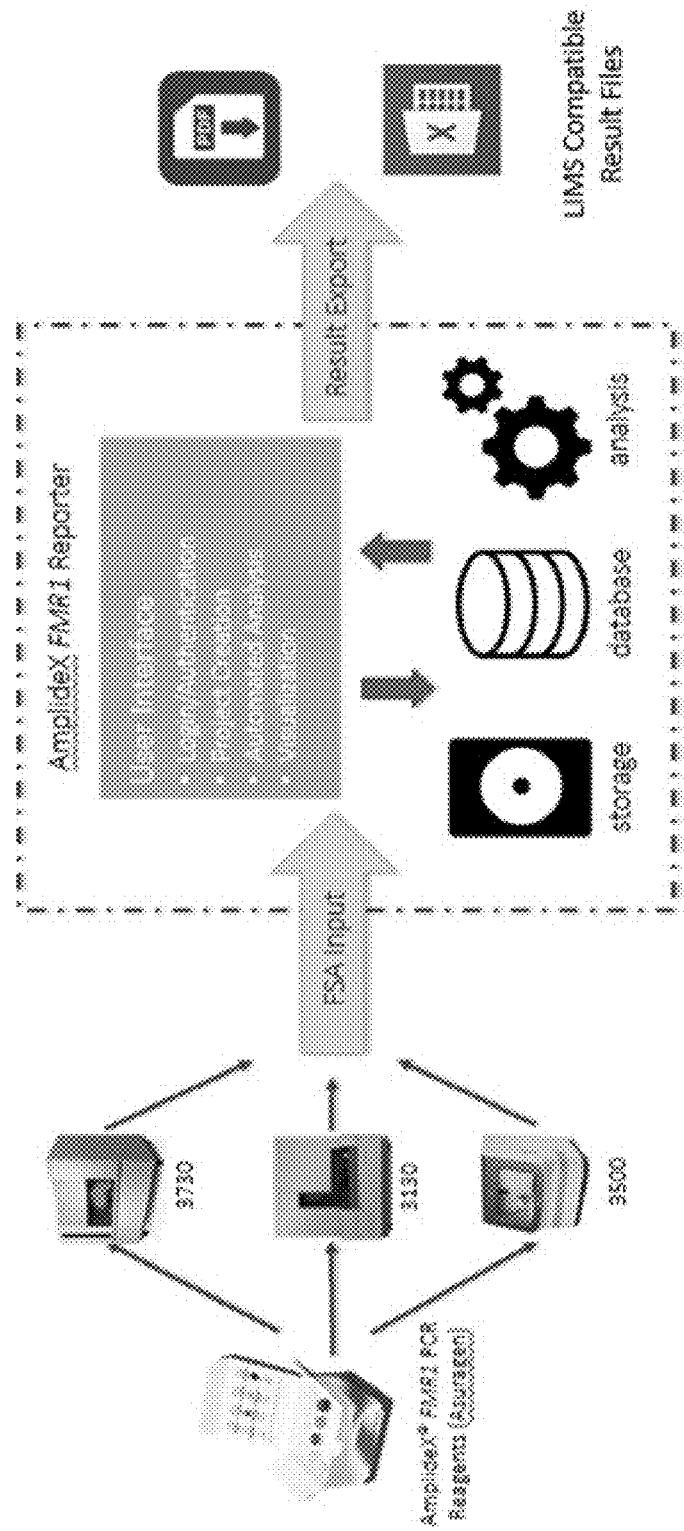
FIG. 16 shows a diagram of exemplary assay and software components.

PCR-based workflow for size analysis of the CGG-repeat region may be accomplished using the AmplideX™ FMR1 PCR assay (Asuragen Catalog No. 49402; U.S. Publication No. 2010/0209970). See FIGS. 9 and 16.

Example 2: Workflow for Sizing a Repeat Region of Nucleic Acid Using an Internal Standard A sizing method was developed to utilize the repeat profile associated with priming events along the CGG-rich region in the FMR1 gene. Since each peak in the capillary electrophoresis plot "repeat peak" corresponds to an adjacent priming event, i.e., an amplification product of one extra repeat in length, the length of the peaks in nucleotides can be estimated by assuming the size (in base pairs) of the first repeat peak (taking into account primer sequence length), then assuming that each repeat peak after the first is 3 base pairs longer than the previous peak. This information is used to generate a calibration curve that relates location in the fragment sequence analysis (FSA) signal (in sampling units) to fragment size (in base pairs).

Figure 10:
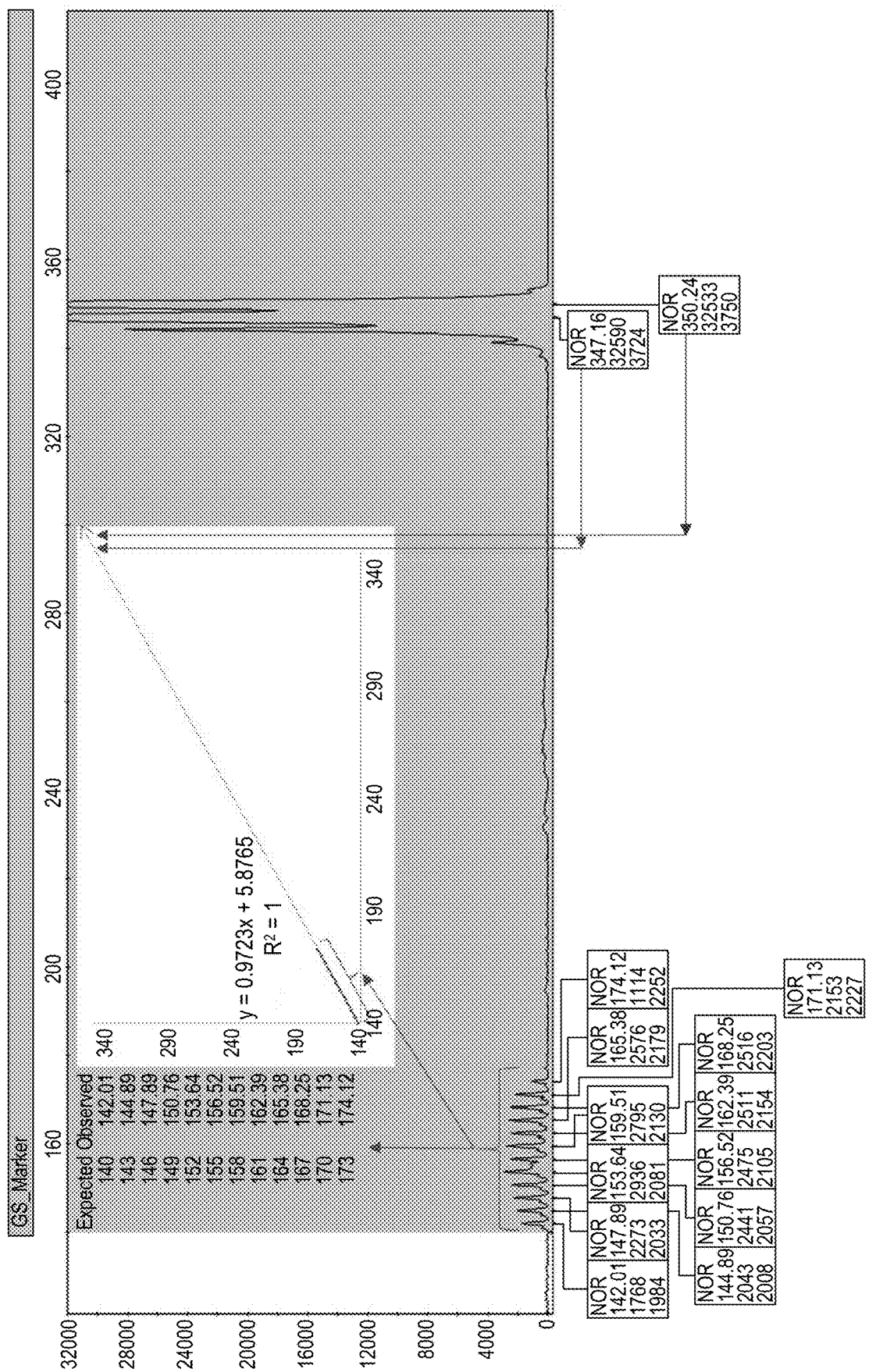
FIG. 10 depicts a graphic representation of the process by which repeat peak localization is utilized for sizing gene-specific products. The expected location of each repeat may be used to generate a calibration curve for sizing, either as a stand-alone sizing ladder or as a fragment mobility correction to an external sizing standard.

In detail, the algorithm for repeat peak identification works in several stages. First, the beginning of the repeat signal is detected using information about the window in which the repeat signal starts based on the sampling frequency of the instrument. Second, quantile-based analysis is used to determine the range in which the repeat signal starts and ends. Third, frequency-based analysis is used to determine repeat periodicity in sampling units. Fourth, the repeat periodicity is used to inform the window size for which repeat peaks will be called. Fifth, a quantile-based approach is used to derive a threshold at which repeat peaks should be called. Sixth, a sliding window is used to call single repeat peaks, where the called peaks for each window are defined as having a negative second-order derivative with the largest magnitude in the range. If no peaks are found or the signal falls below the threshold determined in the fourth stage, the location of the repeat peak as the center of the window may be extrapolated. As peaks are called, the size of the window based on the difference between repeat peaks in sampling units maybe adjusted. FIG. 10 depicts a graphic of the process by which peak location is utilized for sizing gene-specific products. The expected location of each repeat peak is used to generate a calibration curve for sizing. FIG. 10 was generated using AmplideX reagents in combination with the FMR2 set of custom primers (p/n 49541).

After repeat peaks are identified, the software may generate a model for sizing us cubic splines interpolation of all peak indices (in sampling units) against expected fragment lengths for the repeat peaks (in nucleotides), In some embodiments, the si zing standard may be piecewise, applying a first-order polynomial fit to the linear region of the gel, and a univariate spline fit to the nonlinear region of the gel.

Example 3: Automatic Gene-Specific Product Identification of Major Alleles

An algorithm developed to automatically generate FMR1 genotypes for this assay can be used in conjunction with the sizing methods. The algorithm takes a magnitude-based approach to identifying gene-specific products, and labels all allele peaks down to a specified threshold. The workflow for this algorithm involves identifying regions with a peak-like shape, having a first-order derivative of 0 and a negative second-order derivative, and ranking the regions by relative fluorescence units (RFU) magnitude. An optional step may involve providing gender as an input, returning the number of peaks required for each gender and automatically resolving numbers of alleles (i.e., for homozygous female samples). For full mutation analysis the repeat profile for expansion is analyzed using a quantile-based approach to assess present repeat peaks passed called repeats. If expansion occurs the expanded allele is reported. Gene-specific repeat genotypes are determined in the AmplideX software using the internally derived ladder.

Example 4: Automatic Gene-Specific Product Identification of Minor Alleles

In addition to major allele genotyping, a process for minor allele detection was established that enables lab-specific definitions of minor allele cut-offs. Since minor alleles and mosaicism are typically only clinically relevant if the phenomenon occurs in a clinically-relevant category, the algorithm was specifically designed to search for minor alleles in the pre- to full-mutation range. Specifically, the algorithm for minor allele detection may take the following steps: (1) from the ranked list of peaks detected in the major allele genotyping phase of the algorithm, determine if any excess peaks are >54 CGG repeats long, and (2) for those peaks, determine which (if any) have an RFU magnitude higher than a user defined threshold percentage of the largest gene-specific product identified in the signal. The threshold currently defaults to 10%, but can be specified as inputs to the algorithm.

Example 5: Application of Using Workflow for Sizing a Repeat Region

The performance of the algorithm discussed above was evaluated against a comprehensive set of 500 randomly-selected and previously-annotated clinical samples which span the entire FMR1 genotype range. Samples that passed QC criteria were genotyped using the methods described in the previous section, and accuracy was measured as the difference between expected and observed peak size (in repeat units). In addition, concordance between the ROX ladder, for example ROX 1000 size ladder, P/N: 145194 (an external reference standard) and internal sizing methods was evaluated using a correlation analysis across the sample cohort. Minor allele detection capabilities were also tested using a selected cohort of 7 samples with operator-identified mosaicism. For this, the algorithm was parameterized to call down to 5% minor allele sensitivity, and results were compared against the manually-sized minor alleles. Finally, the algorithm was tested using a 5% sensitivity control (Asuragen, P/N: 145303) to evaluate the analytical sensitivity and utility of the repeat profile for flagging expansions. This sensitivity control was composed of 95% short female normal and premutation alleles (CGG=30, 56) and 5% of an expanded allele (>200 CGG).

Figure 11:
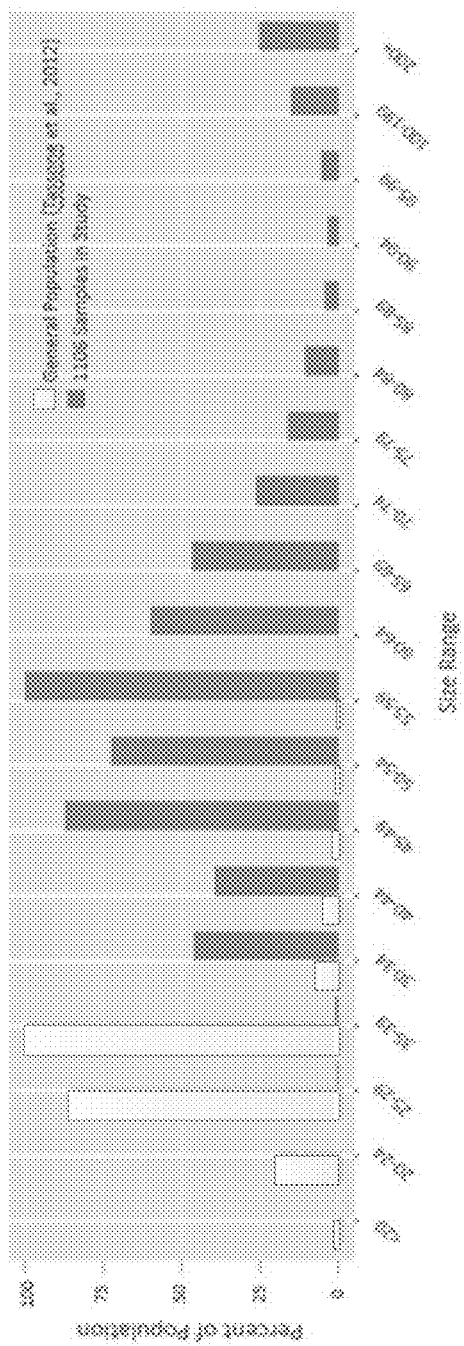
FIG. 11 depicts the distribution of FMR1 genotypes in the general populations in light grey compared to the distribution of genotypes in the 1106-sample validation dataset in dark grey.

FIG. 11 shows the distribution of patient FMR1 genotypes tested in the study, along with the published distribution of FMR1 genotypes in the general population (Tassone et al., 2012). The distribution of patients in the testing set was denser in higher size ranges to assess the sensitivity of the algorithm for genotypes with greater clinical relevance. Overall, 472 of the 500 samples passed QC thresholds for signal integrity, and were genotyped using the methodology described in the previous section. Embedded QC steps accurately identified 28 failed samples (5.6%), which upon visual inspection were confirmed to have either complete signal dropout (9 samples) or significant loss of repeat peak height (19 samples).

Figure 12:
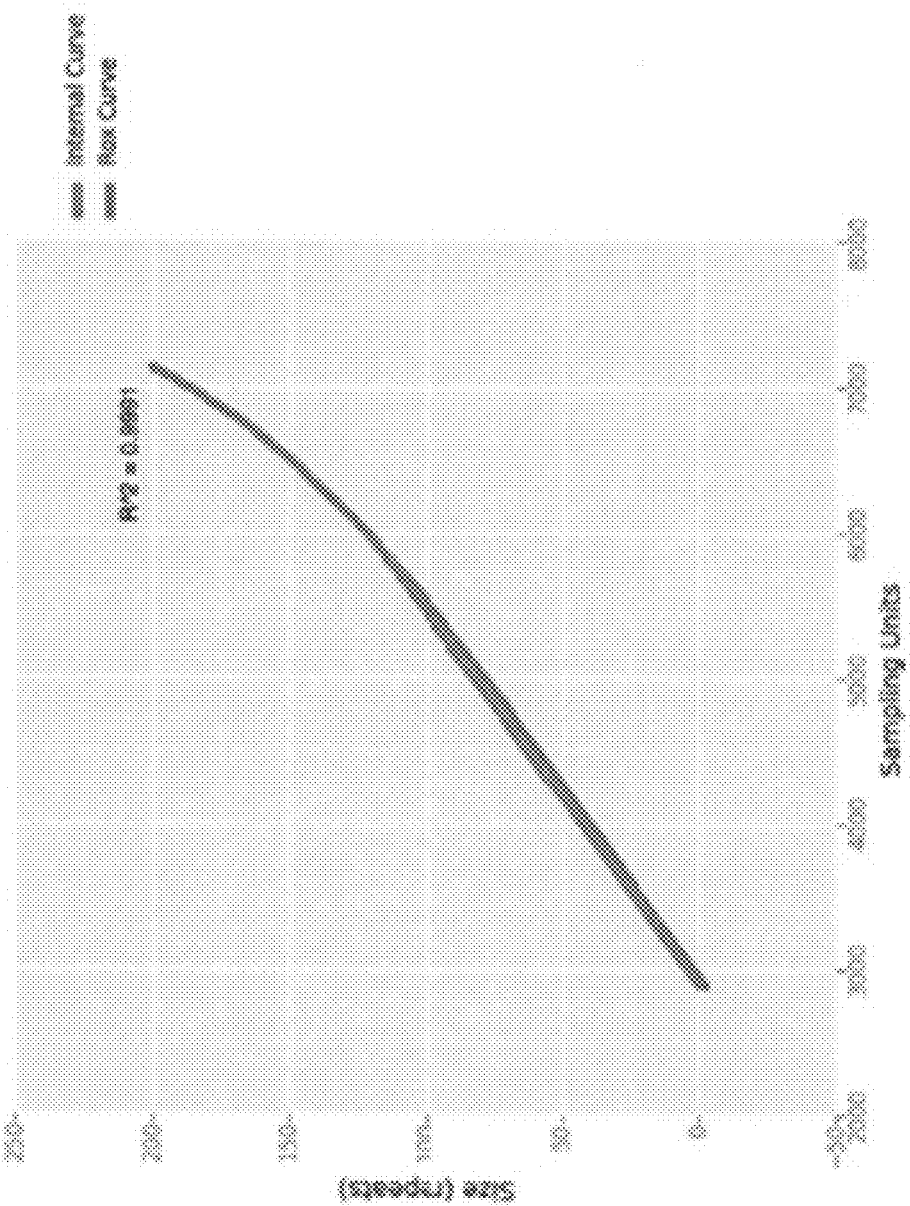
FIG. 12 depicts the concordance between repeat region lengths determined using an internally-derived sizing ladder and a sizing ladder derived from an external sizing standard called ROX ladder (ROX 100 Size Ladder, Asuragen P/N: 145194).

In addition, the repeat-peak sizing method was found to correlate with previously used methodology (using a ROX ladder) with $R^2>0.95$, suggesting a minimized need for external calibration components (ROX ladder and control samples) as a part of the AmplideX FMR1 workflow. FIG. 12 depicts an example of the concordance between ROX and internal sizing methods.

Figure 13:
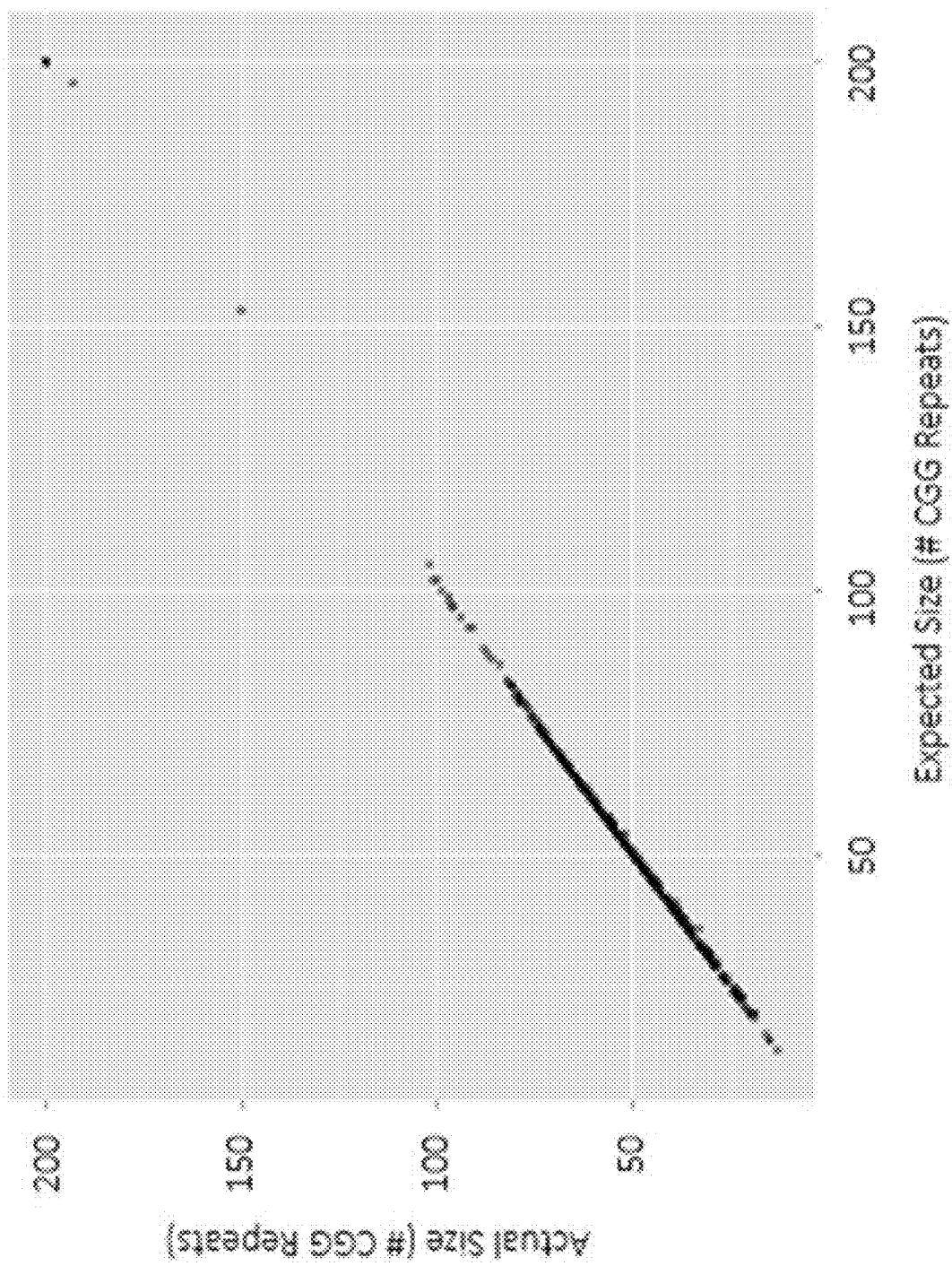
FIG. 13 depicts a comparison between manual and automated sizing of major alleles evaluated in a clinical set.

For the 472 samples that pass embedded QC, the algorithm successfully identified all major (non-mosaic) alleles (855), flagging alleles of greater than >200 repeats as full-mutations. Alleles having greater than 200 repeats were accurately positioned, using an internal sizing method, to within ±1 CGG of their previously reported size (determined independently using manual analysis). Table 2 details genotyping accuracy with respect to clinical mutation category. Overall, all samples with the exception of 2 were correctly identified in their expected category, with the 2 incorrectly labelled samples being genotyped to with ±1 CGG of their previously reported size. FIG. 13 shows genotyping accuracy in greater detail, depicting the expected versus observed FMR1 genotypes for all non-mosaic peaks in the cohort. FIG. 13 depicts the correlation between manual and automated sizing of all major alleles (855) in the feasibility study. FIG. 13 shows that the automated FMR1 genotyping workflow produced concordant results with the manual assignment based workflow.

TABLE 2

Genotyping accuracy with respect to clinical mutation category.

| | | Automated Analysis | | | |
|---|---|---|---|---|---|
| | | Normal (0-44) | Intermediate (45-54) | Pre-Mutation (55-200) | Full-Mutation (>200) |
| Manual Analysis | Normal (0-44) | 162 | *6 | 0 | 0 |
| | Intermediate (45-54) | 0 | 295 | *9 | 0 |
| | Pre-mutation (55-200) | 0 | *1 | 527 | 0 |
| | Full-Mutation (>200) | 0 | 0 | 0 | 35 |

*within ± 1 CGG of manually annotated size

Figure 14A:
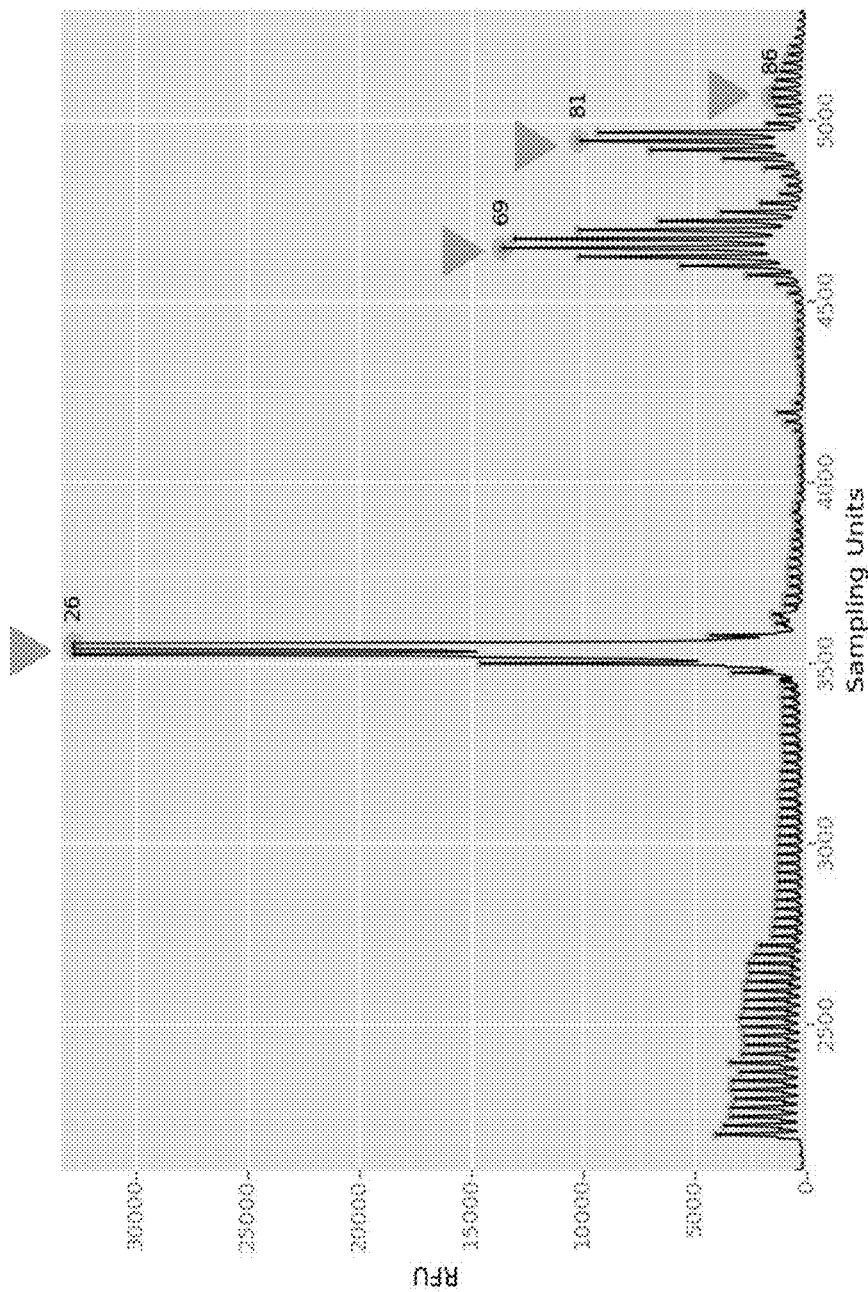
FIGS. 14A and 14B depict diagrams detailing the analytical sensitivity of algorithm to gene-specific products. Arrows indicate calls made by automated sizing.

In addition, the process for minor allele identification correctly identified all minor alleles from the set of 7 manually annotated minor alleles to within +1 CGG of their manually-derived size. FIG. 14A shows a diagram detailing minor allele detection capabilities. All minor alleles in the figure were automatically detected by the FMR1 software and labelled concordantly with manual analysis. The figure also depicts the sensitivity-adjustment functionally developed for user-specific minor allele detection.

Figure 14B:
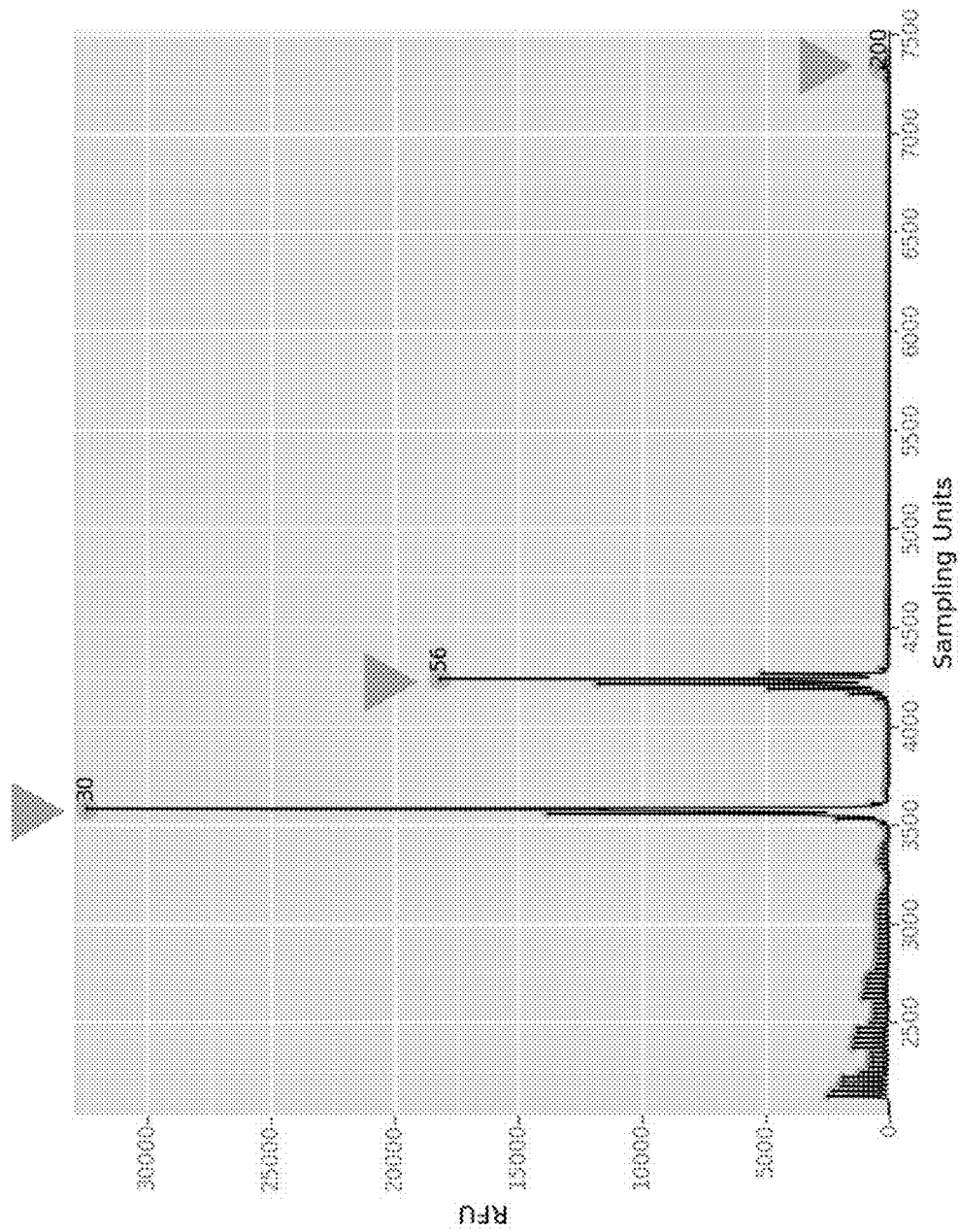

Finally, the sensitivity control sample was accurately genotyped and flagged as an expanded allele. FIG. 14B depicts the algorithm's labelling of gene-specific products.

Figure 15A:
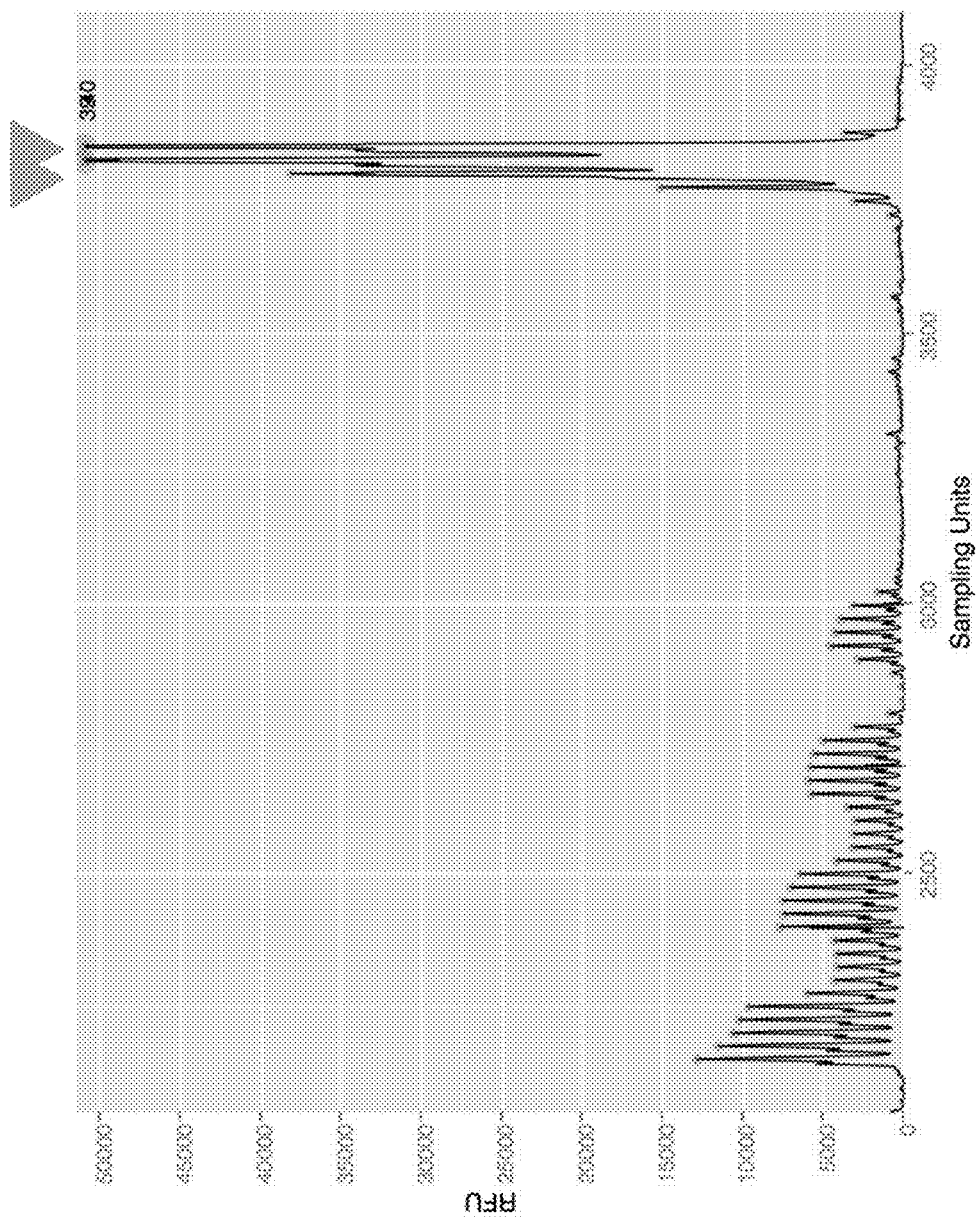
FIGS. 15A and 15B depict diagrams detailing analytical sensitivity of the assay across FMR1 genotype ranges. Arrows indicate calls made by automated sizing.
Figure 15B:
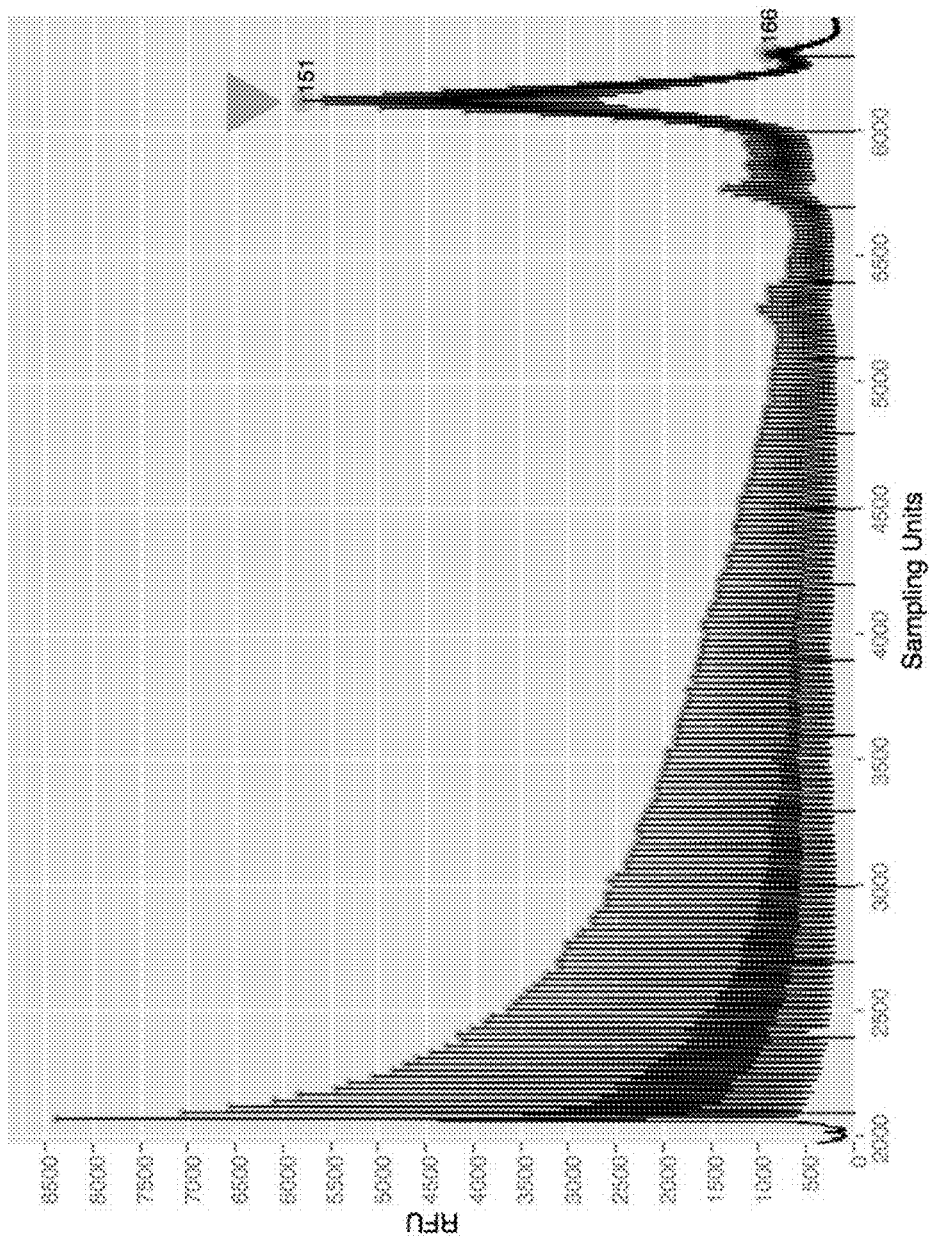

FIGS. 15A and 15B shows a diagram detailing analytical sensitivity of the algorithm across FMR1 genotype range. Arrows indicate calls made by automated sizing. FIG. 8 depicts the AmplideX PCR/CE FMR1 Reporter, a highly accurate, automated FMR1 analysis engine and software interface was designed that improves the efficiency and consistency of capillary electrophoresis-based assays targeting the CGG-repeat region of the FMR1 gene, for example. This software was tested on >1000 clinical samples processed using AmplideX® FMR1 PCR reagents and demonstrated 100% agreement with manual genotyping. The software also demonstrated high sensitivity to detect low-abundance gene-specific products. This software is likely to improve analysis times for FMR1 assay workflows by greater than two orders of magnitude, and has the potential to improve inter-operator consistency in resolving CE profile ambiguities.

Example 6: Detecting Failed Samples

An automated strategy of flagging samples for re-analysis was developed to detect signal dropout by using a quantile-based analysis, in a way that is robust to signal artifacts that can occur toward the beginning of the signal (e.g. small first peak, AGG interruptions). The algorithm works by calculating the 95th quantile of the RFU magnitude (signal) and the 5th quantile of the RFU magnitude (background), and fails samples where the difference between those values falls below 200 RFU. The 200 RFU threshold for failing a sample was empirically determined using a set of control samples that were titrated from normal input amounts down to a 12.4 pg genomic DNA input amount. The threshold value was determined by considering the last input amount that resulted in correct genotype calls, and was calculated as the mean separation between signal and noise for those samples. In addition to identifying signal dropout, an algorithm was developed to identify prematurely stopped runs by recognizing the absence of ROX ladder peaks in the higher size ranges. If the number of identified ROX peaks is lower than expected, the algorithm flags the sample as having incomplete data. This can potentially guard against errors that might result in incorrectly genotyped samples with clinical relevance.

Example 7: Identifying Mislabeled ROX Peaks

Figure 17:
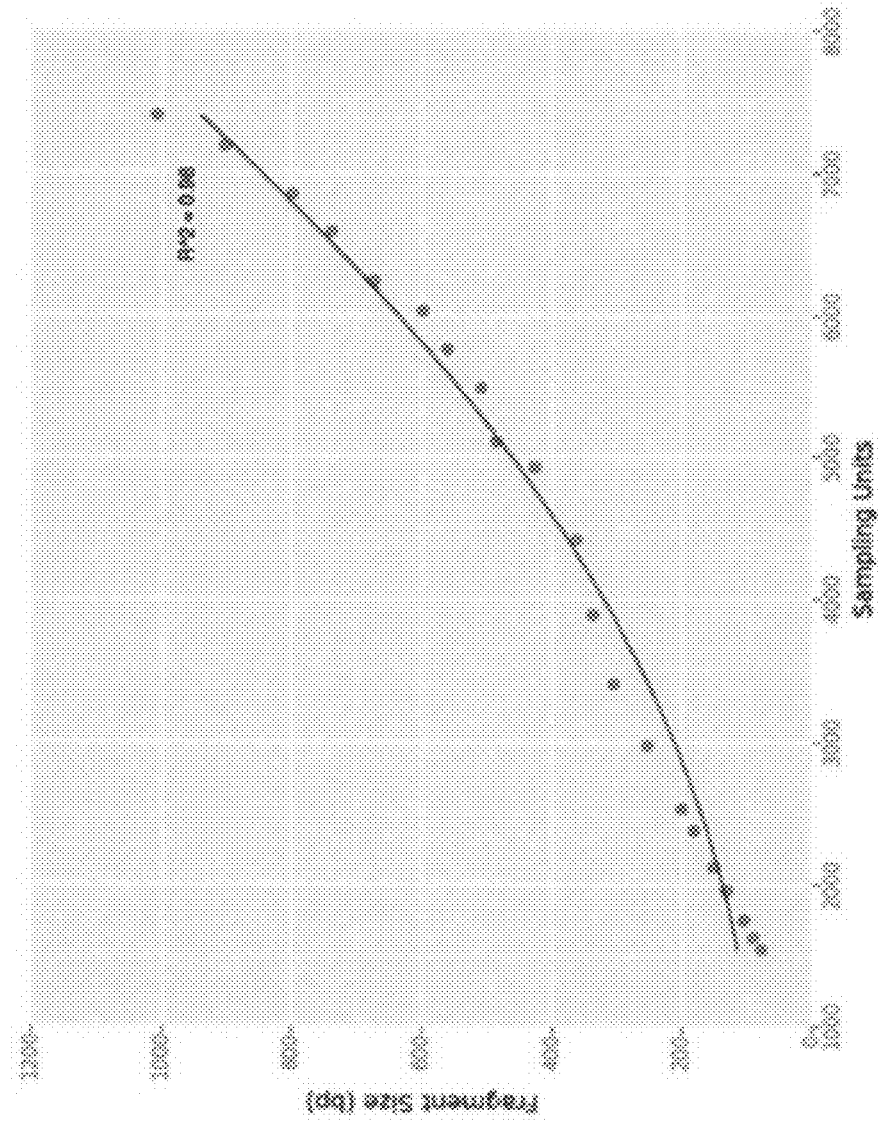
FIG. 17 depicts an external ladder, ROX profile depicting certain assays.

Along with automated checks for signal integrity, an algorithm was developed to identify mislabeling issues in the ROX channel which could potentially contribute to minor sizing errors. See FIG. 17 for a depiction of how mislabeling issues could contribute to incorrect sizing. The dots in the figure demonstrate the locations of expected ROX ladder peaks in the signal, and the black line demonstrates size interpolation using a second order polynomial. The correlation between these actual and interpolated points serves as a good indicator of gel integrity, and can be used to identify mislabeling issues. Although these small mislabeling issues can affect interpolative sizing via ROX ladder, they do not have as great of an effect on sizing via repeat profile, since there are many more points to use for interpolating a sizing ladder via repeat profile. The $R^2$ value was calculated by correlating the sizes predicted by a second-order polynomial fit to the data against the actual size. Deviation from $>=0.98R^2$ indicates that there could have been mislabeling issues that may contribute to incorrect sizing.

Example 8: FMR1 Sizing Analysis 8.1. Workflow Overview

The current workflow for FMR1 CGG analysis is streamlined through the point at which genotypes are interpreted from capillary electrophoresis data. Manual interpretation is a significant bottleneck for high-volume testing, and an automated algorithm has the potential to drastically improve the entire process. In this study, an automated solution to FMR1 analysis was developed to generate highly accurate FMR1 sizing results. An overview of the components of the algorithm is described in detail within this section. At a high-level, the algorithm works in several stages. The first stage of the algorithm extracts raw data from fragment sequence analysis files, and performs pre-processing to normalize the differences across samples run with different configurations. The second stage involves parameterizing a sizing ladder for converting from location units in the signal (analogous to distance traveled in POP7 gel) into base-pair sizes, using components internal to each sample. The final stage of the algorithm involves parameterizing a model for deconvolving amplification from different primer sets in the assay, and using that model to identify genotype peaks.

8.1.1. Fragment Sequence Analysis (FSA) File Parsing

The AmplideX® FMR1 PCR assay is designed to be run in conjunction with the Applied Biosystems family of Genetic Analyzer instruments (3130/3500/3700), all of which export data in a proprietary format maintained by Applied Biosystems. This format is referred to as the Fragment Sequence Analysis format and contains fluorescence data from capillary electrophoresis experiments, encoded according to a proprietary set of specifications described in "Applied Biosystems Genetic Analysis Data File Format, 2009" and hereby incorporated by reference in its entirety. In order to directly access this file format, a specialized parser was designed to decode and organize the information into a JSON-based format that is easy to programmatically access and manipulate. This parser heavily utilizes an open-source module for the perl programming language called Bio::Trace::ABIF. The parsing software has been validated on >1000 samples run across different Genetic Analyzer Instruments (3130/3500/3700), and has been shown to be exactly concordant with unprocessed fluorescence data viewed through GeneMapper, the current standard for accessing the Fragment Sequence Analysis format.

8.1.2. Preprocessing within the FMR1 Sizing Analysis 8.1.2.1. Signal Smoothing

Since the AmplideX® FMR1 PCR assay relies on a capillary electrophoresis-based readout for data interpretation, the assay was subject to convolution by signal artifacts that are systematically present on CE instruments. As a first step in processing, a Savitzky-Golay filter was applied to each of the channels in order to smooth the data. This allowed for the assumptions made by the algorithm in downstream processes to be simplified, and also increased robustness in post-processing operations.

8.1.2.2. Baseline Normalization

After smoothing, each channel was then normalized to account for improper instrument calibration. To normalize each channel, the signal was subtracted by the 10th percentile of RFU values in the signal. The 10th percentile was chosen empirically because it robustly represented the lower values in the signal, without being affected by sharp negative fluctuations commonly encountered. Alternate suitable values would similarly represent the lower values in the signal without being affected by sharp negative fluctuations.

8.1.2.3. Air-Bubble Contamination Removal

As a pre-processing step to the AmplideX® FMR1 algorithm, air-bubble artifacts were identified and removed. Such air-bubbles may produce large spikes in signal intensity that may be interpreted as gene-specific products or ROX channel sizing peaks in a way that produces incorrect results. But the presence of air-bubbles capillary tubes during a CE run resulted in fluorescence affects all of the channels to a similar degree of magnitude. The air bubble artifacts were identified and removed by taking advantage of this multi-channel presence of noise peaks. For each of the sites where an air bubble was found, the air bubble was removed by simulating Gaussian noise between the peak shoulders. The mean and standard deviation for the noise was determined from the region surrounding the air bubble.

8.1.2.4. Signal Saturation Resolution

Another preprocessing step involved extrapolating peak shape over regions where signal saturation occurred in the FAM channel. Saturation occurred when products fluoresced at a luminescence greater than the collection limit of the instrument RFU sensors, resulting in a loss of information on peak shape. However, since the wavelength spectra for collection allows for bleed-over across channels, peak shape for saturated regions can be extrapolated from channels capturing fluorescence at a similar wavelength. In identified regions of saturation, the RFU values from the NED channel were added onto the HEX channel:

8.1.3. Automated Sizing Ladder Calibration

The current gold-standard for fragment sizing in capillary electrophoresis experiments requires the use of externally added dye-labelled PCR products of known sizes, which produce fluorescence peaks in a band outside of the frequency spectrum produced by AmplideX® FMR1 PCR products. These fluorescence peaks can be identified independently of target products generated by the assay and are used to generate a calibration curve that relates location in the fragment sequence analysis signal (in sampling units) to fragment size (in base pairs). Although the process of identifying these fluorescence peaks is handled automatically in the GeneMapper software, it often requires manual inspection to correct mislabeled peaks, which can significantly increase the time required to perform AmplideX® analyses. To improve on this, an algorithm was developed to automatically identify and label ROX fluorescence peaks in a way that is robust to the mislabeling phenomena that impedes GeneMapper-based workflows. Additionally, the algorithm was developed to extend easily to arbitrary sizing ladders (ROX 1000, ROX 200) for use in future assay development.

8.1.3.1. Bleed-Over Artifact Removal

A first stage involve of analysis included removing bleed-over artifacts from the HEX channel that can convolute the assignment of expected sizes to ROX fragment peaks. In order to detect these bleed-over artifacts, the algorithm identified locations above an empirically-derived, instrument-specific threshold in the HEX channel, and then simulated Gaussian noise mimicking the signal background over that region.

8.1.3.2. ROX Fragment Peak Calling

A second stage involve of analysis included calling a set of candidate ROX fragment peaks, and removing peak artifacts that are likely false-positive peak calls. To identify the candidate set of ROX fragment peaks, a sliding filter across the data that was 500 location units wide was run. For each window: (a) the mean and standard deviation of the signal within that range was taken and (b) peaks that are over 3 standard deviations above the mean noise level (noise profiles for CE instruments are assumed to follow a Gaussian distribution) were called. After detecting these candidate peaks, proximal false positive peaks caused by "shoulder" artifacts were resolved by selecting the largest peak in a window around selected peaks.

8.1.3.3. ROX Fragment Peak Association

A third stage of analysis included using an iterative approach to choose the most likely peaks associated with labelled fragment peaks. This approach took advantage of the low-noise profile associated with larger fragment sizes for selecting initial conditions. In short, all expected ROX fragment sizes greater than 500 bp were automatically associated with the furthest (by distance in the capillary) set of candidate peaks. A linear sizing ladder for all labelled ROX peaks between 500 and 700 bp was then fitted using a 1st order least-squares regression and used to predict the location of the next (sub-500 bp) fragment peak. The candidate peak closest to that predicted location was then labelled with that fragment size, and the linear sizing ladder was re-fitted to include that data point. The algorithm iteratively labels candidate peaks with ROX peak fragment sizes in this fashion, continuously training with new data points in a way that increases the accuracy of peak association in the noisier region of the gel. This iterative approach has been shown to be more specific than current methods (GeneMapper, GeneMarker) in ignoring signal artifacts in the ROX channel that can contribute to improper sizing ladder parameterization, and is also robust to mistaking primer-dimer peaks as ROX fragment peaks.

8.1.3.4. Sizing Ladder Parameterization

A piecewise sizing standard was then generated using the final sizing ladder. The piecewise model employed a linear model for ladder peaks below 650 bp, and a univariate spline model (similar to the local southern method (see, *Analytical Biochemistry* 100(2):319-323 (1979)) for ladder peaks above 650 bp. To parameterize a final smoothed sizing ladder, the piecewise model was used to resample 100 evenly-spaced points with location unit to fragment size associations. These resampled points were fit to these data using a univariate spline model in order to generate a smoothed final version of the ladder.

8.1.4. Sizing Ladder Mobility Correction

ROX fragment mobility in capillary electrophoresis differs from FMR1 fragment mobility, because of the GC-rich nature of FMR1 fragments relative to the nucleotide-balanced nature of ROX fragments. In order to account for these differences, mobility correction factors were parameterized from the FMR1 repeat signal and applied to the sizing ladder derived from the ROX channel. There were several steps involved in this process: 1) identification of the start and end locations of the repeat signal, 2) labelling of all repeat fragment peaks, 3) application of the mobility correction.

8.1.4.1. FMR1 Signal Window Parameterization

As a precursor to labelling repeat peaks, the region of interest of the signal was determined. The ROX ladder was used to predict an approximate location for the beginning of the repeat profile. If the ROX ladder parameterization failed or the resulting fit did not match ROX QC criteria (see section 8.1.6), then the following steps were employed.

A summation transformation on the data with a window size of 200 location units was used. For the largest peak in that transformed signal (caused by primer-dimer amplification events), the peak shoulders were identified. From the right-most shoulder, a transformation was applied that calculated the dominant frequency of the signal within 100 location unit windows. The location of the first window in which the dominant frequency of the signal was within an empirically-derived tolerance was used as the approximate beginning of the repeat profile.

Once the approximate location of the repeat region was identified, the exact repeat start site was determined by identifying the first location greater than the 85th percentile of the signal within a 1000 location unit window from the approximate repeat start site.

The end location of the repeat region was identified using a transformation that applied a 90th percentile filter across the signal with a window size of 100 location units. After the transformation was applied, the signal end location was selected as the last transformed region that falls above an empirically-derived, instrument-specific threshold.

8.1.4.2. Repeat Primer Peak Calling

After the start and end locations of the signal were identified, the analysis proceeded by determining all amplification peaks in the signal generated by the repeat primer set. These peaks were then associated with sizes resulting from expected priming events, and a linear ladder fit was generated. At a high-level, the repeat peaks were called used a window derived from the periodicity of the signal to iteratively call repeat peaks, and the window was adjusted as periodicity shifts in the signal, and peak location were interpolated where repetitive peaks were suppressed (i.e. AGG interruption sites).

A Fourier Transform on a 1000 location unit window from the start site was used to identify the periodicity of the repeat profile. The expected starting distance between peaks was calculated using the inverse of the periodicity. The 25th percentile of a 2000 location unit window from the start site was used to derive a threshold for interpolating peak location.

To determine the length of the repeat profile (between the start and end locations determined above), the next peak call peaks that were above the repeat threshold were iteratively chosen by predicting a window containing the approximate peak location and selecting the largest peak in that range. The window for selecting peaks was calculated as ½ of the size of the distance between peaks (as determined by the periodicity of the signal).

8.1.4.3. Sizing Ladder Mobility Correction

After all peaks for the repeat profile were identified, they were labelled with expected fragment sizes and used to generate a linear sizing ladder. This linear sizing ladder served as a size-corrected ladder that the ROX ladder can be mapped to using an affine transformation. Mapping via affine transformation ensured that both the linear and non-linear components of the sizing ladder had mobility corrections applied to them.

8.1.5. Genotype Peak Identification and Sizing

An important piece of the sizing analysis was genotype peak identification and sizing. Since signals exhibit both repeat-segment and gene-specific amplification, identification of genotype peaks is nontrivial and involves steps to deconvolve these two components of the signal. Additionally, challenging genotypes that do not present as normal genotype peaks were identified throughout the process.

8.1.5.1. Repeat Profile Background Estimation

A first step in identifying gene-specific amplification events involved parameterizing a background model for deconvolving the signal contribution of repeat amplification events from the signal contribution of gene-specific amplification events. Among the signal artifacts that make this process difficult, the most significant were: (1) AGG interruptions in the FMR1 repeat region that significantly diminished the magnitude of the repeat profile, creating "gaps" in the profile that must be ignored while creating the background model; and (2) Gene-specific product peaks significantly deviating from the repeat component of the signal, but lacking characteristics that would allow a frequency-based filtering approach to deconvolution.

The deconvolution process modeled the "background" of the repeat profile as the height of the repeat signal within a given window. For AGG interruptions, the "background" was at the level of local repeat peaks proximal to the AGG interruption. For gene-specific product peaks, the "background" was similarly at the level of local repeat peaks proximal to the gene-specific deviations in the signal.

The analysis included the following steps to generate the background model. For all of the peaks in the repeat signal, a filter added the median and interquantile range of the data over a window size of 11 repeats. This filter was designed to capture the height of repeat peaks in the window, but was robust to large fluctuations in the repeat signal caused by AGG interruptions and gene-specific products. For the resulting signal, a Savitzky-Golay filter with a window size of 7 repeats to smooth the data was used. Any "peaks" in the resulting signal were interpolated linearly through the peak shoulders.

8.1.5.2. Genotype Peak Identification Using Dynamic Threshold

A dynamic threshold was derived from the deconvolution model above, by applying a dynamic scaling approach that makes calling in the lower size ranges more specific, and calling in the higher size ranges more sensitive. At a high-level, the scaling approach applied a piecewise scale factor to the deconvolution model, which decreased from 3 to 1.5 in the region between 0 and 120 repeats, and then remained constant at 1.5 after 120 repeats. The genotype peak set was determined using this threshold in accordance with the method above for identifying regions with peak-like shape. Gene-specific product peaks were converted to repeat sizes using the sizing ladder derived in a previous section, and converted to repeat numbers using the known fragment size of non-repeat components from gene-specific amplification products (in this case 240 bp).

8.1.5.3. Resolution of Challenging Genotypes

After the initial pass at determining the genotype peak set G, challenging genotypes that do not present as normal gene-specific product peaks (i.e. homozygous female samples, n/n+1 genotypes, expanded samples) were resolved. Homozygous female peaks were resolved using supplied sex information, and singly-called peaks were resolved into a homozygous genotype for female samples. Samples with proximal genotypes (n/n+1) in the normal range were resolved by using repeat peaks next to genotype peaks. When the repeat peak occurred adjacent to a genotype peak, and the signal intensity of the repeat peak was within 90% of the height of the adjacent genotype peak, the repeat peak was also labelled as a genotype peak. Finally, when no genotype peaks were identified for a sample, but the repeat profile showed expansion, then the sample was labelled as an expanded sample. This usually occurred for male samples lacking gene-specific product peaks in which the repeat profile expanded well beyond 200 repeats.

8.1.6. Automated Embedded Quality Control

Several quality-control measures were used to prevent misinterpretation of results. There were two categories of quality-control measures. No genotype calls were produced for samples failing the first category of quality-control measures (Sizing Ladder QC, Signal Magnitude QC, and Contamination QC). Genotype calls for samples failing the second category of quality-control measures (Minor Allele Sensitivity QC) were interpreted with greater skepticism. This second category should protect users from making genotype calls not reliably supported by their data.

8.1.6.1. Sizing Ladder QC

The Sizing Ladder QC verified that the sizing ladder was derived correctly and matched expectations with respect to internal calibrators. This measure combined three different criteria, each of which must be satisfied for the sample to pass. First, the coefficient of determination (R2) for the ROX ladder fit against ROX ladder peaks must be greater than 0.98. Second, the coefficient of determination for the internal ladder fit against internal ladder peaks must be greater than 0.98 Third, the coefficient of determination for the ROX ladder fit against the internal ladder fit for evenly spaced points throughout the fit must be greater than 0.98. These coefficient of determination thresholds were determined empirically from an independent training set, by selecting a level that accurately discriminated between samples that produced incorrect sizing and samples that produced correct sizing.

8.1.6.2. Signal Magnitude QC

The Signal Magnitude QC verified that the samples underwent sufficient amplification. Samples with poor amplification violate assumptions of the algorithm during processing and could potentially result in incorrect or false-negative genotypes being reported/missed. At a high-level, the algorithm verifies that there is a sufficient signal-to-noise ratio for the start of the repeat profile against the noise-level of the instrument proximal to the start of the repeat profile. The SNR threshold for this QC was determined empirically from the independent training set, by selecting a level that accurately discriminated between samples that produced incorrect sizing and samples that produced correct sizing.

8.1.6.3. Contamination QC

The Contamination QC verified that samples did not undergo off-target amplification, or include amplification artifacts related to improper sample preparation, which may contribute to incorrect genotypes reporting. Samples failed this QC when a gene-specific product peak was identified in a range that cannot be produced using the gene-specific primers. For example, when the repeat number derived for a gene-specific product peaks was less than 0 repeats (or equivalently less than 240 bp), then the sample was flagged as having contamination.

8.1.6.4. Minor Allele Sensitivity QC

The Contamination QC verified that samples had sufficiently low background noise for the chosen minor allele calling thresholds. This QC depended on the ratio between the background noise of the instrument and the largest genotype peak in the sample. When the ratio between the noise level in the signal and the largest genotype peak exceeds minor allele frequency, then minor alleles at that frequency cannot be accurately identified, and the sample is flagged with an "at risk" QC that users should interpret with more rigor.

8.1.7. FMR1 Sizing Performance

The performance above FMR1 sizing analysis was tested on several large cohorts across multiple instruments. For each of these studies, the algorithm correctly flagged expected QC failures and sized 100% of QC passing samples in accordance with assay guidelines. Assay guidelines for sizing were defined as +/−1 repeat for genotypes <70 repeats, +/−3 repeats for genotypes <120 repeats, and +/−5% of the repeat number for genotypes >=120 repeats. In addition, low-level mosaic peaks were detected for a number of samples that were identified by operators as having mosaic peaks. Samples failing QC were independently verified as deserving a failure status by trained manual operators. Truth data in this study were generated by trained operators via manual sizing through GeneMapper software. Furthermore, the distribution of genotypes tested in the study only differed slightly from genotypes expected in the normal population. The distribution of genotypes in this study was purposefully enriched with clinically-relevant alleles in the intermediate, permutation, and full-mutation range, in order to stress-test the algorithm for cases in which genotyping accuracy has a greater clinical impact.

8.1.8. Sally Nolan Performance Study

Figure 18A:
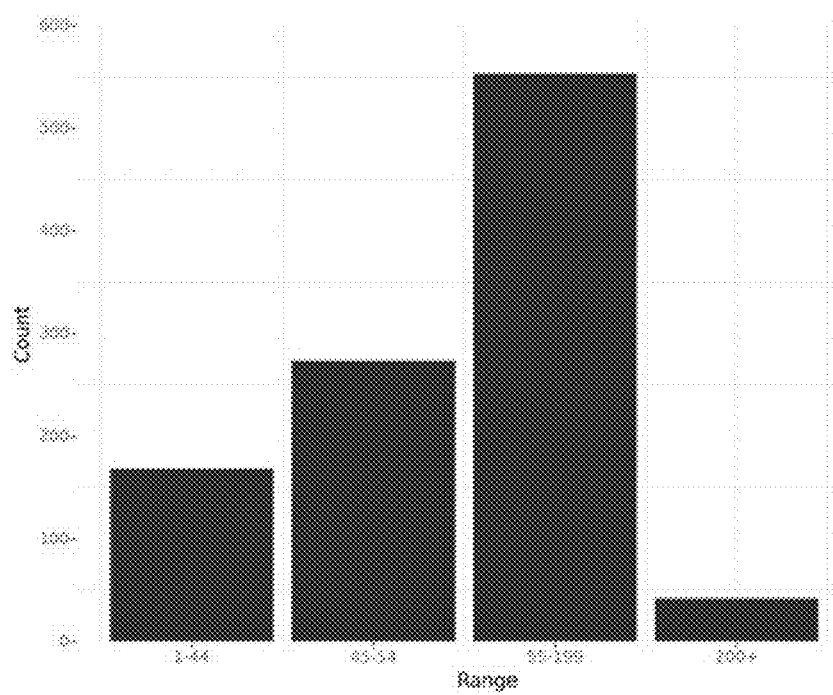
FIGS. 18A and 18B depict the results of testing the automatic sizing analysis of a large (n=1106) set of clinical samples.
Figure 18B:
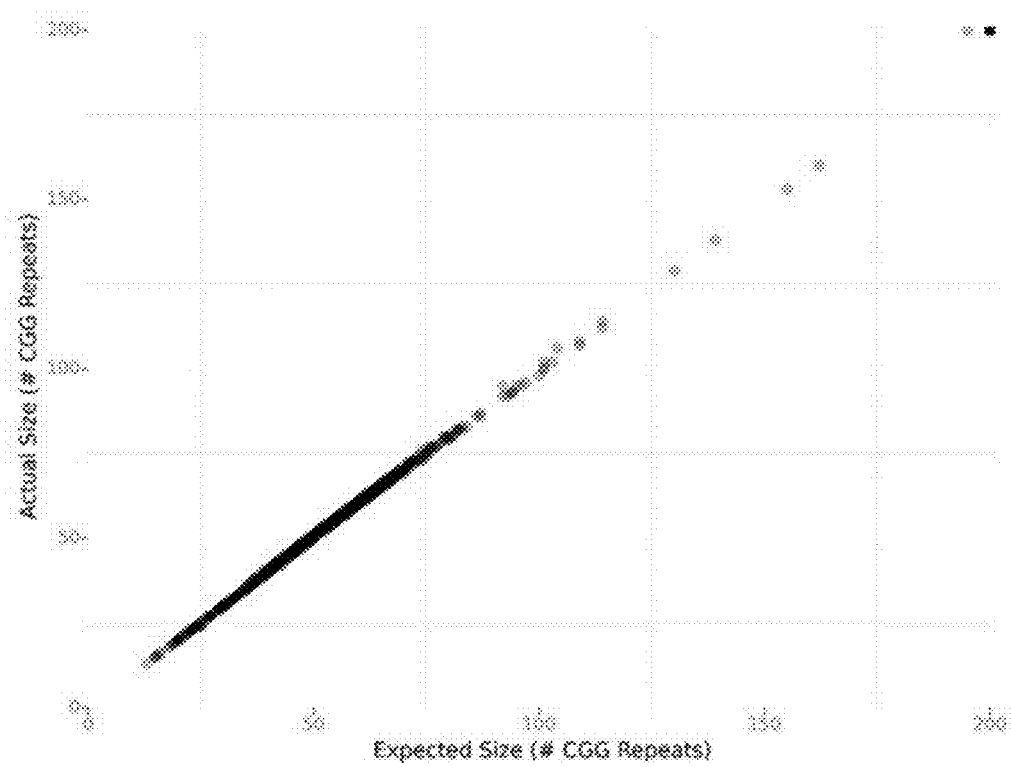

The Sally Nolan sample set was generated on a 3500 CE instrument, with normal inputs and conditions. This was designed to test the algorithm at an external lab, where input amounts are in accordance with normal usage of the assay. A total of 1040 samples were evaluated in this study, and 100% of genotypes for samples passing QC were accurately sized in accordance with assay guidelines. FIG. 18A shows the genotype distribution of samples in the study. FIG. 18B shows a comparison between automated and manual genotypes produced for assay results, and Table 3 details a comparison between manual and automated categorical calls.

TABLE 3

Categorical performance table for Sally Nolan sample set. All discrepancies between manual and automated assignment of clinical category were resolved by an independent operator as either being near mutational boundaries but within sizing guidelines for the assay, or resolved as having a low-level mosaic peak not originally labelled in the truth set.

| | | Manual Analysis | | | |
| --- | --- | --- | --- | --- | --- |
| | | Normal (0-44) | Intermediate (45-54) | Pre-Mutation (55-200) | Expansion (>200) |
| Automated Analysis | Normal (0-44) | 147 | 0 | 0 | 0 |
| | Intermediate (45-54) | 10 | 237 | 0 | 0 |
| | Pre-mutation (55-200) | 0 | 16 | 476 | 0 |
| | Expansion (>200) | 0 | 0 | 1 | 18 |

8.1.9. Multi-Instrument Rush Input Amount Study

Figure 19A:
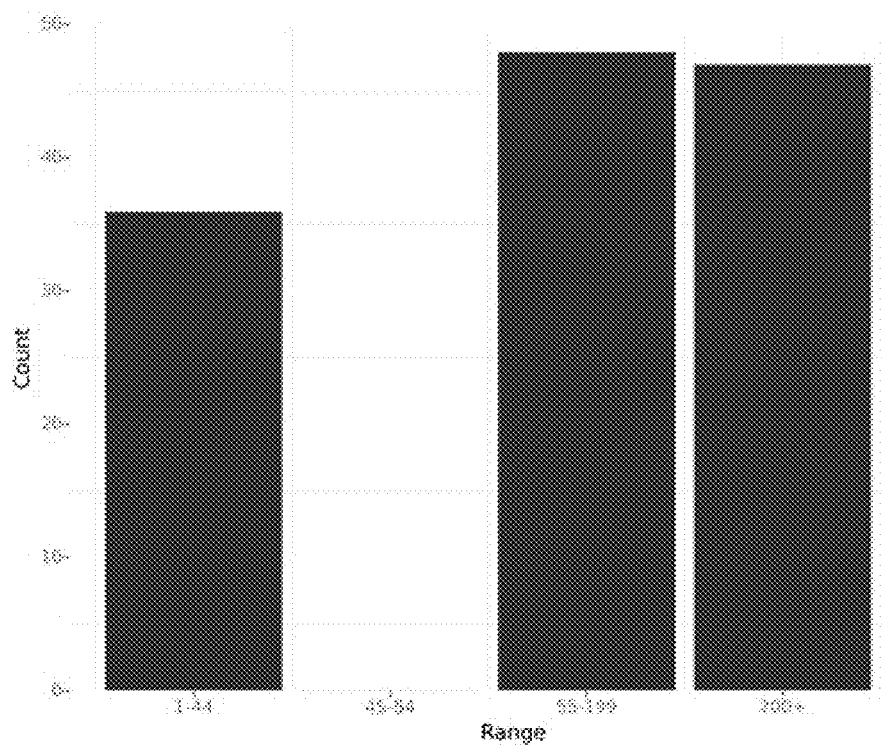
FIGS. 19A and 19B depict the results of multi-instrument RUSH input amount testing.
Figure 19B:
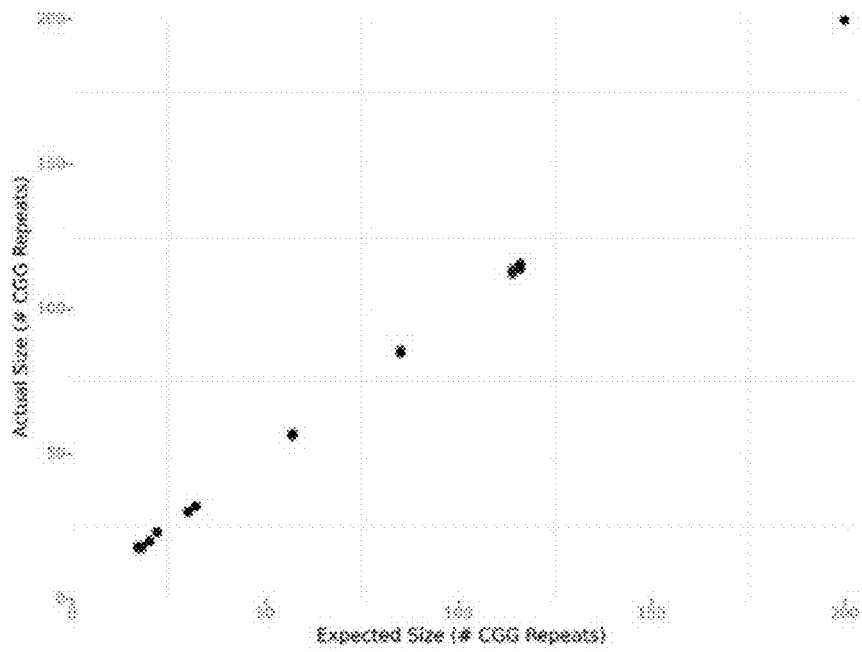

For this performance study, the RUSH set of samples (commonly used in testing the assay for the diverse distribution of genotypes and sample features) were run at different input amounts, in order to test the robustness of the assay to operator error. In addition, each input level was run on three different instruments to test the multi-instrument capabilities of the assay. Input levels were 100 ng/µl, 20 ng/µl, 4 ng/µl, and 0.8 ng/µl, which span normal input amounts for the assay (20 ng/µl) on the high and low end. A total of 31 samples were evaluated in this study, and 100% of genotypes for samples passing QC were accurately sized in accordance with assay guidelines. FIG. 19A shows the genotype distribution of samples in the study. FIG. 19B shows a comparison between automated and manual genotypes produced for assay results, and Table 4 details a comparison between manual and automated categorical calls.

TABLE 4

Categorical performance table for study. Each unique sample/input amount in the study was run three times across different instruments (3130, 3730, 3500).

| | | Manual Analysis | | | |
| --- | --- | --- | --- | --- | --- |
| | | Normal (0-44) | Intermediate (45-54) | Pre-Mutation (55-200) | Expansion (>200) |
| Automated Analysis | Normal (0-44) | 30 | 0 | 0 | 0 |
| | Intermediate (45-54) | 10 | 0 | 0 | 0 |

TABLE 4-continued

Categorical performance table for study. Each unique sample/input amount in the study was run three times across different instruments (3130, 3730, 3500).

| | | Manual Analysis | | |
| --- | --- | --- | --- | --- |
| | Normal (0-44) | Inter- mediate (45-54) | Pre- Mutation (55-200) | Expansion (>200) |
| Pre-mutation (55-200) | 0 | 0 | 33 | 0 |
| Expansion (>200) | 0 | 0 | 0 | 37 |

8.1.10. Artificial Minor Allele Input Titration Study

Figure 20A:
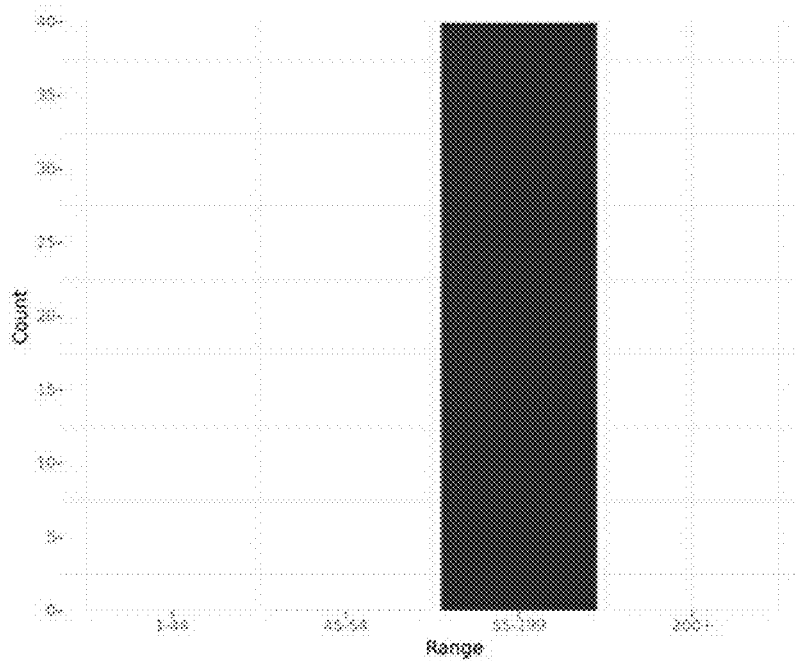
FIGS. 20A and 20B depict the results of artificial minor allele input titration testing.
Figure 20B:
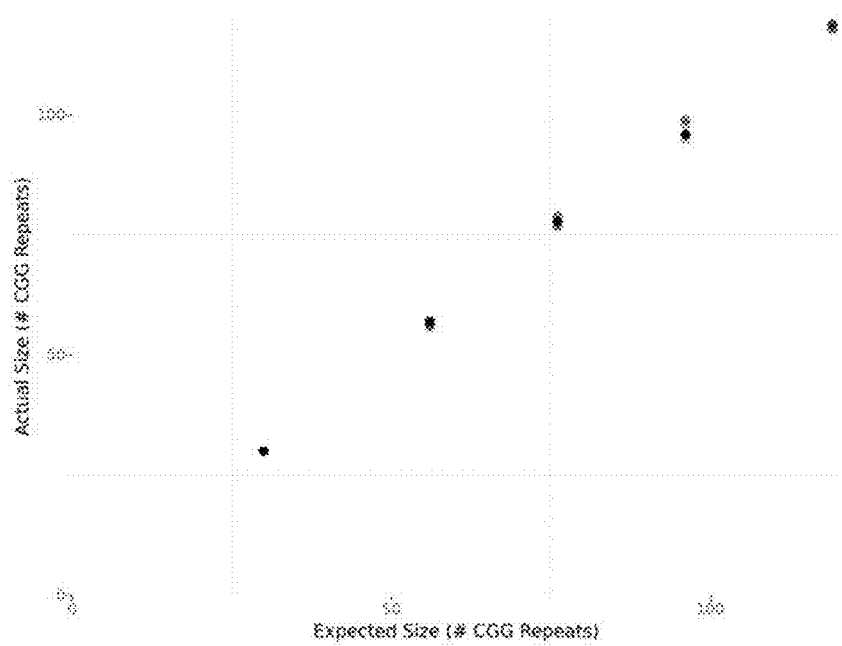

This analysis can flag low-level minor alleles across the full spectrum of genotypes. To demonstrate this capability, a study simulated the presence of low-level minor alleles in the background of a premutation sample (30 and 56 repeats). Minor alleles at 76, 96, and 119 were independently mixed at different input levels into the premutation background (20 ng/μl). The spectrum of input levels for minor alleles in this experiment included 20 ng/μl, 10 ng/μl, 5 ng/μl, 2.5 ng/μl, and 1 ng/μl. Analytical performance in sizing the premutation peaks in the sample and in sizing the mixed mosaic peaks was assessed. A total of 40 samples were evaluated in this study, and 100% of genotypes for samples passing QC (including minor alleles) were accurately sized in accordance with assay guidelines. FIG. 20A shows the genotype distribution of samples in the study. FIG. 20B shows a comparison between automated and manual genotypes produced for assay results, and Table 5 details a comparison between manual and automated categorical calls.

TABLE 5

Categorical performance table for artificial minor allele study. All genotypes are permutation genotypes because each sample was spiked with a permutation minor allele.

| | | Manual Analysis | | | |
| --- | --- | --- | --- | --- | --- |
| | | Normal (0-44) | Inter- mediate (45-54) | Pre- Mutation (55-200) | Expansion (>200) |
| Automated Analysis | Normal (0-44) | 0 | 0 | 0 | 0 |
| | Intermediate (45-54) | 0 | 0 | 0 | 0 |
| | Pre-mutation (55-200) | 0 | 0 | 38 | 0 |
| | Expansion (>200) | 0 | 0 | 0 | 0 |

8.1.11. Rush Sample Titration Study

Figure 21A:
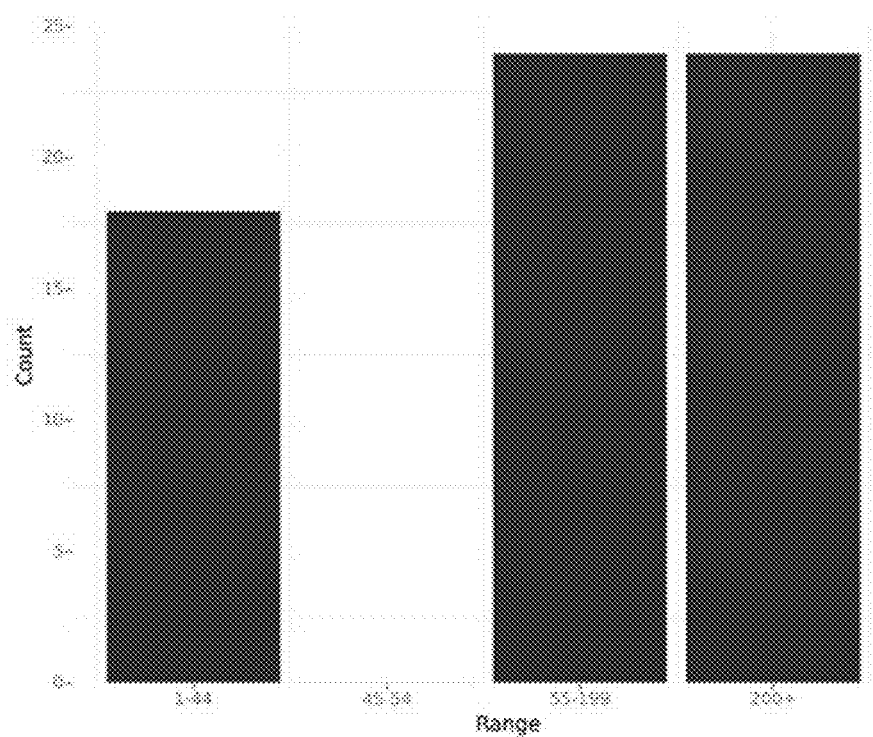
FIGS. 21A and 21B depict the results of RUSH sample titration testing.
Figure 21B:
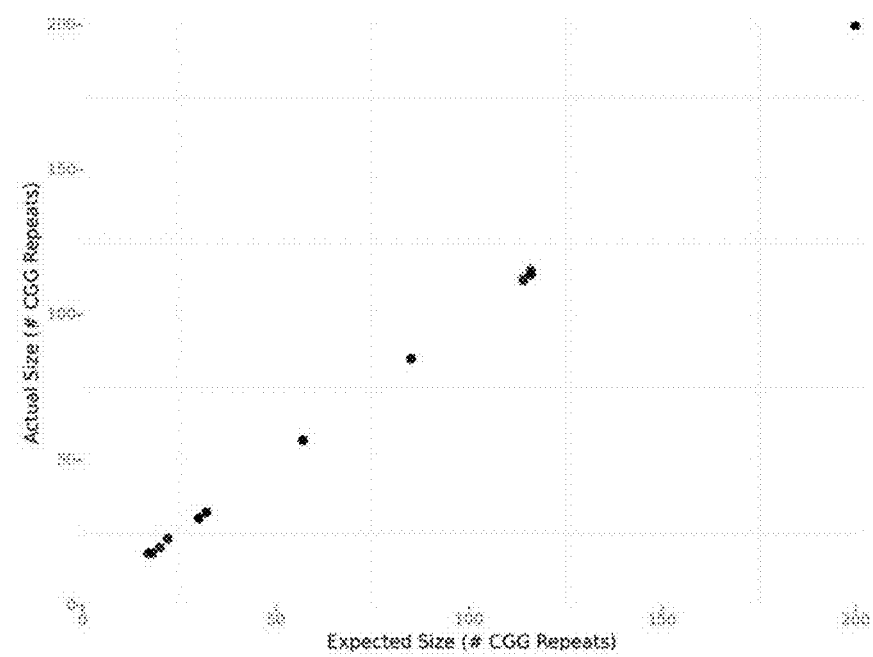

For this performance study, the RUSH set of samples underwent 5 2-fold serial dilutions from normal input amounts, in order to test stress-test the robustness of the algorithm at low sample input levels. The input levels tested in this experiment include 100% (20 ng/μl), 50% (10 ng/μl), 25% (5 ng/μl), 12.5% (2.5 ng/μl), 6.2% (1.25 ng/μl), and 3.1% (0.75 ng/μl). A total of 66 samples were evaluated in this study, and 100% of genotypes for samples passing QC were accurately sized in accordance with assay guidelines. FIG. 21A shows the genotype distribution of samples in the study. FIG. 21B shows a comparison between automated and manual genotypes produced for assay results, and Table 6 details a comparison between manual and automated categorical calls.

TABLE 6

Categorical performance table for titration study.

| | | Manual Analysis | | | |
| --- | --- | --- | --- | --- | --- |
| | | Normal (0-44) | Inter- mediate (45-54) | Pre- Mutation (55-200) | Expansion (>200) |
| Automated Analysis | Normal (0-44) | 15 | 0 | 0 | 0 |
| | Intermediate (45-54) | 0 | 0 | 0 | 0 |
| | Pre-mutation (55-200) | 0 | 0 | 22 | 0 |
| | Expansion (>200) | 0 | 0 | 0 | 22 |

8.1.12. QC Failure Mode Simulation Study

In order to test the ROX QC failure modes in the study, a sample set was generated to have two different types of ROX failures across a range of sample genotypes. The first failure mode included CE analysis of the RUSH sample set without labelled ROX fragments. The second failure mode included CE analysis of the RUST sample set with the ROX 400 ladder (ROX 1000 is required for this assay). A total of 13 samples without ROX and 12 samples with ROX 400 were analyzed and properly failed by the algorithm on the Sizing Ladder QC status.

8.1.13. Improvements in Result Turn-Around Time

Annotation device 130 greatly improves turn-around time for producing FMR1 results. For a 1000-sample cohort, manual operators were assumed to require 1 minute per sample, yielding a required 16.6 hours to process the entire cohort. In contrast, annotation device 130 produced results for the entire cohort (on a machine using 2 cores) in 1 minute and 24 seconds, demonstrating a >700 fold increase in time-to-result.

8.1.14. Analytical Capabilities

Figure 22A:
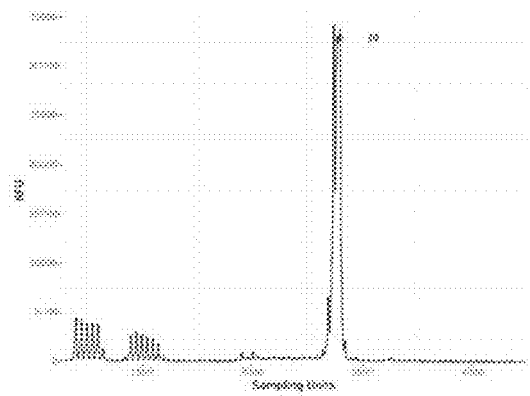
FIGS. 22A and 22B depict the exemplary results of automatic sizing analysis for samples with normal genotypes.
Figure 22B:
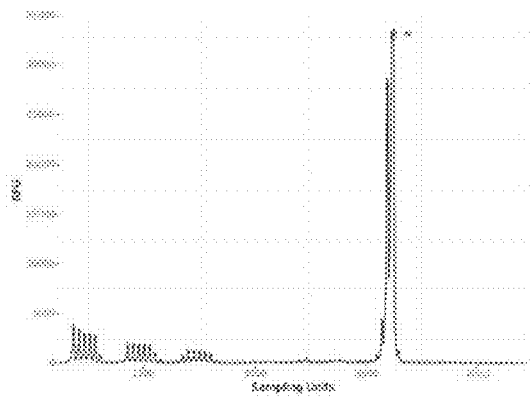
Figure 22C:
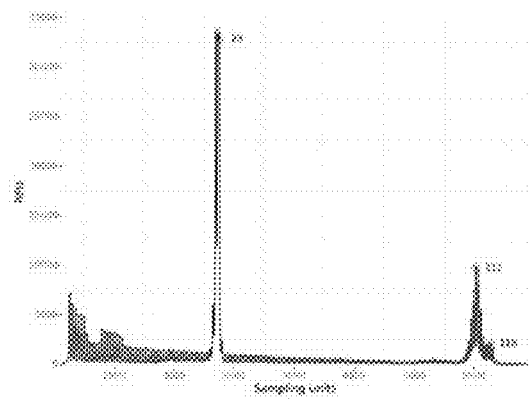
FIGS. 22C and 22D depict the exemplary results of automatic sizing analysis for samples with premutation genotypes.
Figure 22D:
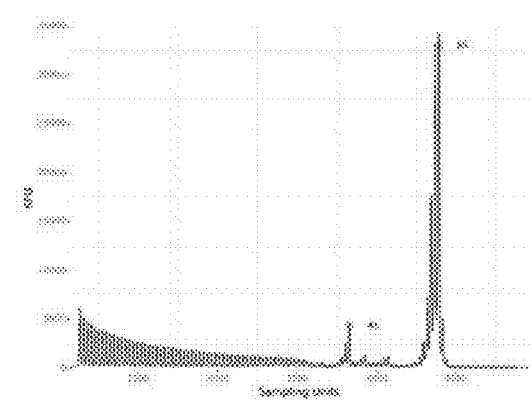
Figure 23A:
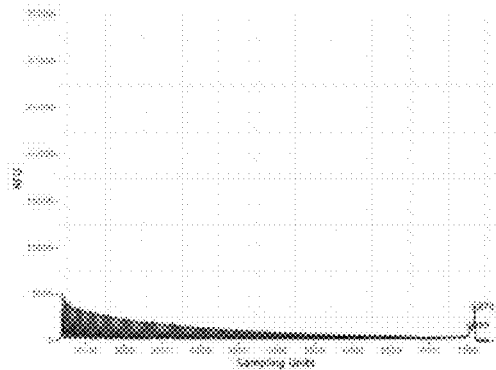
FIGS. 23A and 23B depict the exemplary results of automatic sizing analysis for expanded samples.
Figure 23B:
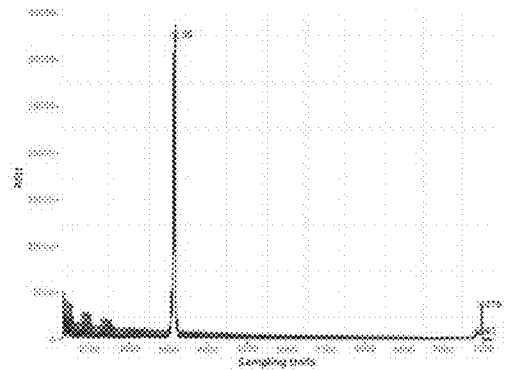
Figure 23C:
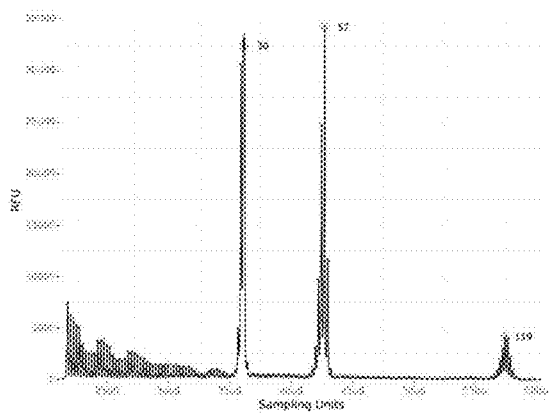
FIGS. 23C and 23D depict exemplary results of low-level minor allele identification and sizing.
Figure 23D:
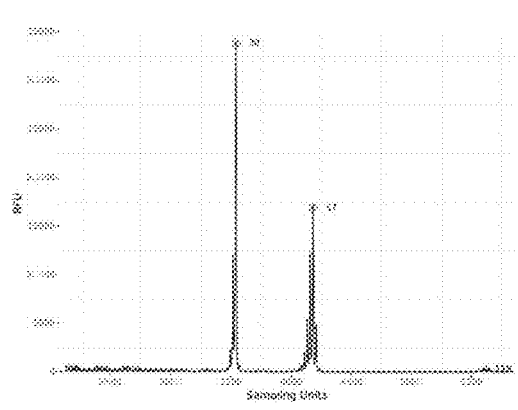
Figure 24:
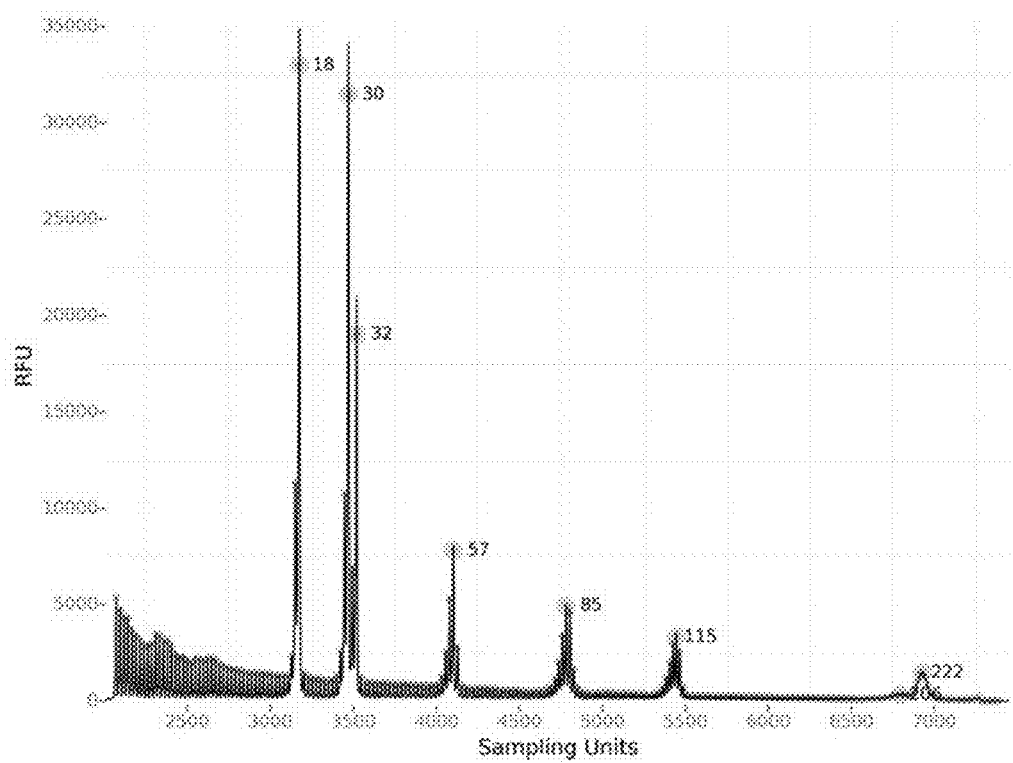
FIG. 24 depicts exemplary results of automatic sizing analysis for a control sample with a mixture of genotypes throughout the normal, permutation, and expanded genotype ranges.
Figure 25A:
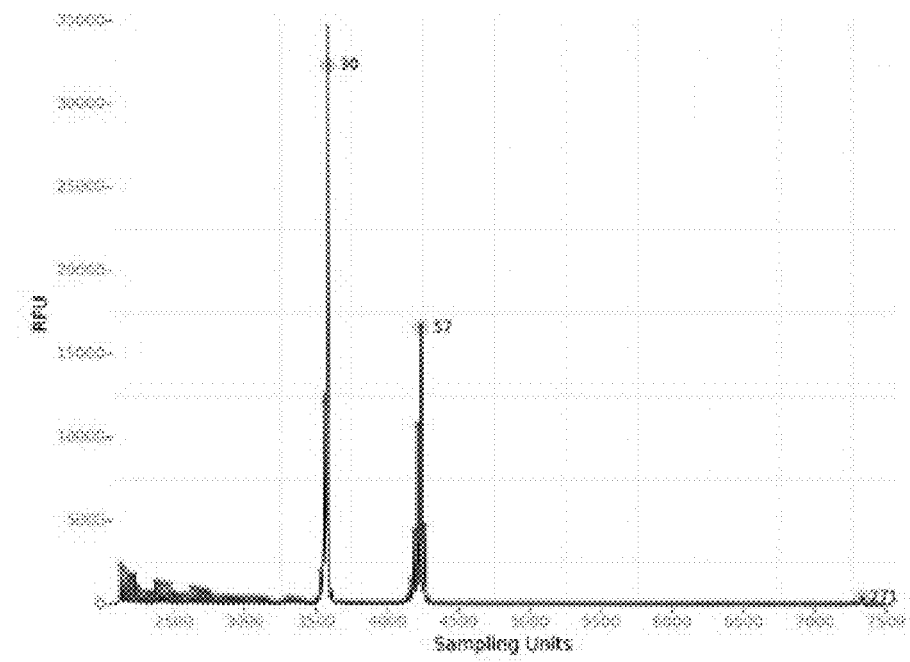
FIGS. 25A and 25B depicts exemplary results of automatic sizing analysis for a control sample including a mixture of 5% full mutation sample in a background of 95% permutation sample.
Figure 25B:
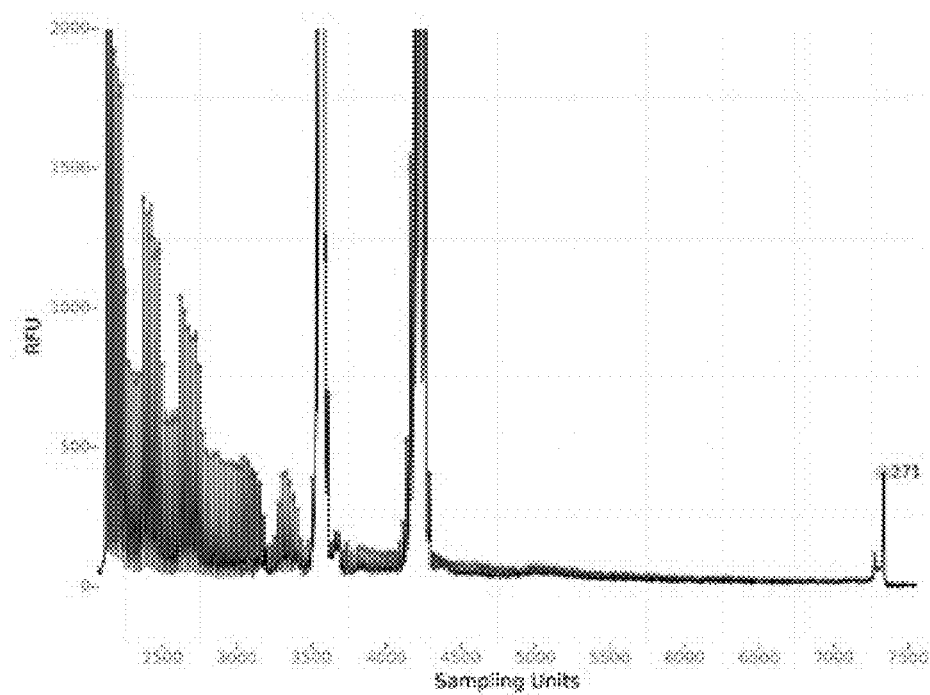

To further illustrate the analytical sensitivity of the assay, FIGS. 22A to 25B depict a range of different genotypes and corner-cases that the algorithm is able to correctly account for, producing sizing in accordance with manual operators. For example, FIGS. 22A and 22B depict the results of automatic sizing analysis for samples with normal genotypes. FIGS. 22C and 22D depict the results of automatic sizing analysis for samples with permutation genotypes. FIGS. 23A and 23B depict the results of automatic sizing analysis for expanded samples. FIGS. 23C and 23D depict the low-level minor allele identification and sizing. FIG. 24 depicts the results of automatic sizing analysis for a control sample with a mixture of genotypes throughout the normal, permutation, and expanded genotype ranges. FIGS. 25A and 25B depicts the results of automatic sizing analysis for a control sample including a mixture of 5% full mutation sample in a background of 95% permutation sample. FIG. 25A depicts the full sample including all called genotypes, while FIG. 25B depicts a zoomed-in version showing the full mutation call.

8.2. Discussion

An AmplideX® FMR1 PCR in-silico CGG fragment-size analysis tool was developed. This novel tool will enable rapid and accurate identification and sizing the full range of clinically relevant FMR1 genotypes, supporting high-volume sample processing and automated data analysis.

The studies summarized in the preceding examples demonstrate a high-performing annotation device for FMR1 PCR fragment size analysis with several important features. Among these are: (1) accurate genotyping for the entire clinically-relevant spectrum of FMR1 CGG repeat sizes; (2) the ability to accurately identify and size low-level mosaicism (down to 1%); (3) multi-instrument compatibility with the ABI family of Genetic Analyzers (3130, 3500, 3730); (4) robustness to signal artifacts produced by capillary electrophoresis instruments (air-bubbles, improper calibration, bleed-over artifacts, signal saturation, and collection noise); (5) significantly reduced analysis time when compared with manual processing of samples (>500 fold), and/or (6) automated QC analysis and sample flagging to protect users against poor amplification, contamination artifacts, poor-quality ROX ladders, or discrepancies in expected allele detection capability vs sample-inferred allele detection capabilities.

The preceding examples are intended to illustrate and in no way limit the present disclosure. Other embodiments of the disclosed devices and methods will be apparent to those skilled in the art from consideration of the specification and practice of the devices and methods disclosed herein.

The foregoing disclosed embodiments have been presented for purposes of illustration only. This disclosure is not exhaustive and does not limit the claimed subject matter to the precise embodiments disclosed. Those skilled in the art will appreciate from the foregoing description that modifications and variations are possible in light of the above teachings or may be acquired from practicing the inventions. In some aspects, methods consistent with disclosed embodiments may exclude disclosed method steps, or may vary the disclosed sequence of method steps or the disclosed degree of separation between method steps. For example, method steps may be omitted, repeated, or combined, as necessary, to achieve the same or similar objectives. In various aspects, non-transitory computer-readable media may store instructions for performing methods consistent with disclosed embodiments. These instructions may exclude disclosed method steps, or vary the disclosed sequence of method steps or disclosed degree of separation between method steps. For example, non-transitory computer-readable media may store instructions for performing methods consistent with disclosed embodiments that omit, repeat, or combine, as necessary, method steps to achieve the same or similar objectives. In certain aspects, systems need not necessarily include every disclosed part, and may include other undisclosed parts. For example, systems may omit, repeat, or combine, as necessary, parts to achieve the same or similar objectives. Accordingly, the claimed subject matter is not limited to the disclosed embodiments, but instead defined by the appended claims in light of their full scope of equivalents.

What is claimed is:

1. A method of sizing a repeat region of a nucleic acid, comprising:
   i. providing a nucleic acid sample;
   ii. amplifying a nucleic acid comprising a repeat region from the sample;
   iii. performing capillary electrophoresis to obtain a ladder of amplification products;
   iv. generating an internal sizing standard using the ladder of amplification products by:
       identifying a repeat profile in a channel of the ladder of amplification products;
       iteratively generating a set of repeat peak locations, the iterative generation comprising:
           determining a predicted peak location in the repeat profile using a previous peak location and an interval value,
           identifying a peak location within a window including the predicted peak location, and
           adding the identified peak location to the set of repeat peak locations when a signal intensity at the identified peak location satisfies an amplitude criterion; and
       estimating a linear relationship between repeat peak location and repeat fragment size using the set of repeat peak locations and a set of corresponding fragment sizes; and
   v. sizing the repeat region using the internal sizing standard,
   wherein sizing the repeat region further comprises using an external sizing standard,
   wherein the external sizing standard is generated by:
       identifying peaks in a channel of the ladder of amplification products, the peaks exceeding a local noise threshold;
       iteratively re-estimating, using identified peaks in a first region of the channel, a linear relationship between peak location and fragment size using a first set of fragment sizes and a first set of corresponding peak locations, the iterative re-estimation comprising:
           including progressively smaller fragment sizes into the first set of fragment sizes, and
           including peak locations corresponding to the progressively smaller fragment sizes into the first set of corresponding peak locations;
       estimating, using identified peaks in a second region of the channel, a non-linear relationship between peak location and fragment size for a second region of the channel using a second set of fragment sizes and a second set of corresponding peak locations; and
       combining the linear relationship and the nonlinear relationship, thereby generating the external sizing standard.

2. The method of claim 1, wherein the iterative re-estimation further comprises:
   determining a predicted peak location using one of the progressively smaller fragment sizes and a re-estimated linear relationship between peak location and fragment size;
   determining an actual peak location in the channel within a window including the predicted peak location; and
   including the actual peak location into the first set of corresponding peak locations.

3. The method of claim 1, wherein sizing the repeat region further comprises:
   generating a mobility corrected sizing standard by generating an affine transformation using the internal sizing standard and the external sizing standard; and
   applying the affine transformation to the external sizing standard to obtain the mobility corrected sizing standard.

4. A method of sizing a repeat region of a nucleic acid, comprising:
  i. providing a nucleic acid sample;
  ii. amplifying a nucleic acid comprising a repeat region from the sample;
  iii. performing capillary electrophoresis to obtain a ladder of amplification products;
  iv. generating an internal sizing standard using the ladder of amplification products by:
    identifying a repeat profile in a channel of the ladder of amplification products;
    iteratively generating a set of repeat peak locations, the iterative generation comprising:
      determining a predicted peak location in the repeat profile using a previous peak location and an interval value,
      identifying a peak location within a window including the predicted peak location, and
      adding the identified peak location to the set of repeat peak locations when a signal intensity at the identified peak location satisfies an amplitude criterion; and
    estimating a linear relationship between repeat peak location and repeat fragment size using the set of repeat peak locations and a set of corresponding fragment sizes; and
  v. sizing the repeat region using the internal sizing standard,
wherein sizing the repeat region further comprises identifying at least one gene-specific peak; and sizing the at least one gene-specific peak using the ladder of amplification products comprising
  generating a dynamic threshold from a background model by piecewise scaling the background model to obtain the dynamic threshold;
  determining gene-specific peak locations in a repeat profile using the dynamic threshold;
  associating repeat sizes with the gene-specific peak locations using the ladder of amplification products; and
  outputting an indication of the gene-specific peak sizes.

5. The method of claim 4, wherein piecewise scaling the background model comprises:
  determining a first region of the background model corresponding to amplification products with sizes above a first fragment size and below a second fragment size;
  determining a second region of the background model corresponding to amplification products with sizes above the second fragment size;
  multiplying the first region of the background model by a first scaling factor that varies from an initial scaling factor to a second scaling factor less than the initial scaling factor; and
  multiplying the second region of the background model by the second scaling factor.

6. The method of claim 4, wherein determining gene-specific peak locations in the repeat profile comprises:
  identifying a first peak in the repeat profile at a first location; and
  determining a first value of the repeat profile at the first location exceeds a first value of the dynamic threshold at the first location.

7. The method of claim 6, wherein determining gene-specific peak locations in the repeat profile further comprises:
  identifying a second peak in the repeat profile at a second location, the second peak adjacent to the first peak;
  determining a second value of the repeat profile at the second location satisfies an amplitude criterion, the amplitude criterion based on the first value; and
  determining the second value of the repeat profile at the second location exceeds a second value of the dynamic threshold at the second location.

8. A method of sizing a repeat region of a nucleic acid, comprising:
  i. providing a nucleic acid sample;
  ii. amplifying a nucleic acid comprising a repeat region from the sample;
  iii. performing capillary electrophoresis to obtain a ladder of amplification products;
  iv. generating an internal sizing standard using the ladder of amplification products by:
    identifying a repeat profile in a channel of the ladder of amplification products;
    iteratively generating a set of repeat peak locations, the iterative generation comprising:
      determining a predicted peak location in the repeat profile using a previous peak location and an interval value,
      identifying a peak location within a window including the predicted peak location, and
      adding the identified peak location to the set of repeat peak locations when a signal intensity at the identified peak location satisfies an amplitude criterion; and
    estimating a linear relationship between repeat peak location and repeat fragment size using the set of repeat peak locations and a set of corresponding fragment sizes; and
  v. sizing the repeat region using the internal sizing standard,
wherein sizing a repeat region further comprises:
  (a) dynamically determining a threshold for calling peaks in a repeat profile;
  (b) calling peaks in a repeat profile using a sliding window;
  (c) interpolating peaks below an amplitude threshold in a repeat profile;
  (d) generating a calibration curve that maps from sampling units to base pair units using estimated peak locations in a repeat profile;
  (e) correcting a first channel for signal artifacts;
  (f) extending the dynamic range of a first channel configured to detect a first electromagnetically detectable moiety; and/or
  (g) determining satisfaction of sizing standard criteria, a repeat profile signal-to-noise criterion, a repeat profile contamination criterion, and/or a minor allele sensitivity criterion, and
wherein correcting a first channel for signal artifacts comprises:
  a) identifying a window in the first channel including a potential air bubble location; determining a correlation between signal intensities for channels within the window; and replacing, based on the determined correlation, the signal intensities for the channels within the window; and/or
  b) identifying a bleed-over location based on signal intensities for the first channel; determining a window including the bleed-over location based on signal intensities for a second channel; and replacing the signal intensities for the second channel.

9. A method of sizing a repeat region of a nucleic acid, comprising:
   i. providing a nucleic acid sample;
   ii. amplifying a nucleic acid comprising a repeat region from the sample;
   iii. performing capillary electrophoresis to obtain a ladder of amplification products;
   iv. generating an internal sizing standard using the ladder of amplification products by:
      identifying a repeat profile in a channel of the ladder of amplification products;
      iteratively generating a set of repeat peak locations, the iterative generation comprising:
         determining a predicted peak location in the repeat profile using a previous peak location and an interval value,
         identifying a peak location within a window including the predicted peak location, and
         adding the identified peak location to the set of repeat peak locations when a signal intensity at the identified peak location satisfies an amplitude criterion; and
      estimating a linear relationship between repeat peak location and repeat fragment size using the set of repeat peak locations and a set of corresponding fragment sizes; and
   v. sizing the repeat region using the internal sizing standard,
   wherein sizing a repeat region further comprises:
      a) dynamically determining a threshold for calling peaks in a repeat profile;
      b) calling peaks in a repeat profile using a sliding window;
      c) interpolating peaks below an amplitude threshold in a repeat profile;
      d) generating a calibration curve that maps from sampling units to base pair units using estimated peak locations in a repeat profile;
      e) correcting a first channel for signal artifacts;
      f) extending the dynamic range of a first channel configured to detect a first electromagnetically detectable moiety; and/or
      g) determining satisfaction of sizing standard criteria, a repeat profile signal-to-noise criterion, a repeat profile contamination criterion, and/or a minor allele sensitivity criterion, and
   wherein extending the dynamic range of a first channel comprises:
      identifying a window in the first channel including a saturated region;
      determining combined signal intensities using the signal intensities for the first channel within the window and the signal intensities for a second channel configured to detect a second electromagnetically detectable moiety within the window; and
      replacing the signal intensities for the first channel with the combined signal intensities.

10. A method of sizing a repeat region of a nucleic acid, comprising:
   i. providing a nucleic acid sample;
   ii. amplifying a nucleic acid comprising a repeat region from the sample;
   iii. performing capillary electrophoresis to obtain a ladder of amplification products;
   iv. generating an internal sizing standard using the ladder of amplification products by:
      identifying a repeat profile in a channel of the ladder of amplification products;
      iteratively generating a set of repeat peak locations, the iterative generation comprising:
         determining a predicted peak location in the repeat profile using a previous peak location and an interval value,
         identifying a peak location within a window including the predicted peak location, and
         adding the identified peak location to the set of repeat peak locations when a signal intensity at the identified peak location satisfies an amplitude criterion; and
      estimating a linear relationship between repeat peak location and repeat fragment size using the set of repeat peak locations and a set of corresponding fragment sizes; and
   v. sizing the repeat region using the internal sizing standard,
   wherein sizing a repeat region further comprises:
      (a) dynamically determining a threshold for calling peaks in a repeat profile;
      (b) calling peaks in a repeat profile using a sliding window;
      (c) interpolating peaks below an amplitude threshold in a repeat profile;
      (d) generating a calibration curve that maps from sampling units to base pair units using estimated peak locations in a repeat profile;
      (e) correcting a first channel for signal artifacts;
      (f) extending the dynamic range of a first channel configured to detect a first electromagnetically detectable moiety; and/or
      (g) determining satisfaction of sizing standard criteria, a repeat profile signal-to-noise criterion, a repeat profile contamination criterion, and/or a minor allele sensitivity criterion, and
   wherein:
      a) the sizing standard criteria comprise an internal sizing standard goodness-of-fit criterion, an external sizing standard goodness-of-fit criterion, and/or a consistency criterion that compares the internal sizing standard to the external sizing standard;
      b) the repeat profile contamination criterion is failed when a repeat size associated with a location of a gene-specific peak is less than zero; and/or
      c) the minor allele sensitivity criterion is satisfied when a ratio of a noise value of a repeat profile to a maximum of the values of the repeat profile at a location of a gene-specific peak exceeds a threshold value.

* * * * *

SEQUENCE LISTING

```
<160> NUMBER OF SEQ ID NOS: 55

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
cggtggaggg ccgcctctga gc                                            22

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
caggcgctca gctccgtttc ggttt                                         25

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cagtcaggcg ctcagctccg tttcg                                         25

<210> SEQ ID NO 4
<211> LENGTH: 24
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 4
tccggtggag ggccgcctct gagc                                            24

<210> SEQ ID NO 5
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ggttcggcct cagtcaggcg ctcagctccg tttcg                                35

<210> SEQ ID NO 6
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gggttcggcc tcagtcaggc gctcagctcc gtttcg                               36

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gcgggccggg ggttcggcct cagtca                                          26

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cagcgggccg ggggttcggc ctcag                                           25

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gcagcgggcc gggggttcgg cctca                                           25

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Synthetic
```

```
                           primer

<400> SEQUENCE: 10
gggccggggg ttcggcctca gtcag                                         25

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ggggttcggc ctcagtcagg cgctca                                        26

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ggggttcggc ctcagtcagg cgctcag                                       27

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ggcgctcagc tccgtttcgg tttcacttcc                                    30

<210> SEQ ID NO 14
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tcaggcgctc agctccgttt cggtttca                                      28

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cacttccggt ggagggccgc ctctga                                        26

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 16
ttccggtgga gggccgcctc tgagc                                          25

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cgcacttcca ccaccagctc ctcca                                          25

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ggagcccgcc cccgagaggt g                                              21

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gggagcccgc ccccgagagg t                                              21

<210> SEQ ID NO 20
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
cgcacttcca ccaccagctc ctccat                                         26

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cgggagcccg ccccgagag gtg                                             23

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 22
ccgggagccc gcccccgaga ggt                                          23

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ccgggagccc gcccccgaga ggtg                                         24

<210> SEQ ID NO 24
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
cgccgggagc ccgcccccga gaggtg                                       26

<210> SEQ ID NO 25
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gcgccgggag cccgcccccg agaggt                                       26

<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
cgccgggagc ccgcccccga gaggt                                        25

<210> SEQ ID NO 27
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gcgccattgg agccccgcac ttccacca                                     28

<210> SEQ ID NO 28
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
```
gcgccattgg agccccgcac ttcca                                              25

<210> SEQ ID NO 29
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
agcgccattg gagccccgca cttcc                                              25

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
cgccattgga gccccgcact tccac                                              25

<210> SEQ ID NO 31
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ttggagcccc gcacttccac cacca                                              25

<210> SEQ ID NO 32
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
agccccgcac ttccaccacc agctcctc                                           28

<210> SEQ ID NO 33
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gagccccgca cttccaccac cagctcct                                           28

<210> SEQ ID NO 34
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
cattggagcc ccgcacttcc accaccag                                              28

<210> SEQ ID NO 35
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
cccgcacttc caccaccagc tcctccatct                                            30

<210> SEQ ID NO 36
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
tagaaagcgc cattggagcc ccgcacttcc                                            30

<210> SEQ ID NO 37
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
aagcgccatt ggagccccgc acttcc                                                26

<210> SEQ ID NO 38
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
tcaggcgctc agctccgttt cggtttcact tccggt                                     36

<210> SEQ ID NO 39
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
agcgtctact gtctcggcac ttgcccgccg ccgccg                                     36

<210> SEQ ID NO 40
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
ggcgctcagc tccgtttcgg tttca                                                 25

<210> SEQ ID NO 41
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
tcaggcgctc agctccgttt cggtttcacg gcggcggcgg cgg                43

<210> SEQ ID NO 42

<400> SEQUENCE: 42

000

<210> SEQ ID NO 43
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
aagcgccatt ggagccccgc acttccccgc cgccgccgcc g                  41

<210> SEQ ID NO 44
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
tcaggcgctc agctccgttt cggtttcacg gcggcggcgg cgga               44

<210> SEQ ID NO 45
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
aagcgccatt ggagccccgc acttccccgc cgccgccgcc t                  41

<210> SEQ ID NO 46
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
tgcgcctccg ccgccgcggg cgcaggcacc gcaaccgca                     39

<210> SEQ ID NO 47
<211> LENGTH: 33
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 47
cgcagcctgt agcaagctct ggaactcagg agt                               33

<210> SEQ ID NO 48
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
tgcgcctccg ccgccgcggg cgcaggcacc gcaaccgcac cccggccccg gccccgg     57

<210> SEQ ID NO 49
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
cgcagcctgt agcaagctct ggaactcagg agtcgccggg gccggggccg ggg         53

<210> SEQ ID NO 50
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
ccaaagcatt gggattactg gc                                          22

<210> SEQ ID NO 51
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
gattgcttga gcctaggcat tc                                          22

<210> SEQ ID NO 52
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
aataataata at                                                     12

<210> SEQ ID NO 53
<211> LENGTH: 10
<212> TYPE: DNA
<213> ORGANISM: Artificial Sequence
<220> FEATURE:
<223> OTHER INFORMATION: Description of Artificial Sequence: Synthetic

```
            oligonucleotide

<400> SEQUENCE: 53
aataaataat                                                           10

<210> SEQ ID NO 54
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
aaataaaaat                                                           10

<210> SEQ ID NO 55
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
aataaaaaat                                                           10
```